(12) United States Patent
Wang et al.

(10) Patent No.: US 10,927,176 B2
(45) Date of Patent: Feb. 23, 2021

(54) TUMOR-SPECIFIC ANTI-EGFR ANTIBODY AND APPLICATION THEREOF

(71) Applicant: CARSGEN THERAPEUTICS CO., LTD., Shanghai (CN)

(72) Inventors: Huamao Wang, Shanghai (CN); Bo Song, Shanghai (CN)

(73) Assignee: CARSGEN THERAPEUTICS CO., LTD., Shanghai (CN)

( * ) Notice: Subject to any disclaimer, the term of this patent is extended or adjusted under 35 U.S.C. 154(b) by 126 days.

(21) Appl. No.: 15/746,711

(22) PCT Filed: Jul. 21, 2016

(86) PCT No.: PCT/CN2016/090892
§ 371 (c)(1),
(2) Date: Jan. 22, 2018

(87) PCT Pub. No.: WO2017/012567
PCT Pub. Date: Jan. 26, 2017

(65) Prior Publication Data
US 2018/0327501 A1   Nov. 15, 2018

(30) Foreign Application Priority Data
Jul. 21, 2015   (CN) .......................... 201510431481.6

(51) Int. Cl.
| | | |
|---|---|---|
| A61K 39/395 | (2006.01) | |
| C07K 16/28 | (2006.01) | |
| G01N 33/574 | (2006.01) | |
| C07K 16/30 | (2006.01) | |
| C12N 15/63 | (2006.01) | |
| C12N 15/62 | (2006.01) | |
| C12N 5/10 | (2006.01) | |
| A61K 48/00 | (2006.01) | |
| C07K 19/00 | (2006.01) | |
| C07K 16/46 | (2006.01) | |
| A61P 35/00 | (2006.01) | |
| C07K 14/54 | (2006.01) | |
| C07K 14/705 | (2006.01) | |
| C07K 14/715 | (2006.01) | |
| C12N 15/113 | (2010.01) | |
| A61K 38/00 | (2006.01) | |
| A61K 39/00 | (2006.01) | |

(52) U.S. Cl.
CPC ........ *C07K 16/2863* (2013.01); *A61K 39/395* (2013.01); *A61K 48/00* (2013.01); *A61P 35/00* (2018.01); *C07K 14/54* (2013.01); *C07K 14/5434* (2013.01); *C07K 14/5443* (2013.01); *C07K 14/70517* (2013.01); *C07K 14/70521* (2013.01); *C07K 14/70578* (2013.01); *C07K 14/7158* (2013.01); *C07K 16/2809* (2013.01); *C07K 16/30* (2013.01); *C07K 16/46* (2013.01); *C07K 16/468* (2013.01); *C07K 19/00* (2013.01); *C12N 5/10* (2013.01); *C12N 15/1138* (2013.01); *C12N 15/62* (2013.01); *C12N 15/63* (2013.01); *G01N 33/574* (2013.01); *A61K 38/00* (2013.01); *A61K 2039/572* (2013.01); *C07K 2317/31* (2013.01); *C07K 2317/56* (2013.01); *C07K 2317/565* (2013.01); *C07K 2317/569* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2310/14* (2013.01); *C12N 2320/31* (2013.01); *C12N 2320/32* (2013.01)

(58) Field of Classification Search
None
See application file for complete search history.

(56) References Cited

U.S. PATENT DOCUMENTS 10,023,639 B2 *   7/2018   Li ...................... C07K 16/2863

FOREIGN PATENT DOCUMENTS

| CN | 1124501 | 6/1996 |
| CN | 103113470 | 5/2013 |
| CN | 103382223 | 11/2013 |
| CN | 104087607 | 10/2014 |

OTHER PUBLICATIONS

International Search Report for international appl. No. PCT/CN2016/090892, dated Oct. 26, 2016 (8 pages, including English translation).

* cited by examiner

*Primary Examiner* — Michael D Pak
(74) *Attorney, Agent, or Firm* — Hamre, Schumann, Mueller & Larson, P.C.

(57) ABSTRACT

The present invention provides a tumor-specific anti-EGFR antibody and application thereof. The antibody can be used for preparing targeted antitumor drugs and tumor diagnosis drugs.

5 Claims, 6 Drawing Sheets
Specification includes a Sequence Listing.

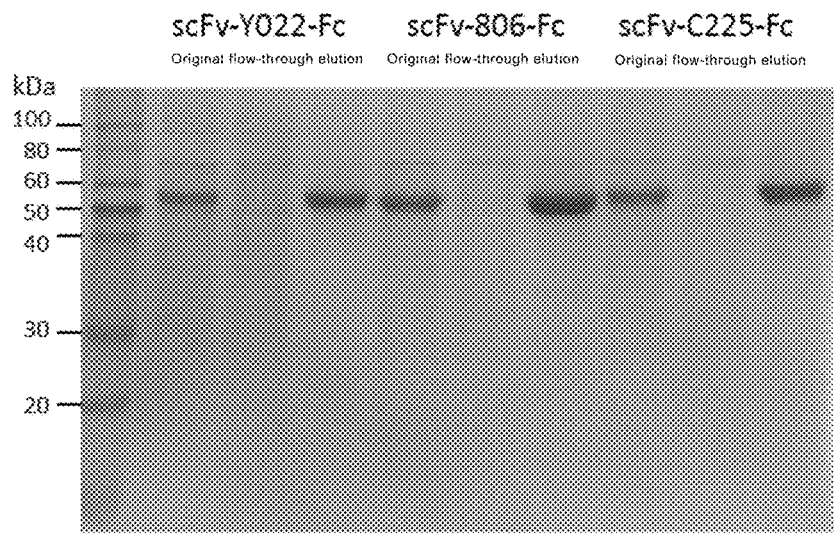
Fig. 4
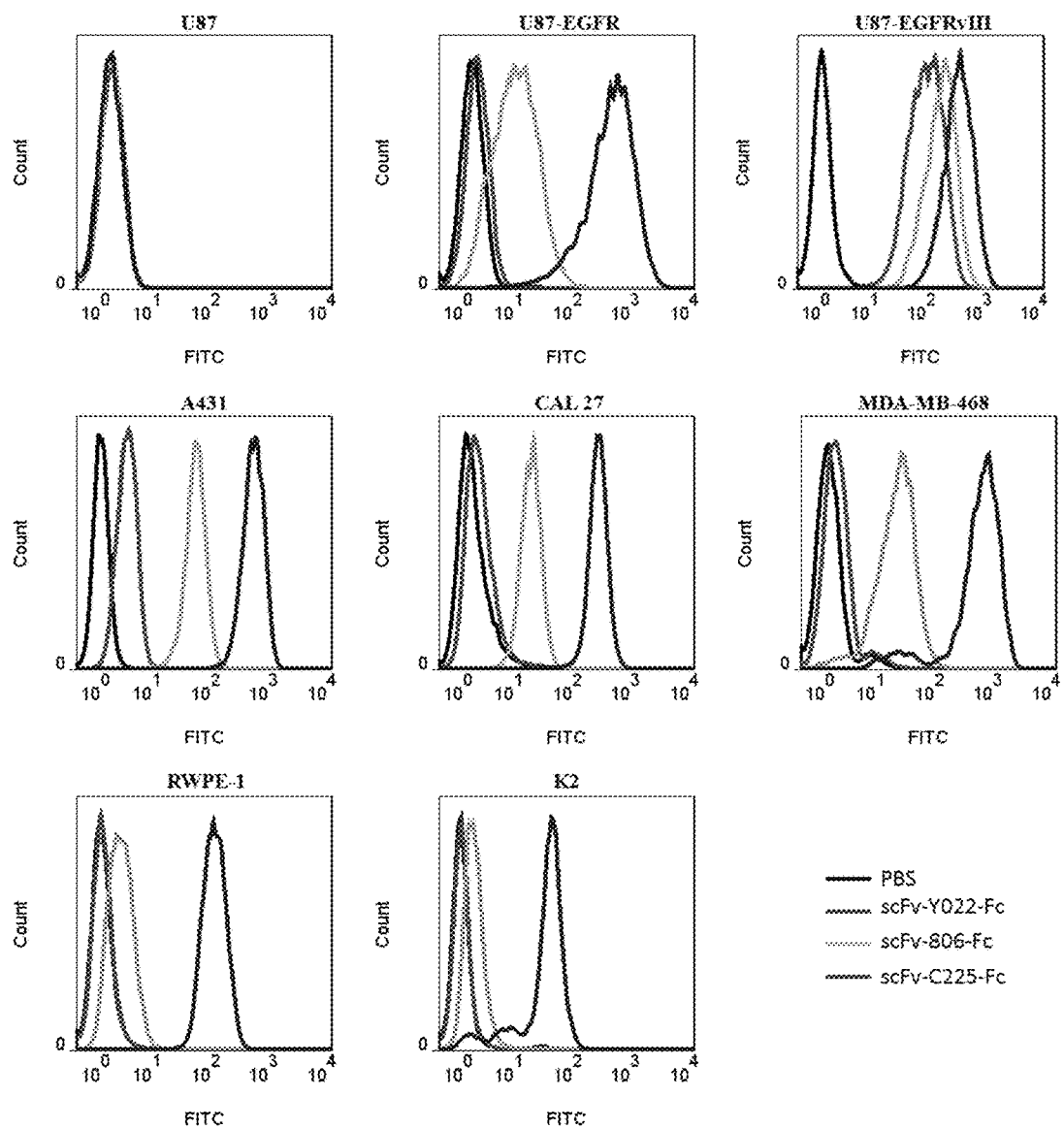

Fig. 5
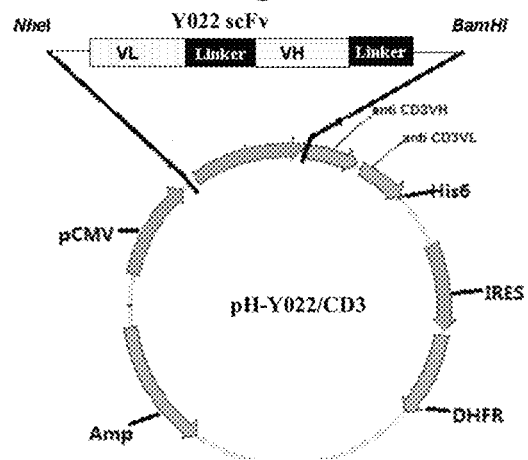
Fig. 6
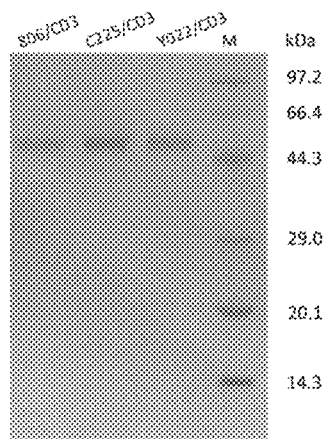
Fig. 7

SEQUENCE LISTING

<160> NUMBER OF SEQ ID NOS: 77

<210> SEQ ID NO 1
<211> LENGTH: 16
<212> TYPE: PRT
<213> ORGANISM: Homo Sapiens

<400> SEQUENCE: 1

Cys Gly Ala Asp Ser Tyr Glu Met Glu Glu Asp Gly Val Arg Lys Cys
1               5                   10                  15

<210> SEQ ID NO 2
<211> LENGTH: 717
<212> TYPE: DNA
<213> ORGANISM: Artificial sequence
<220> FEATURE:
<223> OTHER INFORMATION: encoding sequence of single chain antibody 7B3

<400> SEQUENCE: 2

```
gatattcaga tgacccagag cccgagcagc ctgagcgcga gcgtgggcga ccgtgtgacc      60
attacctgcc atgcgagcca ggatattaac agcaacattg ctggctgca gcagaaaccg     120
ggcaaagcgt ttaaaggcct gatttatcat ggcaaaaacc tggaagatgg cgtgccgagc     180
cgttttagcg gcagcggcag cggcaccgat tttaccctga ccattagcag cctgcagccg     240
gaagattttg cgacctatta ttgcgttcag tacgcccagt tcccatatac atttggccag     300
ggcaccaaag tggaaattaa acgtggtgga ggcggttcag gcggaggtgg ctctggcggt     360
ggcggatcgg atgtgcagct ggtggaaagc ggcggcggcc tggtgcagcc gggcggcagc     420
ctgcgtctga gctgcgcggt gagcggctat agcattacca gcgattatgc gtggaactgg     480
attcgtcagg cgccgggcaa aggcctggaa tggctgggct atattagcta tcgtggccgc     540
accagctata acccgagcct gaaaagccgt attagcatta cccgtgataa cagcaaaaac     600
acctttttcc tgcagctgaa cagcctgcgt gcggaagata ccgcggtgta ttattgcgcg     660
cgcctgggac gcggcttccg ctactggggc cagggcaccc tggtgaccgt gagcagc        717
```

<210> SEQ ID NO 3
<211> LENGTH: 239
<212> TYPE: PRT
<213> ORGANISM: Artificial sequence
<220> FEATURE:
<223> OTHER INFORMATION: amino acid sequence of single chain antibody
     7B3

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Ser Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Ala Gln Phe Pro Tyr
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175
```

-continued

```
Tyr Arg Gly Arg Thr Ser Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235

<210> SEQ ID NO 4
<211> LENGTH: 42
<212> TYPE: DNA
<213> ORGANISM: Artificial sequence
<220> FEATURE:
<223> OTHER INFORMATION: Primer

<400> SEQUENCE: 4
ataacaggcc cagccggcca tggatattca gatgacccag ag          42

<210> SEQ ID NO 5
<211> LENGTH: 69
<212> TYPE: DNA
<213> ORGANISM: Artificial sequence
<220> FEATURE:
<223> OTHER INFORMATION: Primer
<220> FEATURE:
<222> LOCATION: (26)..(27)
<223> OTHER INFORMATION: n is a, c, g, or t
<220> FEATURE:
<222> LOCATION: (32)..(33)
<223> OTHER INFORMATION: n is a, c, g, or t
<220> FEATURE:
<222> LOCATION: (35)..(36)
<223> OTHER INFORMATION: n is a, c, g, or t
<220> FEATURE:
<222> LOCATION: (38)..(39)
<223> OTHER INFORMATION: n is a, c, g, or t
<220> FEATURE:
<222> LOCATION: (41)..(42)
<223> OTHER INFORMATION: n is a, c, g, or t
<220> FEATURE:
<222> LOCATION: (47)..(48)
<223> OTHER INFORMATION: n is a, c, g, or t

<400> SEQUENCE: 5
cactttggtg ccctggccaa atgtmnntgg gnnmnnmnnm nnctgmnngc aataataggt    60
cgcaaaatc                                                           69

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
acatttggcc agggcaccaa ag          22

<210> SEQ ID NO 7
<211> LENGTH: 29
<212> TYPE: DNA
<213> ORGANISM: Artificial sequence
<220> FEATURE:
<223> OTHER INFORMATION: Primer

<400> SEQUENCE: 7
ataaatgcgg ccgcgctgct cacggtcac          29
```

-continued

```
<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
tcgcaattcc tttagttgtt cc                                              22

<210> SEQ ID NO 9
<211> LENGTH: 57
<212> TYPE: DNA
<213> ORGANISM: Artificial sequence
<220> FEATURE:
<223> OTHER INFORMATION: Primer
<220> FEATURE:
<222> LOCATION: (23)..(24)
<223> OTHER INFORMATION: n is a, c, g, or t
<220> FEATURE:
<222> LOCATION: (26)..(27)
<223> OTHER INFORMATION: n is a, c, g, or t
<220> FEATURE:
<222> LOCATION: (29)..(30)
<223> OTHER INFORMATION: n is a, c, g, or t
<220> FEATURE:
<222> LOCATION: (32)..(33)
<223> OTHER INFORMATION: n is a, c, g, or t
<220> FEATURE:
<222> LOCATION: (35)..(36)
<223> OTHER INFORMATION: n is a, c, g, or t
<220> FEATURE:
<222> LOCATION: (38)..(39)
<223> OTHER INFORMATION: n is a, c, g, or t

<400> SEQUENCE: 9
cagggtgccc tggccccagt aannmnnmnn mnnmnnmnng cgcgcgcaat aatacac        57

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
tactggggcc agggcaccct g                                               21

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
ggaataggtg tatcaccgta ctcag                                           25

<210> SEQ ID NO 12
<211> LENGTH: 717
<212> TYPE: DNA
<213> ORGANISM: Artificial sequence
<220> FEATURE:
<223> OTHER INFORMATION: nucelotide sequence of single chain antibody
      Y022

<400> SEQUENCE: 12
gatattcaga tgacccagag cccgagcagc ctgagcgcga gcgtgggcga ccgtgtgacc      60
```

```
attacctgcc atgcgagcca ggatattaac gtgaacattg gctggctgca gcagaaaccg    120
ggcaaagcgt ttaaaggcct gatttatcat ggcaaaaacc tggaagatgg cgtgccgagc    180
cgttttagcg gcagcggcag cggcaccgat tttaccctga ccattagcag cctgcagccg    240
gaagattttg cgacctatta ttgcaatcag tatgaaaata tcccactgac atttggccag    300
ggcaccaaag tggaaattaa acgtggtgga ggcggttcag gcggaggtgg ctctggcggt    360
ggcggatcgg atgtgcagct ggtggaaagc ggcggcggcc tggtgcagcc gggcggcagc    420
ctgcgtctga gctgcgcggt gagcggctat agcattacca gcgattatgc gtggaactgg    480
attcgtcagg cgccgggcaa aggcctggaa tggctgggct atattagcta tcgtggccgc    540
acccagtata acccgagcct gaaaagccgt attagcatta cccgtgataa cagcaaaaac    600
accttttttcc tgcagctgaa cagcctgcgt gcggaagata ccgcggtgta ttattgcgcg    660
cgcatgggta agaattggga ttactggggc cagggcaccc tggtgaccgt gagcagc       717
```

<210> SEQ ID NO 13
<211> LENGTH: 239
<212> TYPE: PRT
<213> ORGANISM: Artificial sequence
<220> FEATURE:
<223> OTHER INFORMATION: amino acid sequence of single chain antibody Y022

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Ile Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Gln Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Met Gly Lys
    210                 215                 220

Asn Trp Asp Tyr Trp Gly Gln Gly Thr Leu Val Thr Val Ser Ser
225                 230                 235
```

```
<210> SEQ ID NO 14
<211> LENGTH: 30
<212> TYPE: DNA
<213> ORGANISM: Artificial sequence
<220> FEATURE:
<223> OTHER INFORMATION: Primer

<400> SEQUENCE: 14
acagtgctag cagatattca gatgacccag                                      30

<210> SEQ ID NO 15
<211> LENGTH: 32
<212> TYPE: DNA
<213> ORGANISM: Artificial sequence
<220> FEATURE:
<223> OTHER INFORMATION: Primer

<400> SEQUENCE: 15
aagaatgcgg ccgcgctgct cacggtcacc ag                                   32

<210> SEQ ID NO 16
<211> LENGTH: 31
<212> TYPE: DNA
<213> ORGANISM: Artificial sequence
<220> FEATURE:
<223> OTHER INFORMATION: Primer

<400> SEQUENCE: 16
acagtgctag cagacatcct gatgacccaa t                                    31

<210> SEQ ID NO 17
<211> LENGTH: 32
<212> TYPE: DNA
<213> ORGANISM: Artificial sequence
<220> FEATURE:
<223> OTHER INFORMATION: Primer

<400> SEQUENCE: 17
aagaatgcgg ccgctgcaga gacagtgacc ag                                   32

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
acagtgctag cagacatctt gctgactcag                                      30

<210> SEQ ID NO 19
<211> LENGTH: 32
<212> TYPE: DNA
<213> ORGANISM: Artificial sequence
<220> FEATURE:
<223> OTHER INFORMATION: Primer

<400> SEQUENCE: 19
aagaatgcgg ccgctgcaga gacagtgacc ag                                   32

<210> SEQ ID NO 20
<211> LENGTH: 29
<212> TYPE: DNA
<213> ORGANISM: Artificial sequence
<220> FEATURE:
<223> OTHER INFORMATION: Primer
```

<400> SEQUENCE: 20
gatattcaga tgacccagag cccgagcag                                    29

<210> SEQ ID NO 21
<211> LENGTH: 34
<212> TYPE: DNA
<213> ORGANISM: Artificial sequence
<220> FEATURE:
<223> OTHER INFORMATION: Primer

<400> SEQUENCE: 21
aataggatcc accacctccg ctgctcacgg tcac                              34

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
ccattgacgc aaatgggcgg tagg                                         24

<210> SEQ ID NO 23
<211> LENGTH: 29
<212> TYPE: DNA
<213> ORGANISM: Artificial sequence
<220> FEATURE:
<223> OTHER INFORMATION: Primer

<400> SEQUENCE: 23
ctgctcgggc tctgggtcat ctgaatatc                                    29

<210> SEQ ID NO 24
<211> LENGTH: 38
<212> TYPE: DNA
<213> ORGANISM: Artificial sequence
<220> FEATURE:
<223> OTHER INFORMATION: Primer

<400> SEQUENCE: 24
tgctccacgc cgccaggccg gatattcaga tgacccag                          38

<210> SEQ ID NO 25
<211> LENGTH: 35
<212> TYPE: DNA
<213> ORGANISM: Artificial sequence
<220> FEATURE:
<223> OTHER INFORMATION: Primer

<400> SEQUENCE: 25
cgcggcgctg gcgtcgtggt gctgctcacg gtcac                             35

<210> SEQ ID NO 26
<211> LENGTH: 19
<212> TYPE: DNA
<213> ORGANISM: Artificial sequence
<220> FEATURE:
<223> OTHER INFORMATION: Primer

<400> SEQUENCE: 26
tgcagtagtc gccgtgaac                                               19

<210> SEQ ID NO 27

-continued

```
<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
cggcctggcg gcgtggagca                                               20

<210> SEQ ID NO 28
<211> LENGTH: 25
<212> TYPE: DNA
<213> ORGANISM: Artificial sequence
<220> FEATURE:
<223> OTHER INFORMATION: Primer

<400> SEQUENCE: 28
accacgacgc cagcgccgcg accac                                         25

<210> SEQ ID NO 29
<211> LENGTH: 48
<212> TYPE: DNA
<213> ORGANISM: Artificial sequence
<220> FEATURE:
<223> OTHER INFORMATION: Primer

<400> SEQUENCE: 29
gaggtcgacc tacgcggggg cgtctgcgct cctgctgaac ttcactct                48

<210> SEQ ID NO 30
<211> LENGTH: 39
<212> TYPE: DNA
<213> ORGANISM: Artificial sequence
<220> FEATURE:
<223> OTHER INFORMATION: Primer

<400> SEQUENCE: 30
gaggtcgacc tagcgagggg gcagggcctg catgtgaag                          39

<210> SEQ ID NO 31
<211> LENGTH: 1928
<212> TYPE: DNA
<213> ORGANISM: Artificial sequence
<220> FEATURE:
<223> OTHER INFORMATION: eGFP-F2A-Y022 scFv-Z nucleotide sequence

<400> SEQUENCE: 31
tgcagtagtc gccgtgaacg ttcttttttcg caacgggttt gccgccagaa cacaggtgtc     60
gtgacgcgga tccaggccta agcttacgcg tcctagcgct accggtcgcc accatggtga    120
gcaagggcga ggagctgttc accggggtgg tgcccatcct ggtcgagctg gacggcgacg    180
taaacggcca aagttcagc gtgtccggcg agggcgaggg cgatgccacc tacggcaagc    240
tgaccctgaa gttcatctgc accaccggca agctgcccgt gccctggccc accctcgtga    300
ccaccctgac ctacggcgtg cagtgcttca gccgctaccc cgaccacatg aagcagcacg    360
acttcttcaa gtccgccatg cccgaaggct acgtccagga gcgcaccatc ttcttcaagg    420
acgacggcaa ctacaagacc cgcgccgagg tgaagttcga gggcgacacc ctggtgaacc    480
gcatcgagct gaagggcatc gacttcaagg aggacggcaa catcctgggg cacaagctgg    540
agtacaacta aacagccac aacgtctata tcatggccga caagcagaag aacggcatca    600
aggtgaactt caagatccgc cacaacatcg aggacggcag cgtgcagctc gccgaccact    660
accagcagaa cacccccatc ggcgacggcc ccgtgctgct gcccgacaac cactacctga    720
```

```
gcacccagtc cgccctgagc aaagacccca acgagaagcg cgatcacatg gtcctgctgg      780
agttcgtgac cgccgccggg atcactctcg gcatggacga gctgtacaag tccggagtga      840
aacagacttt gaattttgac cttctgaagt tggcaggaga cgttgagtcc aaccctgggc      900
ccatggcctt accagtgacc gccttgctcc tgccgctggc cttgctgctc cacgccgcca      960
ggccggatat tcagatgacc cagagcccga gcagcctgag cgcgagcgtg ggcgaccgtg     1020
tgaccattac ctgccatgcg agccaggata ttaacgtgaa cattggctgg ctgcagcaga     1080
aaccgggcaa agcgtttaaa ggcctgattt atcatggcaa aaacctggaa gatggcgtgc     1140
cgagccgttt tagcggcagc ggcagcggca ccgattttac cctgaccatt agcagcctgc     1200
agccggaaga ttttgcgacc tattattgca atcagtatga aaatatccca ctgacatttg     1260
gccagggcac caaagtggaa attaaacgtg gtggaggcgg ttcaggcgga ggtggctctg     1320
gcggtggcgg atcggatgtg cagctggtgg aaagcggcgg cggcctggtg cagccgggcg     1380
gcagcctgcg tctgagctgc gcggtgagcg gctatagcat taccagcgat tatgcgtgga     1440
actggattcg tcaggcgccg ggcaaaggcc tggaatggct gggctatatt agctatcgtg     1500 gccgcacccca gtataacccg agcctgaaaa gccgtattag cattacccgt gataacagca     1560
aaaacacctt tttcctgcag ctgaacagcc tgcgtgcgga agataccgcg gtgtattatt     1620
gcgcgcgcat gggtaagaat tgggattact ggggccaggg cacccctggtg accgtgagca     1680 gcaccacgac gccagcgccg cgaccaccaa caccggcgcc caccatcgcg tcgcagcccc     1740
tgtccctgcg cccagaggcg tgccggccag cggcggggg cgcagtgcac acgagggggc     1800
tggacttcgc ctgtgatatc tacatctggg cgcccttggc cgggacttgt ggggtccttc     1860
tcctgtcact ggttatcacc agagtgaagt tcagcaggag cgcagacgcc cccgcgtagg     1920
tcgacctc                                                              1928
```

<210> SEQ ID NO 32
<211> LENGTH: 2231
<212> TYPE: DNA
<213> ORGANISM: Artificial sequence
<220> FEATURE:
<223> OTHER INFORMATION: eGFP-F2A-Y022 scFv-Z nucleotide sequence

<400> SEQUENCE: 32

```
tgcagtagtc gccgtgaacg ttcttttttcg caacgggttt gccgccagaa cacaggtgtc       60
gtgacgcgga tccaggccta agcttacgcg tcctagcgct accggtcgcc accatggtga      120
gcaagggcga ggagctgttc accggggtgg tgcccatcct ggtcgagctg gacggcgacg      180
taaacggcca caagttcagc gtgtccggcg agggcgaggg cgatgccacc tacggcaagc      240
tgaccctgaa gttcatctgc accaccggca agctgcccgt gccctggccc accctcgtga      300
ccaccctgac ctacggcgtg cagtgcttca gccgctaccc cgaccacatg aagcagcacg      360
acttcttcaa gtccgccatg cccgaaggct acgtccagga gcgcaccatc ttcttcaagg      420
acgacggcaa ctacaagacc cgcgccgagg tgaagttcga gggcgacacc ctggtgaacc      480
gcatcgagct gaagggcatc gacttcaagg aggacggcaa catcctgggg cacaagctgg      540
agtacaacta caacagccac aacgtctata tcatggccga caagcagaag aacggcatca      600
aggtgaactt caagatccgc cacaacatcg aggacggcag cgtgcagctc gccgaccact      660
accagcagaa cacccccatc ggcgacggcc ccgtgctgct gcccgacaac cactacctga      720
gcacccagtc cgccctgagc aaagacccca acgagaagcg cgatcacatg gtcctgctgg      780
```

```
agttcgtgac cgccgccggg atcactctcg gcatggacga gctgtacaag tccggagtga      840
aacagacttt gaattttgac cttctgaagt tggcaggaga cgttgagtcc aaccctgggc      900
ccatggcctt accagtgacc gccttgctcc tgccgctggc cttgctgctc cacgccgcca      960
ggccggatat tcagatgacc cagagcccga gcagcctgag cgcgagcgtg ggcgaccgtg     1020
tgaccattac ctgccatgcg agccaggata ttaacgtgaa cattggctgg ctgcagcaga     1080
aaccgggcaa agcgtttaaa ggcctgattt atcatggcaa aaacctggaa gatggcgtgc     1140
cgagccgttt tagcggcagc ggcagcggca ccgatttac cctgaccatt agcagcctgc      1200
agccggaaga ttttgcgacc tattattgca atcagtatga aaatatccca ctgacatttg     1260
gccagggcac caaagtggaa attaaacgtg gtggaggcgg ttcaggcgga ggtggctctg     1320
gcggtggcgg atcggatgtg cagctggtgg aaagcggcgg cggcctggtg cagccgggcg     1380
gcagcctgcg tctgagctgc gcggtgagcg gctatagcat taccagcgat tatgcgtgga     1440
actggattcg tcaggcgccg ggcaaaggcc tggaatggct gggctatatt agctatcgtg     1500 gccgcacccca gtataacccg agcctgaaaa gccgtattag cattacccgt gataacagca     1560
aaaacacctt tttcctgcag ctgaacagcc tgcgtgcgga agataccgcg gtgtattatt     1620
gcgcgcgcat gggtaagaat tgggattact ggggccaggg caccctggtg accgtgagca     1680
gcaccacgac gccagcgccg cgaccaccaa caccggcgcc caccatcgcg tcgcagcccc     1740
tgtccctgcg cccagaggcg tgccggccag cggcgggggg cgcagtgcac acgagggggc     1800
tggacttcgc ctgtgatatc tacatctggg cgcccttggc cgggacttgt ggggtccttc     1860
tcctgtcact ggttatcacc agagtgaagt tcagcaggag cgcagacgcc cccgcgtacc     1920
agcagggcca gaaccagctc tataacgagc tcaatctagg acgaagagag gagtacgatg     1980
ttttggacaa gagacgtggc cgggaccctg agatgggggg aaagccgcag agaaggaaga     2040
accctcagga aggcctgtac aatgaactgc agaaagataa gatggcggag gcctacagtg     2100
agattgggat gaaaggcgag cgccggaggg gcaaggggca cgatggcctt taccagggtc     2160
tcagtacagc caccaaggac acctacgacg cccttcacat gcaggccctg ccccctcgct     2220
aggtcgacct c                                                          2231

<210> SEQ ID NO 33
<211> LENGTH: 2357
<212> TYPE: DNA
<213> ORGANISM: Artificial sequence
<220> FEATURE:
<223> OTHER INFORMATION: eGFP-F2A-Y022 scFv-BBZ nucleotide sequence

<400> SEQUENCE: 33
tgcagtagtc gccgtgaacg ttcttttttcg caacgggttt gccgccagaa cacaggtgtc      60
gtgacgcgga tccaggccta agcttacgcg tcctagcgct accggtcgcc accatggtga     120
gcaagggcga ggagctgttc accggggtgg tgcccatcct ggtcgagctg gacggcgacg     180
taaacggcca caagttcagc gtgtccggcg agggcgaggg cgatgccacc tacggcaagc     240
tgaccctgaa gttcatctgc accaccggca agctgcccgt gccctggccc accctcgtga     300
ccaccctgac ctacggcgtg cagtgcttca gccgctaccc cgaccacatg aagcagcacg     360
acttcttcaa gtccgccatg cccgaaggct acgtccagga gcgcaccatc ttcttcaagg     420
acgacggcaa ctacaagacc cgcgccgagg tgaagttcga gggcgacacc ctggtgaacc     480
gcatcgagct gaagggcatc gacttcaagg aggacggcaa catcctgggg cacaagctgg     540
agtacaacta caacagccac aacgtctata tcatggccga caagcagaag aacggcatca     600
```

```
aggtgaactt caagatccgc cacaacatcg aggacggcag cgtgcagctc gccgaccact    660
accagcagaa caccccatc ggcgacggcc ccgtgctgct gcccgacaac cactacctga    720
gcacccagtc cgccctgagc aaagacccca cgagaagcg cgatcacatg gtcctgctgg    780
agttcgtgac cgccgccggg atcactctcg gcatggacga gctgtacaag tccggagtga    840
aacagacttt gaattttgac cttctgaagt tggcaggaga cgttgagtcc aaccctgggc    900
ccatggcctt accagtgacc gccttgctcc tgccgctggc cttgctgctc cacgccgcca    960
ggccggatat tcagatgacc cagagcccga gcagcctgag cgcgagcgtg ggcgaccgtg   1020
tgaccattac ctgccatgcg agccaggata ttaacgtgaa cattggctgg ctgcagcaga   1080
aaccgggcaa agcgtttaaa ggcctgattt atcatggcaa aaacctggaa gatggcgtgc   1140
cgagccgttt tagcggcagc ggcagcggca ccgatttac cctgaccatt agcagcctgc    1200
agccggaaga ttttgcgacc tattattgca atcagtatga aaatatccca ctgacatttg   1260
gccagggcac caaagtggaa attaaacgtg gtggaggcgg ttcaggcgga ggtggctctg   1320
gcggtggcgg atcggatgtg cagctggtgg aaagcggcgg cggcctggtg cagccgggcg   1380
gcagcctgcg tctgagctgc gcggtgagcg gctatagcat taccagcgat tatgcgtgga   1440
actggattcg tcaggcgccg ggcaaaggcc tggaatggct gggctatatt agctatcgtg   1500 gccgcacca gtataacccg agcctgaaaa gccgtattag cattacccgt gataacagca   1560
aaaacacctt tttcctgcag ctgaacagcc tgcgtgcgga agataccgcg gtgtattatt   1620
gcgcgcgcat gggtaagaat tgggattact ggggccaggg caccctggtg accgtgagca   1680
gcaccacgac gccagcgccg cgaccaccaa caccggcgcc caccatcgcg tcgcagcccc   1740
tgtccctgcg cccagaggcg tgccggccag cggcggggg cgcagtgcac acgagggggc    1800
tggacttcgc ctgtgatatc tacatctggg cgcccttggc cgggacttgt ggggtccttc   1860
tcctgtcact ggttatcacc aaacgggggca gaaagaaact cctgtatata ttcaaacaac   1920
catttatgag accagtacaa actactcaag aggaagatgg ctgtagctgc cgatttccag   1980
aagaagaaga aggaggatgt gaactgagag tgaagttcag caggagcgca gacgcccccg   2040
cgtaccagca gggccagaac cagctctata acgagctcaa tctaggacga agagaggagt   2100
acgatgtttt ggacaagaga cgtggccggg accctgagat gggggaaag ccgcagagaa   2160 ggaagaaccc tcaggaaggc ctgtacaatg aactgcagaa agataagatg gcggaggcct   2220
acagtgagat tgggatgaaa ggcgagcgcc ggagggcaa ggggcacgat ggcctttacc   2280
agggtctcag tacagccacc aaggacacct acgacgccct tcacatgcag gccctgcccc   2340
ctcgctaggt cgacctc                                                   2357
```

<210> SEQ ID NO 34
<211> LENGTH: 2372
<212> TYPE: DNA
<213> ORGANISM: Artificial sequence
<220> FEATURE:
<223> OTHER INFORMATION: eGFP-F2A-Y022 scFv-28Z nucleotide sequence

<400> SEQUENCE: 34

```
tgcagtagtc gccgtgaacg ttcttttttcg caacgggttt gccgccagaa cacaggtgtc     60
gtgacgcgga tccaggccta agcttacgcg tcctagcgct accggtcgcc accatggtga    120
gcaagggcga ggagctgttc accggggtgg tgcccatcct ggtcgagctg gacggcgacg    180
taaacggcca caagttcagc gtgtccggcg agggcgaggg cgatgccacc tacggcaagc    240
```

```
tgaccctgaa gttcatctgc accaccggca agctgcccgt gccctggccc accctcgtga    300
ccacccctgac ctacggcgtg cagtgcttca gccgctaccc cgaccacatg aagcagcacg   360
acttcttcaa gtccgccatg cccgaaggct acgtccagga gcgcaccatc ttcttcaagg   420
acgacggcaa ctacaagacc cgcgccgagg tgaagttcga gggcgacacc ctggtgaacc   480
gcatcgagct gaagggcatc gacttcaagg aggacggcaa catcctgggg cacaagctgg   540
agtacaacta caacagccac aacgtctata tcatggccga caagcagaag aacggcatca   600
aggtgaactt caagatccgc cacaacatcg aggacggcag cgtgcagctc gccgaccact   660
accagcagaa cacccccatc ggcgacggcc ccgtgctgct gcccgacaac cactacctga   720
gcacccagtc cgccctgagc aaagacccca acgagaagcg cgatcacatg gtcctgctgg   780
agttcgtgac cgccgccggg atcactctcg gcatggacga gctgtacaag tccggagtga   840
aacagacttt gaattttgac cttctgaagt tggcaggaga cgttgagtcc aaccctgggc   900
ccatggcctt accagtgacc gccttgctcc tgccgctggc cttgctgctc cacgccgcca   960
ggccggatat tcagatgacc cagagcccga gcagcctgag cgcgagcgtg ggcgaccgtg   1020
tgaccattac ctgccatgcg agccaggata ttaacgtgaa cattggctgg ctgcagcaga  1080
aaccgggcaa agcgttttaaa ggcctgattt atcatggcaa aaacctggaa gatggcgtgc  1140
cgagccgttt tagcggcagc ggcagcggca ccgattttac cctgaccatt agcagcctgc  1200
agccggaaga ttttgcgacc tattattgca atcagtatga aaatatccca ctgacatttg  1260
gccagggcac caaagtggaa attaaacgtg gtggaggcgg ttcaggcgga ggtggctctg  1320
gcggtggcgg atcggatgtg cagctggtgg aaagcggcgg cggcctggtg cagccgggcg  1380
gcagcctgcg tctgagctgc gcggtgagcg gctatagcat taccagcgat tatgcgtgga  1440
actggattcg tcaggcgccg ggcaaaggcc tggaatggct gggctatatt agctatcgtg  1500
gccgcacccca gtataacccg agcctgaaaa gccgtattag cattacccgt gataacagca  1560
aaaacaccctt tttcctgcag ctgaacagcc tgcgtgcgga agataccgcg gtgtattatt  1620
gcgcgcgcat gggtaagaat tgggattact ggggccaggg caccctggtg accgtgagca  1680
gcaccacgac gccagcgccg cgaccaccaa caccggcgcc caccatcgcg tcgcagcccc  1740
tgtccctgcg cccagaggcg tgccggccag cggcgggggg cgcagtgcac acgaggggggc  1800
tggacttcgc ctgtgatttt tgggtgctgg tggtggttgg tggagtcctg gcttgctata  1860
gcttgctagt aacagtggcc tttattattt tctgggtgag gagtaagagg agcaggctcc  1920
tgcacagtga ctacatgaac atgactcccc gccgccccgg gccaacccgc aagcattacc  1980
agccctatgc cccaccacgc gacttcgcag cctatcgctc cagagtgaag ttcagcagga  2040
gcgcagacgc ccccgcgtac cagcagggcc agaaccagct ctataacgag ctcaatctag  2100
gacgaagaga ggagtacgat gttttggaca agagacgtgg ccgggaccct gagatggggg  2160
gaaagccgca gagaaggaag aaccctcagg aaggcctgta caatgaactg cagaaagata  2220
agatggcgga ggcctacagt gagattggga tgaaaggcga gcgccggagg gcaagggggc  2280
acgatggcct ttaccagggt ctcagtacag ccaccaagga cacctacgac gcccttcaca  2340
tgcaggccct gccccctcgc taggtcgacc tc                                2372
```

<210> SEQ ID NO 35
<211> LENGTH: 2498
<212> TYPE: DNA
<213> ORGANISM: Artificial sequence
<220> FEATURE:
<223> OTHER INFORMATION: eGFP-F2A-Y022 scFv-28BBZ nucleotide sequence

<400> SEQUENCE: 35

```
tgcagtagtc gccgtgaacg ttcttttcg caacgggttt gccgccagaa cacaggtgtc      60
gtgacgcgga tccaggccta agcttacgcg tcctagcgct accggtcgcc accatggtga    120
gcaagggcga ggagctgttc accggggtgg tgcccatcct ggtcgagctg gacggcgacg    180
taaacggcca caagttcagc gtgtccggcg agggcgaggg cgatgccacc tacggcaagc    240
tgaccctgaa gttcatctgc accaccggca agctgcccgt gccctggccc accctcgtga    300
ccaccctgac ctacggcgtg cagtgcttca gccgctaccc cgaccacatg aagcagcacg    360
acttcttcaa gtccgccatg cccgaaggct acgtccagga gcgcaccatc ttcttcaagg    420
acgacggcaa ctacaagacc cgcgccgagg tgaagttcga gggcgacacc ctggtgaacc    480
gcatcgagct gaagggcatc gacttcaagg aggacggcaa catcctgggg cacaagctgg    540
agtacaacta caacagccac aacgtctata tcatggccga caagcagaag aacggcatca    600
aggtgaactt caagatccgc cacaacatcg aggacggcag cgtgcagctc gccgaccact    660
accagcagaa cacccccatc ggcgacggcc ccgtgctgct gcccgacaac cactacctga    720
gcacccagtc cgccctgagc aaagacccca acgagaagcg cgatcacatg gtcctgctgg    780
agttcgtgac cgccgccggg atcactctcg gcatggacga gctgtacaag tccggagtga    840
aacagacttt gaattttgac cttctgaagt tggcaggaga cgttgagtcc aaccctgggc    900
ccatggcctt accagtgacc gccttgctcc tgccgctggc cttgctgctc cacgccgcca    960
ggccggatat tcagatgacc cagagcccga gcagcctgag cgcgagcgtg ggcgaccgtg   1020
tgaccattac ctgccatgcg agccaggata ttaacgtgaa cattggctgg ctgcagcaga   1080
aaccgggcaa agcgttaaa ggcctgattt atcatggcaa aaacctggaa gatggcgtgc   1140
cgagccgttt tagcggcagc ggcagcggca ccgattttac cctgaccatt agcagcctgc   1200
agccggaaga ttttgcgacc tattattgca atcagtatga aatatccca ctgacatttg   1260
gccagggcac caaagtggaa attaaacgtg gtggaggcgg ttcaggcgga ggtggctctg   1320
gcggtggcgg atcggatgtg cagctggtgg aaagcggcgg cggcctggtg cagccgggcg   1380
gcagcctgcg tctgagctgc gcggtgagcg gctatagcat taccagcgat tatgcgtgga   1440
actggattcg tcaggcgccc ggcaaaggcc tggaatggct gggctatatt agctatcgtg   1500
gccgcaccca gtataacccg agcctgaaaa gccgtattag cattacccgt gataacagca   1560
aaaacacctt tttcctgcag ctgaacagcc tgcgtgcgga agataccgcg gtgtattatt   1620
gcgcgcgcat gggtaagaat tgggattact ggggccaggg caccctggtg accgtgagca   1680
gcaccacgac gccagcgccg cgaccaccaa caccggcgcc caccatcgcg tcgcagcccc   1740
tgtccctgcg cccagaggcg tgccggccag cggcgggggg cgcagtgcac acgagggggc   1800
tggacttcgc ctgtgatttt tgggtgctgg tggtggttgg tggagtcctg gcttgctata   1860
gcttgctagt aacagtggcc tttattattt tctgggtgag gagtaagagg agcaggctcc   1920
tgcacagtga ctacatgaac atgactcccc gccgccccgg ccaacccgc aagcattacc   1980
agccctatgc cccaccacgc gacttcgcag cctatcgctc caacggggc agaaagaaac   2040
tcctgtatat attcaaacaa ccatttatga gaccagtaca aactactcaa gaggaagatg   2100
gctgtagctg ccgatttcca gaagaagaag aaggaggatg tgaactgaga gtgaagttca   2160
gcaggagcgc agacgccccc gcgtaccagc agggccagaa ccagctctat aacgagctca   2220
atctaggacg aagagaggag tacgatgttt tggacaagag acgtggccgg gaccctgaga   2280
```

```
tgggggggaaa gccgcagaga aggaagaacc ctcaggaagg cctgtacaat gaactgcaga      2340
aagataagat ggcggaggcc tacagtgaga ttgggatgaa aggcgagcgc cggaggggca      2400
aggggcacga tggcctttac cagggtctca gtacagccac caaggacacc tacgacgccc      2460
ttcacatgca ggccctgccc cctcgctagg tcgacctc                              2498
```

<210> SEQ ID NO 36
<211> LENGTH: 601
<212> TYPE: PRT
<213> ORGANISM: Artificial sequence
<220> FEATURE:
<223> OTHER INFORMATION: eGFP-F2A-Y022 scFv-Z amino acid sequence

<400> SEQUENCE: 36

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Asp Ile Gln Met
        275                 280                 285

Thr Gln Ser Pro Ser Ser Leu Ser Ala Ser Val Gly Asp Arg Val Thr
290                 295                 300

Ile Thr Cys His Ala Ser Gln Asp Ile Asn Val Asn Ile Gly Trp Leu
305                 310                 315                 320

Gln Gln Lys Pro Gly Lys Ala Phe Lys Gly Leu Ile Tyr His Gly Lys
```

Asn Leu Glu Asp Gly Val Pro Ser Arg Phe Ser Gly Ser Gly
            325                 330                 335
Thr Asp Phe Thr Leu Thr Ile Ser Ser Leu Gln Pro Glu Asp Phe Ala
        340                 345                 350
Thr Tyr Tyr Cys Asn Gln Tyr Glu Asn Ile Pro Leu Thr Phe Gly Gln
    355                 360                 365
Gly Thr Lys Val Glu Ile Lys Arg Gly Gly Gly Ser Gly Gly Gly
370                 375                 380
Gly Ser Gly Gly Gly Gly Ser Asp Val Gln Leu Val Glu Ser Gly Gly
385                 390                 395                 400
Gly Leu Val Gln Pro Gly Gly Ser Leu Arg Leu Ser Cys Ala Val Ser
            405                 410                 415
Gly Tyr Ser Ile Thr Ser Asp Tyr Ala Trp Asn Trp Ile Arg Gln Ala
        420                 425                 430
Pro Gly Lys Gly Leu Glu Trp Leu Gly Tyr Ile Ser Tyr Arg Gly Arg
    435                 440                 445
Thr Gln Tyr Asn Pro Ser Leu Lys Ser Arg Ile Ser Ile Thr Arg Asp
450                 455                 460
Asn Ser Lys Asn Thr Phe Phe Leu Gln Leu Asn Ser Leu Arg Ala Glu
465                 470                 475                 480
Asp Thr Ala Val Tyr Tyr Cys Ala Arg Met Gly Lys Asn Trp Asp Tyr
            485                 490                 495
Trp Gly Gln Gly Thr Leu Val Thr Val Ser Ser Thr Thr Pro Ala
        500                 505                 510
Pro Arg Pro Pro Thr Pro Ala Pro Thr Ile Ala Ser Gln Pro Leu Ser
    515                 520                 525
Leu Arg Pro Glu Ala Cys Arg Pro Ala Ala Gly Gly Ala Val His Thr
530                 535                 540
Arg Gly Leu Asp Phe Ala Cys Asp Ile Tyr Ile Trp Ala Pro Leu Ala
545                 550                 555                 560
Gly Thr Cys Gly Val Leu Leu Leu Ser Leu Val Ile Thr Arg Val Lys
            565                 570                 575
Phe Ser Arg Ser Ala Asp Ala Pro Ala
        580                 585                 590

<210> SEQ ID NO 37
<211> LENGTH: 702
<212> TYPE: PRT
<213> ORGANISM: Artificial sequence
<220> FEATURE:
<223> OTHER INFORMATION: eGFP-F2A-Y022 scFv-Z amino acid sequence

<400> SEQUENCE: 37

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu

-continued

```
                85                  90                  95
Arg Thr Ile Phe Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Asp Ile Gln Met
        275                 280                 285

Thr Gln Ser Pro Ser Ser Leu Ser Ala Ser Val Gly Asp Arg Val Thr
    290                 295                 300

Ile Thr Cys His Ala Ser Gln Asp Ile Asn Val Asn Ile Gly Trp Leu
305                 310                 315                 320

Gln Gln Lys Pro Gly Lys Ala Phe Lys Gly Leu Ile Tyr His Gly Lys
                325                 330                 335

Asn Leu Glu Asp Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Asn Gln Tyr Glu Asn Ile Pro Leu Thr Phe Gly Gln
    370                 375                 380

Gly Thr Lys Val Glu Ile Lys Arg Gly Gly Gly Ser Gly Gly Gly Gly
385                 390                 395                 400

Gly Ser Gly Gly Gly Ser Asp Val Gln Leu Val Glu Ser Gly Gly
                405                 410                 415

Gly Leu Val Gln Pro Gly Gly Ser Leu Arg Leu Ser Cys Ala Val Ser
            420                 425                 430

Gly Tyr Ser Ile Thr Ser Asp Tyr Ala Trp Asn Trp Ile Arg Gln Ala
        435                 440                 445

Pro Gly Lys Gly Leu Glu Trp Leu Gly Tyr Ile Ser Tyr Arg Gly Arg
    450                 455                 460

Thr Gln Tyr Asn Pro Ser Leu Lys Ser Arg Ile Ser Ile Thr Arg Asp
465                 470                 475                 480

Asn Ser Lys Asn Thr Phe Phe Leu Gln Leu Asn Ser Leu Arg Ala Glu
                485                 490                 495

Asp Thr Ala Val Tyr Tyr Cys Ala Arg Met Gly Lys Asn Trp Asp Tyr
            500                 505                 510
```

-continued

Trp Gly Gln Gly Thr Leu Val Thr Val Ser Ser Thr Thr Thr Pro Ala
            515                 520                 525

Pro Arg Pro Pro Thr Pro Ala Pro Thr Ile Ala Ser Gln Pro Leu Ser
530                 535                 540

Leu Arg Pro Glu Ala Cys Arg Pro Ala Ala Gly Gly Ala Val His Thr
545                 550                 555                 560

Arg Gly Leu Asp Phe Ala Cys Asp Ile Tyr Ile Trp Ala Pro Leu Ala
            565                 570                 575

Gly Thr Cys Gly Val Leu Leu Leu Ser Leu Val Ile Thr Arg Val Lys
            580                 585                 590

Phe Ser Arg Ser Ala Asp Ala Pro Ala Tyr Gln Gln Gly Gln Asn Gln
        595                 600                 605

Leu Tyr Asn Glu Leu Asn Leu Gly Arg Arg Glu Glu Tyr Asp Val Leu
        610                 615                 620

Asp Lys Arg Arg Gly Arg Asp Pro Glu Met Gly Gly Lys Pro Gln Arg
625                 630                 635                 640

Arg Lys Asn Pro Gln Glu Gly Leu Tyr Asn Glu Leu Gln Lys Asp Lys
                645                 650                 655

Met Ala Glu Ala Tyr Ser Glu Ile Gly Met Lys Gly Glu Arg Arg Arg
            660                 665                 670

Gly Lys Gly His Asp Gly Leu Tyr Gln Gly Leu Ser Thr Ala Thr Lys
            675                 680                 685

Asp Thr Tyr Asp Ala Leu His Met Gln Ala Leu Pro Pro Arg
690                 695                 700

<210> SEQ ID NO 38
<211> LENGTH: 744
<212> TYPE: PRT
<213> ORGANISM: Artificial sequence
<220> FEATURE:
<223> OTHER INFORMATION: eGFP-F2A-Y022 scFv-BBZ amino acid sequence

<400> SEQUENCE: 38

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

```
Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Asp Ile Gln Met
        275                 280                 285

Thr Gln Ser Pro Ser Ser Leu Ser Ala Ser Val Gly Asp Arg Val Thr
    290                 295                 300

Ile Thr Cys His Ala Ser Gln Asp Ile Asn Val Asn Ile Gly Trp Leu
305                 310                 315                 320

Gln Gln Lys Pro Gly Lys Ala Phe Lys Gly Leu Ile Tyr His Gly Lys
                325                 330                 335

Asn Leu Glu Asp Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Asn Gln Tyr Glu Asn Ile Pro Leu Thr Phe Gly Gln
    370                 375                 380

Gly Thr Lys Val Glu Ile Lys Arg Gly Gly Gly Ser Gly Gly Gly
385                 390                 395                 400

Gly Ser Gly Gly Gly Gly Ser Asp Val Gln Leu Val Glu Ser Gly Gly
                405                 410                 415

Gly Leu Val Gln Pro Gly Gly Ser Leu Arg Leu Ser Cys Ala Val Ser
            420                 425                 430

Gly Tyr Ser Ile Thr Ser Asp Tyr Ala Trp Asn Trp Ile Arg Gln Ala
        435                 440                 445

Pro Gly Lys Gly Leu Glu Trp Leu Gly Tyr Ile Ser Tyr Arg Gly Arg
    450                 455                 460

Thr Gln Tyr Asn Pro Ser Leu Lys Ser Arg Ile Ser Ile Thr Arg Asp
465                 470                 475                 480

Asn Ser Lys Asn Thr Phe Phe Leu Gln Leu Asn Ser Leu Arg Ala Glu
                485                 490                 495

Asp Thr Ala Val Tyr Tyr Cys Ala Arg Met Gly Lys Asn Trp Asp Tyr
            500                 505                 510

Trp Gly Gln Gly Thr Leu Val Thr Val Ser Ser Thr Thr Thr Pro Ala
        515                 520                 525

Pro Arg Pro Pro Thr Pro Ala Pro Thr Ile Ala Ser Gln Pro Leu Ser
    530                 535                 540

Leu Arg Pro Glu Ala Cys Arg Pro Ala Ala Gly Gly Ala Val His Thr
545                 550                 555                 560

Arg Gly Leu Asp Phe Ala Cys Asp Ile Tyr Ile Trp Ala Pro Leu Ala
                565                 570                 575

Gly Thr Cys Gly Val Leu Leu Leu Ser Leu Val Ile Thr Lys Arg Gly
            580                 585                 590
```

```
Arg Lys Lys Leu Leu Tyr Ile Phe Lys Gln Pro Phe Met Arg Pro Val
            595                 600                 605

Gln Thr Thr Gln Glu Glu Asp Gly Cys Ser Cys Arg Phe Pro Glu Glu
    610                 615                 620

Glu Glu Gly Gly Cys Glu Leu Arg Val Lys Phe Ser Arg Ser Ala Asp
625                 630                 635                 640

Ala Pro Ala Tyr Gln Gln Gly Gln Asn Gln Leu Tyr Asn Glu Leu Asn
            645                 650                 655

Leu Gly Arg Arg Glu Glu Tyr Asp Val Leu Asp Lys Arg Arg Gly Arg
            660                 665                 670

Asp Pro Glu Met Gly Gly Lys Pro Gln Arg Arg Lys Asn Pro Gln Glu
            675                 680                 685

Gly Leu Tyr Asn Glu Leu Gln Lys Asp Lys Met Ala Glu Ala Tyr Ser
            690                 695                 700

Glu Ile Gly Met Lys Gly Glu Arg Arg Arg Gly Lys Gly His Asp Gly
705                 710                 715                 720

Leu Tyr Gln Gly Leu Ser Thr Ala Thr Lys Asp Thr Tyr Asp Ala Leu
            725                 730                 735

His Met Gln Ala Leu Pro Pro Arg
            740

<210> SEQ ID NO 39
<211> LENGTH: 749
<212> TYPE: PRT
<213> ORGANISM: Artificial sequence
<220> FEATURE:
<223> OTHER INFORMATION: eGFP-F2A-Y022 scFv-28Z amino acid sequence

<400> SEQUENCE: 39

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

```
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys Ser
225                 230                 235                 240
Gly Val Lys Gln Thr Leu Asn Phe Asp Leu Leu Lys Leu Ala Gly Asp
                245                 250                 255
Val Glu Ser Asn Pro Gly Pro Met Ala Leu Pro Val Thr Ala Leu Leu
            260                 265                 270
Leu Pro Leu Ala Leu Leu Leu His Ala Ala Arg Pro Asp Ile Gln Met
        275                 280                 285
Thr Gln Ser Pro Ser Ser Leu Ser Ala Ser Val Gly Asp Arg Val Thr
    290                 295                 300
Ile Thr Cys His Ala Ser Gln Asp Ile Asn Val Asn Ile Gly Trp Leu
305                 310                 315                 320
Gln Gln Lys Pro Gly Lys Ala Phe Lys Gly Leu Ile Tyr His Gly Lys
                325                 330                 335
Asn Leu Glu Asp Gly Val Pro Ser Arg Phe Ser Gly Ser Gly Ser Gly
            340                 345                 350
Thr Asp Phe Thr Leu Thr Ile Ser Ser Leu Gln Pro Glu Asp Phe Ala
        355                 360                 365
Thr Tyr Tyr Cys Asn Gln Tyr Glu Asn Ile Pro Leu Thr Phe Gly Gln
    370                 375                 380
Gly Thr Lys Val Glu Ile Lys Arg Gly Gly Gly Gly Ser Gly Gly Gly
385                 390                 395                 400
Gly Ser Gly Gly Gly Gly Ser Asp Val Gln Leu Val Glu Ser Gly Gly
                405                 410                 415
Gly Leu Val Gln Pro Gly Gly Ser Leu Arg Leu Ser Cys Ala Val Ser
            420                 425                 430
Gly Tyr Ser Ile Thr Ser Asp Tyr Ala Trp Asn Trp Ile Arg Gln Ala
        435                 440                 445
Pro Gly Lys Gly Leu Glu Trp Leu Gly Tyr Ile Ser Tyr Arg Gly Arg
    450                 455                 460
Thr Gln Tyr Asn Pro Ser Leu Lys Ser Arg Ile Ser Ile Thr Arg Asp
465                 470                 475                 480
Asn Ser Lys Asn Thr Phe Phe Leu Gln Leu Asn Ser Leu Arg Ala Glu
                485                 490                 495
Asp Thr Ala Val Tyr Tyr Cys Ala Arg Met Gly Lys Asn Trp Asp Tyr
            500                 505                 510
Trp Gly Gln Gly Thr Leu Val Thr Val Ser Ser Thr Thr Thr Pro Ala
        515                 520                 525
Pro Arg Pro Pro Thr Pro Ala Pro Thr Ile Ala Ser Gln Pro Leu Ser
    530                 535                 540
Leu Arg Pro Glu Ala Cys Arg Pro Ala Ala Gly Gly Ala Val His Thr
545                 550                 555                 560
Arg Gly Leu Asp Phe Ala Cys Asp Phe Trp Val Leu Val Val Val Gly
                565                 570                 575
Gly Val Leu Ala Cys Tyr Ser Leu Leu Val Thr Val Ala Phe Ile Ile
            580                 585                 590
Phe Trp Val Arg Ser Lys Arg Ser Arg Leu Leu His Ser Asp Tyr Met
        595                 600                 605
Asn Met Thr Pro Arg Arg Pro Gly Pro Thr Arg Lys His Tyr Gln Pro
    610                 615                 620
Tyr Ala Pro Pro Arg Asp Phe Ala Ala Tyr Arg Ser Arg Val Lys Phe
```

```
625                 630                 635                 640
Ser Arg Ser Ala Asp Ala Pro Ala Tyr Gln Gln Gly Gln Asn Gln Leu
                645                 650                 655

Tyr Asn Glu Leu Asn Leu Gly Arg Arg Glu Glu Tyr Asp Val Leu Asp
                660                 665                 670

Lys Arg Arg Gly Arg Asp Pro Glu Met Gly Gly Lys Pro Gln Arg Arg
                675                 680                 685

Lys Asn Pro Gln Glu Gly Leu Tyr Asn Glu Leu Gln Lys Asp Lys Met
                690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
                725                 730                 735

Thr Tyr Asp Ala Leu His Met Gln Ala Leu Pro Pro Arg
                740                 745

<210> SEQ ID NO 40
<211> LENGTH: 791
<212> TYPE: PRT
<213> ORGANISM: Artificial sequence
<220> FEATURE:
<223> OTHER INFORMATION: eGFP-F2A-Y022 scFv-28BBZ amino acid sequence

<400> SEQUENCE: 40

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
                35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65              70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
```

```
                245                 250                 255
Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Asp Ile Gln Met
        275                 280                 285

Thr Gln Ser Pro Ser Ser Leu Ser Ala Ser Val Gly Asp Arg Val Thr
    290                 295                 300

Ile Thr Cys His Ala Ser Gln Asp Ile Asn Val Asn Ile Gly Trp Leu
305                 310                 315                 320

Gln Gln Lys Pro Gly Lys Ala Phe Lys Gly Leu Ile Tyr His Gly Lys
                325                 330                 335

Asn Leu Glu Asp Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Asn Gln Tyr Glu Asn Ile Pro Leu Thr Phe Gly Gln
    370                 375                 380

Gly Thr Lys Val Glu Ile Lys Arg Gly Gly Gly Ser Gly Gly Gly
385                 390                 395                 400

Gly Ser Gly Gly Gly Ser Asp Val Gln Leu Val Glu Ser Gly Gly
                405                 410                 415

Gly Leu Val Gln Pro Gly Gly Ser Leu Arg Leu Ser Cys Ala Val Ser
            420                 425                 430

Gly Tyr Ser Ile Thr Ser Asp Tyr Ala Trp Asn Trp Ile Arg Gln Ala
        435                 440                 445

Pro Gly Lys Gly Leu Glu Trp Leu Gly Tyr Ile Ser Tyr Arg Gly Arg
    450                 455                 460

Thr Gln Tyr Asn Pro Ser Leu Lys Ser Arg Ile Ser Ile Thr Arg Asp
465                 470                 475                 480

Asn Ser Lys Asn Thr Phe Phe Leu Gln Leu Asn Ser Leu Arg Ala Glu
                485                 490                 495

Asp Thr Ala Val Tyr Tyr Cys Ala Arg Met Gly Lys Asn Trp Asp Tyr
            500                 505                 510

Trp Gly Gln Gly Thr Leu Val Thr Val Ser Ser Thr Thr Pro Ala
        515                 520                 525

Pro Arg Pro Pro Thr Pro Ala Pro Thr Ile Ala Ser Gln Pro Leu Ser
    530                 535                 540

Leu Arg Pro Glu Ala Cys Arg Pro Ala Ala Gly Gly Ala Val His Thr
545                 550                 555                 560

Arg Gly Leu Asp Phe Ala Cys Asp Phe Trp Val Leu Val Val Val Gly
                565                 570                 575

Gly Val Leu Ala Cys Tyr Ser Leu Leu Val Thr Val Ala Phe Ile Ile
            580                 585                 590

Phe Trp Val Arg Ser Lys Arg Ser Arg Leu Leu His Ser Asp Tyr Met
        595                 600                 605

Asn Met Thr Pro Arg Arg Pro Gly Pro Thr Arg Lys His Tyr Gln Pro
    610                 615                 620

Tyr Ala Pro Pro Arg Asp Phe Ala Ala Tyr Arg Ser Lys Arg Gly Arg
625                 630                 635                 640

Lys Lys Leu Leu Tyr Ile Phe Lys Gln Pro Phe Met Arg Pro Val Gln
                645                 650                 655

Thr Thr Gln Glu Glu Asp Gly Cys Ser Cys Arg Phe Pro Glu Glu Glu
            660                 665                 670
```

Glu Gly Gly Cys Glu Leu Arg Val Lys Phe Ser Arg Ser Ala Asp Ala
            675                 680                 685

Pro Ala Tyr Gln Gln Gly Gln Asn Gln Leu Tyr Asn Glu Leu Asn Leu
    690                 695                 700

Gly Arg Arg Glu Glu Tyr Asp Val Leu Asp Lys Arg Arg Gly Arg Asp
705                 710                 715                 720

Pro Glu Met Gly Gly Lys Pro Gln Arg Arg Lys Asn Pro Gln Glu Gly
                725                 730                 735

Leu Tyr Asn Glu Leu Gln Lys Asp Lys Met Ala Glu Ala Tyr Ser Glu
            740                 745                 750

Ile Gly Met Lys Gly Glu Arg Arg Arg Gly Lys Gly His Asp Gly Leu
        755                 760                 765

Tyr Gln Gly Leu Ser Thr Ala Thr Lys Asp Thr Tyr Asp Ala Leu His
    770                 775                 780

Met Gln Ala Leu Pro Pro Arg
785                 790

<210> SEQ ID NO 41
<211> LENGTH: 11
<212> TYPE: PRT
<213> ORGANISM: Artificial sequence
<220> FEATURE:
<223> OTHER INFORMATION: Y022 light chain CDR1

<400> SEQUENCE: 41

His Ala Ser Gln Asp Ile Asn Val Asn Ile Gly
1               5                   10

<210> SEQ ID NO 42
<211> LENGTH: 7
<212> TYPE: PRT
<213> ORGANISM: Artificial sequence
<220> FEATURE:
<223> OTHER INFORMATION: Y022 light chainCDR2

<400> SEQUENCE: 42

His Gly Lys Asn Leu Glu Asp
1               5

<210> SEQ ID NO 43
<211> LENGTH: 9
<212> TYPE: PRT
<213> ORGANISM: Artificial sequence
<220> FEATURE:
<223> OTHER INFORMATION: Y022 light chain CDR3

<400> SEQUENCE: 43

Asn Gln Tyr Glu Asn Ile Pro Leu Thr
1               5

<210> SEQ ID NO 44
<211> LENGTH: 11
<212> TYPE: PRT
<213> ORGANISM: Artificial sequence
<220> FEATURE:
<223> OTHER INFORMATION: Y022 heavy chain CDR1

<400> SEQUENCE: 44

Gly Tyr Ser Ile Thr Ser Asp Tyr Ala Trp Asn
1               5                   10

<210> SEQ ID NO 45

```
<211> LENGTH: 16
<212> TYPE: PRT
<213> ORGANISM: Artificial sequence
<220> FEATURE:
<223> OTHER INFORMATION: Y022 heavy chain CDR2

<400> SEQUENCE: 45

Tyr Ile Ser Tyr Arg Gly Arg Thr Gln Tyr Asn Pro Ser Leu Lys Ser
1               5                   10                  15

<210> SEQ ID NO 46
<211> LENGTH: 7
<212> TYPE: PRT
<213> ORGANISM: Artificial sequence
<220> FEATURE:
<223> OTHER INFORMATION: Y022 heavy chain CDR3

<400> SEQUENCE: 46

Met Gly Lys Asn Trp Asp Tyr
1               5

<210> SEQ ID NO 47
<211> LENGTH: 11
<212> TYPE: PRT
<213> ORGANISM: Artificial sequence
<220> FEATURE:
<223> OTHER INFORMATION: M14 light chain CDR1 amino acid sequence

<400> SEQUENCE: 47

His Ala Ser Gln Asp Ile Asn Ser Asn Ile Gly
1               5                   10

<210> SEQ ID NO 48
<211> LENGTH: 9
<212> TYPE: PRT
<213> ORGANISM: Artificial sequence
<220> FEATURE:
<223> OTHER INFORMATION: M14 light chain CDR3 amino acid sequence

<400> SEQUENCE: 48

Asn Gln Tyr Glu Asn Asn Pro Ile Thr
1               5

<210> SEQ ID NO 49
<211> LENGTH: 16
<212> TYPE: PRT
<213> ORGANISM: Artificial sequence
<220> FEATURE:
<223> OTHER INFORMATION: M14 heavy chain CDR2

<400> SEQUENCE: 49

Tyr Ile Ser Tyr Arg Gly Arg Thr Asn Tyr Asn Pro Ser Leu Lys Ser
1               5                   10                  15

<210> SEQ ID NO 50
<211> LENGTH: 7
<212> TYPE: PRT
<213> ORGANISM: Artificial sequence
<220> FEATURE:
<223> OTHER INFORMATION: M14 heavy chain CDR3

<400> SEQUENCE: 50

Leu Gly Arg Gly Phe Arg Tyr
1               5

<210> SEQ ID NO 51
<211> LENGTH: 16
```

```
<212> TYPE: PRT
<213> ORGANISM: Artificial sequence
<220> FEATURE:
<223> OTHER INFORMATION: M15 heavy chain CDR2

<400> SEQUENCE: 51

Tyr Ile Ser Tyr Arg Gly Arg Thr Ser Tyr Asn Pro Ser Leu Lys Ser
1               5                   10                  15

<210> SEQ ID NO 52
<211> LENGTH: 16
<212> TYPE: PRT
<213> ORGANISM: Artificial sequence
<220> FEATURE:
<223> OTHER INFORMATION: M25 heavy chain CDR2

<400> SEQUENCE: 52

Tyr Ile Ser Tyr Arg Gly Arg Thr Arg Tyr Asn Pro Ser Leu Lys Ser
1               5                   10                  15

<210> SEQ ID NO 53
<211> LENGTH: 7
<212> TYPE: PRT
<213> ORGANISM: Artificial sequence
<220> FEATURE:
<223> OTHER INFORMATION: S7 light chain CDR2

<400> SEQUENCE: 53

His Gly Thr Asn Leu Glu Asp
1               5

<210> SEQ ID NO 54
<211> LENGTH: 9
<212> TYPE: PRT
<213> ORGANISM: Artificial sequence
<220> FEATURE:
<223> OTHER INFORMATION: S7 light chain CDR3

<400> SEQUENCE: 54

Asn Gln Tyr Glu Asn Asn Pro Ile Thr
1               5

<210> SEQ ID NO 55
<211> LENGTH: 11
<212> TYPE: PRT
<213> ORGANISM: Artificial sequence
<220> FEATURE:
<223> OTHER INFORMATION: S17 light chain CDR1

<400> SEQUENCE: 55

His Ala Ser Gln Asp Ile Asn Thr Asn Ile Gly
1               5                   10

<210> SEQ ID NO 56
<211> LENGTH: 9
<212> TYPE: PRT
<213> ORGANISM: Artificial sequence
<220> FEATURE:
<223> OTHER INFORMATION: S17 light chain CDR3

<400> SEQUENCE: 56

Asn Gln Tyr Glu Asn Asn Pro Leu Thr
1               5

<210> SEQ ID NO 57
<211> LENGTH: 9
<212> TYPE: PRT
```

<213> ORGANISM: Artificial sequence
<220> FEATURE:
<223> OTHER INFORMATION: S23 light chain CDR3

<400> SEQUENCE: 57

Asn Gln Tyr Glu Asn Phe Pro Leu Thr
1               5

<210> SEQ ID NO 58
<211> LENGTH: 717
<212> TYPE: DNA
<213> ORGANISM: Artificial sequence
<220> FEATURE:
<223> OTHER INFORMATION: nucleotide sequence of single chain antibody
      M14

<400> SEQUENCE: 58

```
gatattcaga tgacccagag cccgagcagc ctgagcgcga gcgtgggcga ccgtgtgacc    60
attacctgcc atgcgagcca ggatattaac agcaacattg gctggctgca gcagaaaccg   120
ggcaaagcgt ttaaaggcct gatttatcat ggcaaaaacc tggaagatgg cgtgccgagc   180
cgttttagcg gcagcggcag cggcaccgat tttaccctga ccattagcag cctgcagccg   240
gaagattttg cgacctatta ttgcaatcag tatgaaaata cccaattac atttggccag   300 ggcaccaaag tggaaattaa acgtggtgga ggcggttcag gcggaggtgg ctctggcggt   360
ggcggatcgg atgtgcagct ggtggaaagc ggcggcggcc tggtgcagcc gggcggcagc   420
ctgcgtctga gctgcgcggt gagcggctat agcattacca gcgattatgc gtggaactgg   480
attcgtcagg cgccgggcaa aggcctggaa tggctgggct atattagcta tcgtggccgc   540
accaactata cccgagcct gaaaagccgt attagcatta cccgtgataa cagcaaaaac   600 accttttttcc tgcagctgaa cagcctgcgt gcggaagata ccgcggtgta ttattgcgcg   660
cgcctgggac gcggcttccg ctactgggc cagggcaccc tggtgaccgt gagcagc       717
```

<210> SEQ ID NO 59
<211> LENGTH: 239
<212> TYPE: PRT
<213> ORGANISM: Artificial sequence
<220> FEATURE:
<223> OTHER INFORMATION: amino acid sequence of single chain antibody
      M14

<400> SEQUENCE: 59

Asp Ile Gln Met Thr Gln Ser Pro Ser Ser Leu Ser Ala Ser Val Gly
1               5                  10                  15

Asp Arg Val Thr Ile Thr Cys His Ala Ser Gln Asp Ile Asn Ser Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Ile
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Asn Tyr Asn Pro Ser Leu Lys Ser Arg Ile Ser
                180                 185                 190

Ile Thr Arg Asp Asn Ser Lys Asn Thr Phe Phe Leu Gln Leu Asn Ser
            195                 200                 205

Leu Arg Ala Glu Asp Thr Ala Val Tyr Tyr Cys Ala Arg Leu Gly Arg
210                 215                 220

Gly Phe Arg Tyr Trp Gly Gln Gly Thr Leu Val Thr Val Ser Ser
225                 230                 235

<210> SEQ ID NO 60
<211> LENGTH: 717
<212> TYPE: DNA
<213> ORGANISM: Artificial sequence
<220> FEATURE:
<223> OTHER INFORMATION: nucleotide sequence of single chain antibody M15

<400> SEQUENCE: 60

```
gatattcaga tgacccagag cccgagcagc ctgagcgcga gcgtgggcga ccgtgtgacc      60
attacctgcc atgcgagcca ggatattaac gtgaacattg gctggctgca gcagaaaccg    120
ggcaaagcgt ttaaaggcct gatttatcat ggcaaaaacc tggaagatgg cgtgccgagc    180
cgttttagcg gcagcggcag cggcaccgat tttaccctga ccattagcag cctgcagccg    240
gaagattttg cgacctatta ttgcaatcag tatgaaaata cccaattac atttggccag    300
ggcaccaaag tggaaattaa acgtggtgga ggcggttcag gcggaggtgg ctctggcggt    360
ggcggatcgg atgtgcagct ggtggaaagc ggcggcggcc tggtgcagcc gggcggcagc    420
ctgcgtctga gctgcgcggt gagcggctat agcattacca gcgattatgc gtggaactgg    480
attcgtcagg cgccgggcaa aggcctggaa tggctgggct atattagcta tcgtggccgc    540
accagctata acccgagcct gaaaagccgt attagcatta cccgtgataa cagcaaaaac    600
accttttcc tgcagctgaa cagcctgcgt gcggaagata ccgcggtgta ttattgcgcg    660
cgcctgggac gcggcttccg ctactggggc cagggcaccc tggtgaccgt gagcagc      717
```

<210> SEQ ID NO 61
<211> LENGTH: 239
<212> TYPE: PRT
<213> ORGANISM: Artificial sequence
<220> FEATURE:
<223> OTHER INFORMATION: amino acid sequence of single chain antibody M15

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
                20                  25                  30

Ile Gly Trp Leu Gln Gln Lys Pro Gly Lys Ala Phe Lys Gly Leu Ile
            35                  40                  45

Tyr His Gly Lys Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Ile
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Asp Val Gln Leu Val
            115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Ser Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
            195                 200                 205

Leu Arg Ala Glu Asp Thr Ala Val Tyr Tyr Cys Ala Arg Leu Gly Arg
210                 215                 220

Gly Phe Arg Tyr Trp Gly Gln Gly Thr Leu Val Thr Val Ser Ser
225                 230                 235

<210> SEQ ID NO 62
<211> LENGTH: 717
<212> TYPE: DNA
<213> ORGANISM: Artificial sequence
<220> FEATURE:
<223> OTHER INFORMATION: nucleotide sequence of single chain antibody
      M25

<400> SEQUENCE: 62
gatattcaga tgacccagag cccgagcagc ctgagcgcga gcgtgggcga ccgtgtgacc       60
attacctgcc atgcgagcca ggatattaac gtgaacattg gctggctgca gcagaaaccg      120
ggcaaagcgt ttaaaggcct gatttatcat ggcaaaaacc tggaagatgg cgtgccgagc      180
cgttttagcg gcagcggcag cggcaccgat tttaccctga ccattagcag cctgcagccg      240
gaagattttg cgacctatta ttgcaatcag tatgaaaata tcccactgac atttggccag      300
ggcaccaaag tggaaattaa acgtggtgga ggcggttcag gcggaggtgg ctctggcggt      360
ggcggatcgg atgtgcagct ggtggaaagc ggcggcggcc tggtgcagcc gggcggcagc      420
ctgcgtctga gctgcgcggt gagcggctat agcattacca gcgattatgc gtggaactgg      480
attcgtcagg cgccgggcaa aggcctggaa tggctgggct atattagcta tcgtggccgc      540
acccgctata acccgagcct gaaaagccgt attagcatta cccgtgataa cagcaaaaac      600
acctttttcc tgcagctgaa cagcctgcgt gcggaagata ccgcggtgta ttattgcgcg      660
cgcctgggac gcggcttccg ctactggggc cagggcaccc tggtgaccgt gagcagc         717

<210> SEQ ID NO 63
<211> LENGTH: 239
<212> TYPE: PRT
<213> ORGANISM: Artificial sequence
<220> FEATURE:
<223> OTHER INFORMATION: amino acid sequence of single chain antibody
      M25

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Ile Pro Leu
                85                  90                  95

Thr Phe Gly Gln Gly Thr Lys Val Glu Ile Lys Arg Gly Gly Gly Gly
                100                 105                 110

Ser Gly Gly Gly Gly Ser Gly Gly Gly Ser Asp Val Gln Leu Val
            115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Arg Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235
```

<210> SEQ ID NO 64
<211> LENGTH: 717
<212> TYPE: DNA
<213> ORGANISM: Artificial sequence
<220> FEATURE:
<223> OTHER INFORMATION: nucleotide sequence of single chain antibody M26

<400> SEQUENCE: 64

```
gatattcaga tgacccagag cccgagcagc ctgagcgcga gcgtgggcga ccgtgtgacc    60
attacctgcc atgcgagcca ggatattaac gtgaacattg gctggctgca gcagaaaccg   120
ggcaaagcgt ttaaaggcct gatttatcat ggcaaaaacc tggaagatgg cgtgccgagc   180
cgttttagcg gcagcggcag cggcaccgat tttaccctga ccattagcag cctgcagccg   240
gaagattttg cgacctatta ttgcaatcag tatgaaaata tcccactgac atttggccag   300
ggcaccaaag tggaaattaa acgtggtgga ggcggttcag gcggaggtgg ctctggcggt   360
ggcggatcgg atgtgcagct ggtggaaagc ggcggcggcc tggtgcagcc gggcggcagc   420
ctgcgtctga gctgcgcggt gagcggctat agcattacca gcgattatgc gtggaactgg   480
attcgtcagg cgccgggcaa aggcctggaa tggctgggct atattagcta tcgtggccgc   540
acccagtata acccgagcct gaaaagccgt attagcatta ccgtgataa cagcaaaaac   600
accttttttcc tgcagctgaa cagcctgcgt gcggaagata ccgcggtgta ttattgcgcg   660
cgcctgggac gcggcttccg ctactggggc cagggcaccc tggtgaccgt gagcagc      717
```

<210> SEQ ID NO 65
<211> LENGTH: 239
<212> TYPE: PRT
<213> ORGANISM: Artificial sequence
<220> FEATURE:
<223> OTHER INFORMATION: amino acid sequence of single chain antibody M26

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Ile Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Gln Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235

<210> SEQ ID NO 66
<211> LENGTH: 717
<212> TYPE: DNA
<213> ORGANISM: Artificial sequence
<220> FEATURE:
<223> OTHER INFORMATION: nucleotide sequence of single chain antibody S7

<400> SEQUENCE: 66
gatattcaga tgacccagag cccgagcagc ctgagcgcga gcgtgggcga ccgtgtgacc      60
attacctgcc atgcgagcca ggatattaac gtgaacattg ctggctgca gcagaaaccg     120 ggcaaagcgt ttaaaggcct gatttatcat ggcaccaacc tggaagatgg cgtgccgagc     180
cgttttagcg gcagcggcag cggcaccgat tttaccctga ccattagcag cctgcagccg     240
gaagattttg cgacctatta ttgcaatcag tatgaaaata acccaattac atttggccag     300
ggcaccaaag tggaaattaa acgtggtgga ggcggttcag gcggaggtgg ctctggcggt     360

```
ggcggatcgg atgtgcagct ggtggaaagc ggcggcggcc tggtgcagcc gggcggcagc    420
ctgcgtctga gctgcgcggt gagcggctat agcattacca gcgattatgc gtggaactgg    480
attcgtcagg cgccgggcaa aggcctggaa tggctgggct atattagcta tcgtggccgc    540
accagctata acccgagcct gaaaagccgt attagcatta cccgtgataa cagcaaaaac    600 accttttttcc tgcagctgaa cagcctgcgt gcggaagata ccgcggtgta ttattgcgcg    660
cgcctgggac gcggcttccg ctactggggc cagggcaccc tggtgaccgt gagcagc      717
```

<210> SEQ ID NO 67
<211> LENGTH: 239
<212> TYPE: PRT
<213> ORGANISM: Artificial sequence
<220> FEATURE:
<223> OTHER INFORMATION: amino acid sequence of single chain antibody S7

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Ile
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Ser Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235
```

<210> SEQ ID NO 68
<211> LENGTH: 717
<212> TYPE: DNA
<213> ORGANISM: Artificial sequence
<220> FEATURE:
<223> OTHER INFORMATION: nucleotide sequence of single chain antibody S8

<400> SEQUENCE: 68

```
gatattcaga tgacccagag cccgagcagc ctgagcgcga gcgtgggcga ccgtgtgacc    60
```

-continued

```
attacctgcc atgcgagcca ggatattaac gtgaacattg gctggctgca gcagaaaccg    120
ggcaaaagct ttaaaggcct gatttatcat ggcaaaaacc tggaagatgg cgtgccgagc    180
cgttttagcg gcagcggcag cggcaccgat tttaccctga ccattagcag cctgcagccg    240
gaagattttg cgacctatta ttgcaatcag tatgaaaata cccaattac atttggccag     300 ggcaccaaag tggaaattaa acgtggtgga ggcggttcag gcggaggtgg ctctggcggt    360
ggcggatcgg atgtgcagct ggtggaaagc ggcggcggcc tggtgcagcc gggcggcagc    420
ctgcgtctga gctgcgcggt gagcggctat agcattacca gcgattatgc gtggaactgg    480
attcgtcagg cgccgggcaa aggcctggaa tggctgggct atattagcta tcgtggccgc    540
accagctata acccgagcct gaaaagccgt attagcatta cccgtgataa cagcaaaaac    600
acctttttcc tgcagctgaa cagcctgcgt gcggaagata ccgcggtgta ttattgcgcg    660
cgcctgggac gcggcttccg ctactggggc cagggcaccc tggtgaccgt gagcagc      717
```

<210> SEQ ID NO 69
<211> LENGTH: 239
<212> TYPE: PRT
<213> ORGANISM: Artificial sequence
<220> FEATURE:
<223> OTHER INFORMATION: amino acid sequence of single chain antibody S8

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ser Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Ile
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Ser Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235
```

<210> SEQ ID NO 70

<211> LENGTH: 717
<212> TYPE: DNA
<213> ORGANISM: Artificial sequence
<220> FEATURE:
<223> OTHER INFORMATION: nucleotide sequence of single chain antibody S17

<400> SEQUENCE: 70

```
gatattcaga tgacccagag cccgagcagc ctgagcgcga gcgtgggcga ccgtgtgacc      60
attacctgcc atgcgagcca ggatattaac accaacattg gctggctgca gcagaaaccg     120
ggcaaagcgt ttaaaggcct gatttatcat ggcaaaaacc tggaagatgg cgtgccgagc     180
cgttttagcg gcagcggcag cggcaccgat tttaccctga ccattagcag cctgcagccg     240
gaagattttg cgacctatta ttgcaatcag tatgaaaata ccccactgac atttggccag     300
ggcaccaaag tggaaattaa acgtggtgga ggcggttcag gcggaggtgg ctctggcggt     360
ggcggatcgg atgtgcagct ggtggaaagc ggcggcggcc tggtgcagcc gggcggcagc     420
ctgcgtctga gctgcgcggt gagcggctat agcattacca gcgattatgc gtggaactgg     480
attcgtcagg cgccgggcaa aggcctggaa tggctgggct atattagcta tcgtggccgc     540
acccagtata acccgagcct gaaaagccgt attagcatta cccgtgataa cagcaaaaac     600
acctttttcc tgcagctgaa cagcctgcgt gcggaagata ccgcggtgta ttattgcgcg     660
cgcctgggac gcggcttccg ctactggggc cagggcaccc tggtgaccgt gagcagc       717
```

<210> SEQ ID NO 71
<211> LENGTH: 239
<212> TYPE: PRT
<213> ORGANISM: Artificial sequence
<220> FEATURE:
<223> OTHER INFORMATION: amino acid sequence of single chain antibody S17

<400> SEQUENCE: 71

```
Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Asn Thr Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Leu
                85                  90                  95

Thr Phe Gly Gln Gly Thr Lys Val Glu Ile Lys Arg Gly Gly Gly Gly
           100                 105                 110

Ser Gly Gly Gly Gly Ser Gly Gly Gly Ser Asp Val Gln Leu Val
        115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Gln Tyr Asn Pro Ser Leu Lys Ser Arg Ile Ser
            180                 185                 190
```

```
Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
        210                 215                 220

Gly Phe Arg Tyr Trp Gly Gln Gly Thr Leu Val Thr Val Ser Ser
225                 230                 235
```

<210> SEQ ID NO 72
<211> LENGTH: 717
<212> TYPE: DNA
<213> ORGANISM: Artificial sequence
<220> FEATURE:
<223> OTHER INFORMATION: nucleotide sequence of single chain antibody
      S22

<400> SEQUENCE: 72

```
gatattcaga tgacccagag cccgagcagc ctgagcgcga gcgtgggcga ccgtgtgacc      60
attacctgcc atgcgagcca ggatattaac gtgaacattg ctggctgca gcagaaaccg     120
ggcaaagcgt ttaaaggcct gatttatcat ggcaccaacc tggaagatgg cgtgccgagc     180
cgttttagcg gcagcggcag cggcaccgat tttaccctga ccattagcag cctgcagccg     240
gaagattttg cgacctatta ttgcaatcag tatgaaaata ccccactgac atttggccag     300
ggcaccaaag tggaaattaa acgtggtgga ggcggttcag gcggaggtgg ctctggcggt     360
ggcggatcgg atgtgcagct ggtggaaagc ggcggcggcc tggtgcagcc gggcggcagc     420
ctgcgtctga gctgcgcggt gagcggctat agcattacca gcgattatgc gtggaactgg     480
attcgtcagg cgccgggcaa aggcctggaa tggctgggct atattagcta tcgtggccgc     540
acccgctata acccgagcct gaaaagccgt attagcatta cccgtgataa cagcaaaaac     600
acctttttcc tgcagctgaa cagcctgcgt gcggaagata ccgcggtgta ttattgcgcg     660
cgcctgggac gcggcttccg ctactggggc cagggcaccc tggtgaccgt gagcagc        717
```

<210> SEQ ID NO 73
<211> LENGTH: 239
<212> TYPE: PRT
<213> ORGANISM: Artificial sequence
<220> FEATURE:
<223> OTHER INFORMATION: amino acid sequence of single chain antibody
      S22

<400> SEQUENCE: 73

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Asn Gln Tyr Glu Asn Asn Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Asp Val Gln Leu Val
        115                 120                 125
```

Glu Ser Gly Gly Gly Leu Val Gln Pro Gly Gly Ser Leu Arg Leu Ser
        130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Arg Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235

<210> SEQ ID NO 74
<211> LENGTH: 717
<212> TYPE: DNA
<213> ORGANISM: Artificial sequence
<220> FEATURE:
<223> OTHER INFORMATION: nucleotide sequence of single chain antibody
      S23

<400> SEQUENCE: 74
gatattcaga tgacccagag cccgagcagc ctgagcgcga gcgtgggcga ccgtgtgacc      60
attacctgcc atgcgagcca ggatattaac gtgaacattg ctggctgca gcagaaaccg     120 ggcaaaagct ttaaaggcct gatttatcat ggcaaaaacc tggaagatgg cgtgccgagc     180
cgttttagcg gcagcggcag cggcaccgat tttaccctga ccattagcag cctgcagccg     240
gaagattttg cgacctatta ttgcaatcag tatgaaaata ccccactgac atttggccag     300
ggcaccaaag tggaaattaa acgtggtgga ggcggttcag gcggaggtgg ctctggcggt     360
ggcggatcgg atgtgcagct ggtggaaagc ggcggcggcc tggtgcagcc gggcggcagc     420
ctgcgtctga gctgcgcggt gagcggctat agcattacca gcgattatgc gtggaactgg     480
attcgtcagg cgccgggcaa aggcctggaa tggctgggct atattagcta tcgtggccgc     540
acccgctata acccgagcct gaaaagccgt attagcatta cccgtgataa cagcaaaaac     600
acctttttcc tgcagctgaa cagcctgcgt gcggaagata ccgcggtgta ttattgcgcg     660
cgcctgggac gcggcttccg ctactggggc cagggcaccc tggtgaccgt gagcagc       717

<210> SEQ ID NO 75
<211> LENGTH: 239
<212> TYPE: PRT
<213> ORGANISM: Artificial sequence
<220> FEATURE:
<223> OTHER INFORMATION: amino acid sequence of single chain antibody
      S23

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ser Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Asn Gln Tyr Glu Asn Asn Pro Leu
             85                  90                  95

Thr Phe Gly Gln Gly Thr Lys Val Glu Ile Lys Arg Gly Gly Gly Gly
         100                 105                 110

Ser Gly Gly Gly Gly Ser Gly Gly Gly Ser Asp Val Gln Leu Val
     115                 120                 125

Glu Ser Gly Gly Gly Leu Val Gln Pro Gly Gly Ser Leu Arg Leu Ser
130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Arg Tyr Asn Pro Ser Leu Lys Ser Arg Ile Ser
            180                 185                 190

Ile Thr Arg Asp Asn Ser Lys Asn Thr Phe Phe Leu Gln Leu Asn Ser
        195                 200                 205

Leu Arg Ala Glu Asp Thr Ala Val Tyr Tyr Cys Ala Arg Leu Gly Arg
    210                 215                 220

Gly Phe Arg Tyr Trp Gly Gln Gly Thr Leu Val Thr Val Ser Ser
225                 230                 235

<210> SEQ ID NO 76
<211> LENGTH: 717
<212> TYPE: DNA
<213> ORGANISM: Artificial sequence
<220> FEATURE:
<223> OTHER INFORMATION: nucleotide sequence of single chain antibody
      S29

<400> SEQUENCE: 76
gatattcaga tgacccagag cccgagcagc ctgagcgcga gcgtgggcga ccgtgtgacc    60
attacctgcc atgcgagcca ggatattaac gtgaacattg ctggctgca gcagaaaccg   120 ggcaaagcgt ttaaaggcct gatttatcat ggcaaaaacc tggaagatgg cgtgccgagc   180
cgttttagcg gcagcggcag cggcaccgat tttaccctga ccattagcag cctgcagccg   240
gaagattttg cgacctatta ttgcaatcag tatgaaaatt ccccactgac atttggccag   300
ggcaccaaag tggaaattaa acgtggtgga ggcggttcag gcggaggtgg ctctggcggt   360
ggcggatcgg atgtgcagct ggtggaaagc ggcggcggcc tggtgcagcc gggcggcagc   420
ctgcgtctga gctgcgcggt gagcggctat agcattacca gcgattatgc gtggaactgg   480
attcgtcagg cgccgggcaa aggcctggaa tggctgggct atattagcta tcgtggccgc   540
acccgctata acccgagcct gaaaagccgt attagcatta cccgtgataa cagcaaaaac   600
acctttttcc tgcagctgaa cagcctgcgt gcggaagata ccgcggtgta ttattgcgcg   660
cgcctgggac gcggcttccg ctactggggc cagggcaccc tggtgaccgt gagcagc     717

<210> SEQ ID NO 77
<211> LENGTH: 239
<212> TYPE: PRT
<213> ORGANISM: Artificial sequence
<220> FEATURE:
<223> OTHER INFORMATION: amino acid sequence of single chain antibody
      S29

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Val Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Asn Gln Tyr Glu Asn Phe Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Asp Val Gln Leu Val
            115                 120                 125

Glu Ser Gly Gly Gly Leu Val Gln Pro Gly Gly Ser Leu Arg Leu Ser
    130                 135                 140

Cys Ala Val Ser Gly Tyr Ser Ile Thr Ser Asp Tyr Ala Trp Asn Trp
145                 150                 155                 160

Ile Arg Gln Ala Pro Gly Lys Gly Leu Glu Trp Leu Gly Tyr Ile Ser
                165                 170                 175

Tyr Arg Gly Arg Thr Arg Tyr Asn Pro Ser Leu Lys Ser Arg Ile Ser
                180                 185                 190

Ile Thr Arg Asp Asn Ser Lys Asn Thr Phe Phe Leu Gln Leu Asn Ser
            195                 200                 205

Leu Arg Ala Glu Asp Thr Ala Val Tyr Tyr Cys Ala Arg Leu Gly Arg
        210                 215                 220

Gly Phe Arg Tyr Trp Gly Gln Gly Thr Leu Val Thr Val Ser Ser
225                 230                 235
```

TUMOR-SPECIFIC ANTI-EGFR ANTIBODY AND APPLICATION THEREOF

TECHNICAL FIELD

The present invention relates to the field of immunology, and in particular, the present invention relates to tumor-specific anti-EGFR antibodies and uses thereof.

BACKGROUND

EGFR is overexpressed or mutated in many tumors, and it is undoubtedly a very important scientific issue on how to selectively recognize these over-expressed or mutated EGFR. Until now, antibodies against EGFR287-302 epitope are believed to achieve the purpose of recognizing EGFR, EGFRvIII and de4 EGFR overexpressed on the surface of tumors, instead of EGFR in normal cells. Unfortunately, antibodies against this epitope still have side effects such as rashes in clinical trials (http://meetinglibrary.asco.org/content/115945-132), suggesting that targeting this epitope may identify EGFR in normal cells (such as keratinocytes).

Therefore, it is very urgent to screen anti-EGFR antibodies with higher tumor-specificity. Highly tumor-specific antibodies, whether for tumor imaging diagnosis, individual diagnosis or tumor targeting therapy, have a very large potential value.

SUMMARY OF THE INVENTION

The object of the present invention is to provide tumor-specific anti-EGFR antibodies and uses thereof.

In a first aspect of the present invention, an antibody specifically recognizing EGFRvIII expressed or EGFR overexpressed by tumor cells is provided, wherein the antibody comprises a light chain variable region and a heavy chain variable region, CDR1 of the light chain variable region has an amino acid sequence selected from a group consisting of SEQ ID NO: 41, SEQ ID NO: 47, SEQ ID NO: 55;

CDR2 of the light chain variable region has an amino acid sequence selected from a group consisting of SEQ ID NO: 42, SEQ ID NO: 53;

CDR3 of the light chain variable region has an amino acid sequence selected from a group consisting of SEQ ID NO: 43, SEQ ID NO: 48, SEQ ID NO: 54, SEQ ID NO: 56, SEQ ID NO: 57;

CDR1 of the heavy chain variable region has the amino acid sequence of SEQ ID NO: 44;

CDR2 of the heavy chain variable region has an amino acid sequence selected from a group consisting of SEQ ID NO: 45, SEQ ID NO: 49, SEQ ID NO: 51, SEQ ID NO: 52;

CDR3 of the heavy chain variable region has an amino acid sequence selected from a group consisting of SEQ ID NO: 46, SEQ ID NO: 50.

In a preferred embodiment, the antibody includes:

antibody (a), wherein the light chain variable region thereof has CDR1 of SEQ ID NO: 41, CDR2 of SEQ ID NO: 42, CDR3 of SEQ ID NO: 43, or the heavy chain variable region thereof has CDR1 of SEQ ID NO: 44, CDR2 of SEQ ID NO: 45, CDR3 of SEQ ID NO: 46, antibody (b), wherein the light chain variable region thereof has CDR1 of SEQ ID NO: 47, CDR2 of SEQ ID NO: 42, CDR3 of SEQ ID NO: 48, or the heavy chain variable region thereof has CDR1 of SEQ ID NO: 44, CDR2 of SEQ ID NO: 49, CDR3 of SEQ ID NO: 50, antibody (c), wherein the light chain variable region thereof has CDR1 of SEQ ID NO: 41, CDR2 of SEQ ID NO: 42, CDR3 of SEQ ID NO: 48, or the heavy chain variable region thereof has CDR1 of SEQ ID NO: 44, CDR2 of SEQ ID NO: 51, CDR3 of SEQ ID NO: 50, antibody (d), wherein the light chain variable region thereof has CDR1 of SEQ ID NO: 41, CDR2 of SEQ ID NO: 42, CDR3 of SEQ ID NO: 43, or the heavy chain variable region thereof has CDR1 of SEQ ID NO: 44, CDR2 of SEQ ID NO: 52, CDR3 of SEQ ID NO: 50, antibody (e), wherein the light chain variable region thereof has CDR1 of SEQ ID NO: 41, CDR2 of SEQ ID NO: 42, CDR3 of SEQ ID NO: 43, or the heavy chain variable region thereof has CDR1 of SEQ ID NO: 44, CDR2 of SEQ ID NO: 45, CDR3 of SEQ ID NO: 50, antibody (f), wherein light chain variable region thereof has CDR1 of SEQ ID NO: 41, CDR2 of SEQ ID NO: 53, CDR3 of SEQ ID NO: 54, or the heavy chain variable region thereof has CDR1 of SEQ ID NO: 44, CDR2 of SEQ ID NO: 51, CDR3 of SEQ ID NO: 50, antibody (g), wherein the light chain variable region has CDR1 of SEQ ID NO: 41, CDR2 of SEQ ID NO: 42, CDR3 of SEQ ID NO: 54, or the heavy chain variable region thereof has CDR1 of SEQ ID NO: 44, CDR2 of SEQ ID NO: 51, CDR3 of SEQ ID NO: 50, antibody (h), wherein the light chain variable region thereof has CDR1 of SEQ ID NO: 55, CDR2 of SEQ ID NO: 42, CDR3 of SEQ ID NO: 56, or the heavy chain variable region thereof has CDR1 of SEQ ID NO: 44, CDR2 of SEQ ID NO: 45, CDR3 of SEQ ID NO: 50, antibody (i), wherein the light chain variable region thereof has CDR1 of SEQ ID NO: 41, CDR2 of SEQ ID NO: 53, CDR3 of SEQ ID NO: 56, or the heavy chain variable region thereof has CDR1 of SEQ ID NO: 44, CDR2 of SEQ ID NO: 52, CDR3 of SEQ ID NO: 50, antibody (j), wherein the light chain variable region thereof has CDR1 of SEQ ID NO: 41, CDR2 of SEQ ID NO: 42, CDR3 of SEQ ID NO: 56, or the heavy chain variable region thereof has CDR1 of SEQ ID NO: 44, CDR2 of SEQ ID NO: 52, CDR3 of SEQ ID NO: 50, antibody (k), wherein the light chain variable region thereof has CDR1 of SEQ ID NO: 41, CDR2 of SEQ ID NO: 42, CDR3 of SEQ ID NO: 57, or the heavy chain variable region thereof has CDR1 of SEQ ID NO: 44, CDR2 of SEQ ID NO: 52, CDR3 of SEQ ID NO: 50; or antibody (1) which recognizes the same antigenic determinant as that recognized by the antibody according to any one of (a) to (k).

In another preferred embodiment, the antibody specifically recognizing EGFRvIII expressed or EGFR overexpressed by tumor cells can be: single chain antibody (scFV), monoclonal antibody, domain antibody, Fab fragment, Fd fragment, Fv fragment, F (ab')$_2$ fragment and a derivative thereof, or other forms of antibody; preferably single chain antibody.

In another preferred embodiment, the antibody specifically recognizing EGFRvIII expressed or EGFR overexpressed by tumor cells is humanized, fully humanized, chimeric or murine.

In another preferred embodiment, the amino acid sequence of the heavy chain variable region of the antibody is shown in positions 124 to 239 of SEQ ID NO: 13; or the amino acid sequence of the light chain variable region of the antibody is shown in positions 1-108 of SEQ ID NO: 13;

The amino acid sequence of the heavy chain variable region of the antibody is shown in positions 124 to 239 of SEQ ID NO: 59; or the amino acid sequence of the light chain variable region of the antibody is shown in positions 1-108 of SEQ ID NO: 59;

The amino acid sequence of the heavy chain variable region of the antibody is shown in positions 124 to 239 of SEQ ID NO: 61; or the amino acid sequence of the light chain variable region of the antibody is shown in positions 1-108 of SEQ ID NO: 61;

The amino acid sequence of the heavy chain variable region of the antibody is shown in positions 124 to 239 of SEQ ID NO: 63; or the amino acid sequence of the light chain variable region of the antibody is shown in positions 1-108 of SEQ ID NO: 63;

The amino acid sequence of the heavy chain variable region of the antibody is shown in positions 124 to 239 of SEQ ID NO: 65; or the amino acid sequence of the light chain variable region of the antibody is shown in positions 1-108 of SEQ ID NO: 65;

The amino acid sequence of the heavy chain variable region of the antibody is shown in positions 124 to 239 of SEQ ID NO: 67; or the amino acid sequence of the light chain variable region of the antibody is shown in positions 1-108 of SEQ ID NO: 67;

The amino acid sequence of the heavy chain variable region of the antibody is shown in positions 124 to 239 of SEQ ID NO: 69; or the amino acid sequence of the light chain variable region of the antibody is shown in positions 1-108 of SEQ ID NO: 69;

The amino acid sequence of the heavy chain variable region of the antibody is shown in positions 124 to 239 of SEQ ID NO: 71; or the amino acid sequence of the light chain variable region of the antibody is shown in positions 1-108 of SEQ ID NO: 71;

The amino acid sequence of the heavy chain variable region of the antibody is shown in positions 124 to 239 of SEQ ID NO: 73; or the amino acid sequence of the light chain variable region of the antibody is shown in positions 1-108 of SEQ ID NO: 73;

The amino acid sequence of the heavy chain variable region of the antibody is shown in positions 124 to 239 of SEQ ID NO: 75; or the amino acid sequence of the light chain variable region of the antibody is shown in positions 1-108 of SEQ ID NO: 75; or The amino acid sequence of the heavy chain variable region of the antibody is shown in positions 124 to 239 of SEQ ID NO: 77; or the amino acid sequence of the light chain variable region of the antibody is shown in positions 1-108 of SEQ ID NO: 77.

In another preferred embodiment, the antibody is antibody (a); more preferably, the amino acid sequence of the heavy chain variable region of the antibody is shown in positions 124 to 239 of SEQ ID NO: 13; or the amino acid sequence of the light chain variable region of the antibody is shown in positions 1-108 of SEQ ID NO: 13.

In another aspect of the invention, a nucleic acid encoding the antibody as described above is provided.

In another aspect of the present invention, an expression vector is provided, comprising the nucleic acid. In another preferred embodiment, the expression vector is a PH/DHFR vector.

In another aspect of the present invention, a host cell is provided, comprising the expression vector or having the nucleic acid integrated into its genome. In another preferred embodiment, the host cell is a eukaryotic host cell or prokaryotic host cell; preferably a eukaryotic host cell, more preferably Chinese hamster ovary cell (CHO).

In another aspect of the invention, the use of any one of the above described antibodies is provided for the manufacture of a targeting drug, antibody drug conjugate, or multi-functional antibody specifically targeting tumor cells expressing EGFRvIIIed or over-expressing EGFR; or an agent for diagnosis of tumors that express EGFRvIII or overexpress EGFR; or is used to prepare a chimeric antigen receptor modified immune cell; preferably, the immune cell includes: T lymphocyte, NK cell or NKT lymphocyte.

In another aspect of the present invention, a multi-functional immunoconjugate is provided, comprising: any one of the above described antibodies; and a functional molecule linked thereto (including covalently linked, conjugated, attached, adsorbed); the functional molecule is selected from a group consisting of a molecule that targets a tumor surface marker, a tumor-suppressing molecule, a molecule that targets a surface marker of an immune cell, or a detectable label.

In a preferred embodiment, the molecule that targets the tumor surface marker is an antibody or ligand that binds to a tumor surface marker; or the tumor-suppressing molecule is an anti-tumor cytokine or an anti-tumor toxin; preferably, the cytokines include but are not limited to: IL-12, IL-15, IFN-beta, TNF-alpha.

In another preferred embodiment, in the multi-functional immunoconjugate, the detectable label includes a fluorescent label and a chromogenic label.

In another preferred embodiment, in the multi-functional immunoconjugate, the molecule targeting the surface marker of the immune cell is an antibody or ligand that binds to an immune cell surface marker; preferably, the immune cell surface markers include, but are not limited to: CD3, CD16, CD28.

In another preferred embodiment, in the multi-functional immunoconjugate, the molecule that targets the surface marker of the immune cell is an antibody that binds to a T cell surface marker, which can form a T-cell-engaging bifunctional antibody with any one of the above described antibody (bispecific T cell engager, BiTE).

In another preferred embodiment, in the multi-functional immunoconjugate, the antibody that binds to the immune cell surface marker is an anti-CD3 antibody. In another preferred embodiment, the anti-CD3 antibody is a single chain antibody (scFV), a monoclonal antibody, a Fab fragment, an Fd fragment, an Fv fragment, an F(ab')$_2$ fragment and a derivative thereof, antibody; preferably single chain antibody. In another preferred embodiment, the anti-CD3 antibody is humanized, fully human, chimeric or murine.

In another preferred embodiment, the multi-functional immunoconjugate is a fusion polypeptide, and further comprises a linker peptide (linker) between any one of the above described antibodies and the functional molecule linked thereto.

In another preferred embodiment, the linker peptide has the sequence (GlyGlyGlyGlySer)n, wherein n is an integer from 1 to 5; more preferably, n=3.

In another preferred embodiment, the multi-functional immunoconjugate is administered in a form of polypeptide or in the manner of gene administration.

In another aspect of the invention, a nucleic acid encoding the multi-functional immunoconjugate is provided.

In another aspect of the invention, the use of any one of the above described multi-functional immunoconjugate is provided, for the preparation of an antineoplastic agent or an agent for diagnosis of tumors that express EGFRvIII or overexpress EGFR; or for the preparation of chimeric antigen receptor modified immune cells. Preferably, the immune cells include T lymphocyte, NK cell or NKT lymphocyte.

In another aspect of the present invention, a chimeric antigen receptor comprising any one of the above described antibodies is provided, and the chimeric antigen receptor is expressed on the surface of an immune cell and comprises: any one of the above described antibodies, a transmembrane region and an intracellular signal region, which are sequentially linked; and the intracellular signal region is selected from a group consisting of intracellular signal region sequences of CD3ζ, FcεRIγ, CD27, CD28, CD137 and CD134, or a combination thereof.

In a preferred embodiment, the transmembrane region comprises a transmembrane region of CD8 or CD28.

In another preferred embodiment, the immune cells include T lymphocyte, NK cell or NKT cell.

In another preferred embodiment, the chimeric antigen receptor comprises the following sequentially linked antibody, transmembrane region and intracellular signal region:

Any one of the above described antibodies, CD8 and CD3ζ;

Any one of the above described antibodies, CD8, CD137 and CD3ζ;

Any one of the above described antibodies, a transmembrane region of a CD28 molecule, an intracellular signal region of a CD28 molecule, and CD3ζ; or Any one of the above described antibodies, a transmembrane region of a CD28 molecule, an intracellular signal region of a CD28 molecule, CD137 and CD3ζ.

In another preferred embodiment, the antibody is a single chain antibody or a domain antibody.

In another preferred embodiment, the chimeric antigen receptor comprises:

SEQ ID NO: 36 or the amino acid sequence shown in positions 285-601; or

SEQ ID NO: 37 or the amino acid sequence shown in positions 285-702; or

SEQ ID NO: 38 or the amino acid sequence shown in positions 285-744; or

SEQ ID NO: 39 or the amino acid sequence shown in positions 285-749; or

SEQ ID NO: 40 or the amino acid sequence shown in positions 285-791.

In another aspect of the invention, a nucleic acid encoding any one of the above described chimeric antigen receptors is provided. In another preferred embodiment, the nucleic acid encoding the chimeric antigen receptor comprises:

SEQ ID NO: 31 or the nucleotide sequence shown in positions 966-1916; or

SEQ ID NO: 32 or the nucleotide sequence shown in positions 966-2219; or

SEQ ID NO: 33 or the nucleotide sequence shown in positions 966-2345; or

SEQ ID NO: 34 or the nucleotide sequence shown in positions 966-2360; or

SEQ ID NO: 35 or the nucleotide sequences shown in positions 966-2486.

In another aspect of the present invention, an expression vector comprising the above described nucleic acid is provided.

In another preferred embodiment, the expression vector is derived from lentiviral plasmid pWPT (or pWPT-eGFP).

In another aspect of the present invention, a virus comprising the above described vector is provided.

Use of any one of the above described chimeric antigen receptors or an encoding nucleic acid thereof, or an expression vector or virus comprising the nucleic acid is provided, for the preparation of genetically modified immune cells that target tumor cells that express EGFRvIII or overexpress EGFR.

In another aspect of the present invention, a genetically modified immune cell is provided, which is transduced with the nucleic acid, or the expression vector or the virus; or expresses the chimeric antigen receptor at its surface.

In a preferred embodiment, the immune cell further carries an exogenous encoding sequence for cytokine; preferably, the cytokine includes: IL-12, IL-15 or IL-21.

In another preferred embodiment, the immune cell further expresses another chimeric antigen receptor that does not contain CD3ζ, but contains the intracellular signaling domain of CD28, the intracellular signaling domain of CD137, or a combination of both.

In another preferred embodiment, the immune cell further expresses a chemokine receptor; preferably, the chemokine receptor includes CCR2.

In another preferred embodiment, the immune cell further expresses siRNA that can reduce PD-1 expression or a protein that can block PD-L1.

In another preferred embodiment, the immune cell further expresses a safety switch; preferably, the safety switch includes iCaspase-9, Truancated EGFR or RQR8.

In another aspect of the invention, the use of said genetically modified immune cells is provided for the preparation of a tumor-inhibiting drug, and said tumor is the tumor that expresses EGFRvIII or overexpresses EGFR.

In another aspect of the invention, a pharmaceutical composition (including medicament or diagnostic reagent) is provided, comprising:

any one of the above described antibodies or a nucleic acid encoding the antibody; or any one of the above described immunoconjugates or a nucleic acid encoding the conjugate; or any one of the above described chimeric antigen receptors or a nucleic acid encoding the chimeric antigen receptor; or any one of the above described genetically modified immune cells.

Other aspects of the invention will be apparent to a person skilled in the art in view of the disclosure herein.

DESCRIPTION OF DRAWINGS

FIG. 4. Electrophorogram of purification of three scFv-Fc fusion antibodies.

FIG. 5. Detection of single-chain antibodies scFv-Y022-Fc, scFv-806-Fc and scFv-C225-Fc for their ability to bind to cell surface EGFR by FACS.

FIG. 6. Structure diagram of pH-Y022/CD3 expression vector.

FIG. 7. SDS-PAGE detection of single-chain bifunctional antibodies Y022/CD3, 806/CD3 and C225/CD3.

MODES FOR CARRYING OUT THE INVENTION

Figure 1:
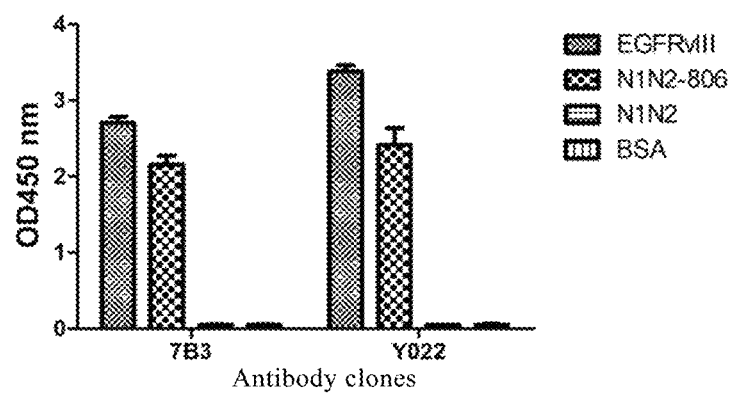
FIG. 1. Antibodies 7B3 and Y022 can specifically bind to antigens EGFRvIII and N1N2-806 (phage ELISA assay).

After intensive research and screening, the present inventors obtained an antibody that specifically recognizes EGFRvIII or over-expressed EGFR in tumor cells and scarcely recognizes EGFR in normal cells. The antibody of the present invention can be used to prepare various targeting anti-tumor drugs and drugs for diagnosis of tumors.

Anti-EGFR Antibody

The present inventors further conducted screening and amino acid mutations based on the humanized antibodies obtained in the previous stage, and found an anti-EGFR antibody capable of targeting EGFR of tumor cells with higher specificity, which selectively binds to a tumor over-expressing EGFR or EGFRvIII, while does not bind to EGFR on normal cells.

Antibodies of the invention may be intact immunoglobulin molecules or antigen-binding fragments, including but not limited to Fab fragments, Fd fragments, Fv fragments, F(ab')$_2$ fragments, complementarity determining region (CDR) fragments, single-chain antibody (scFv), domain antibody, bivalent single chain antibody, single chain phage antibody, bispecific diabody, triple chain antibody, quadruple chain antibody.

The antigen-binding properties of an antibody can be described by three specific regions located in variable regions of the heavy and light chains, termed complementarity determining regions (CDRs), which divide the variable regions into four framework regions (FR), and the amino acid sequences of four FRs are relatively conservative, not directly involved in binding reaction. These CDRs form a loop structure, in which β-folds formed by the FRs are located close to each other in space and the antigen binding site of the antibody is constituted by CDRs on the heavy chain and CDRs on the corresponding light chain. It is possible to determine which amino acids make up FR or CDR regions by comparing the amino acid sequences of the same type of antibody. The CDR regions are sequences of immunologically interesting proteins and the CDR regions of the antibodies of the invention are brand new. The antibody may comprise two, three, four, five, or all six of the CDR regions disclosed herein.

Another aspect of the invention includes functional variants of the antibodies described herein. If the variant is capable of competing with the parental antibody for specific binding to SEQ ID NO: 1 and its ability to recognize EGFRvIII or overexpressed EGFR in tumor cells is close to that of the specific antibodies provided in Examples of the present invention. The functional variants may have conservative sequence modifications, including nucleotide and amino acid substitutions, additions and deletions. These modifications can be introduced by standard techniques known in the art, such as directed mutagenesis and random PCR-mediated mutagenesis, and can include both natural and non-natural nucleotides and amino acids. Preferably, modification of the sequence occurs on a region outside the CDR region of the antibody.

Immunoconjugate

In the present invention, a multifunctional immunoconjugate is also provided, comprising the antibodies described herein and further comprising at least one functional molecule of other type. The functional molecule is selected from, but not limited to, a molecule that targets a tumor surface marker, a tumor-suppressing molecule, a molecule that targets a surface marker of an immune cell, or a detectable label. The antibody and the functional molecule may form a conjugate by covalent attachment, coupling, attachment, cross-linking, or the like.

As a preferred mode, the immunoconjugate may comprise an antibody of the invention and at least one molecule that targets a tumor surface marker or a tumor-suppressing molecule. The tumor-suppressing molecule may be anti-tumor cytokines or anti-tumor toxins. Preferably, the cytokines include but are not limited to IL-12, IL-15, IFN-beta, TNF-alpha. The molecules that target tumor surface markers, for example, can act synergistically with the antibodies of the invention to more precisely target tumor cells.

As a preferred mode, the immunoconjugate may comprise an antibody of the present invention and a detectable label. Such detectable labels include, but are not limited to, fluorescent labels, chromogenic labels such as enzymes, prosthetic groups, fluorescent materials, luminescent materials, bioluminescent materials, radioactive materials, positron-emitting metals and non-radioactive paramagnetic metal ion. More than one marker can also be included. The label used to label the antibody for the purpose of detection and/or analysis and/or diagnosis depends on the used particular detection/analysis/diagnosis technique and/or method, eg, immunohistochemical staining (tissue) samples, flow cytometry, and the like. Suitable labels for detection/analysis/diagnosis techniques and/or methods known in the art are well known to those skilled in the art.

As a preferred mode, the immunoconjugate may comprise an antibody of the invention as well as a molecule that targets a surface marker of an immune cell. The molecule that targets surface markers of immune cells can recognize immune cells and carry the antibodies of the invention to the immune cells, so that the antibodies of the invention can target the immune cells to the tumor cells and thus trigger immunocyte for specifically killing tumor.

As a means of chemically generating an immunoconjugate by conjugation, either directly or indirectly (eg, by a linker), the immunoconjugate can be produced as a fusion protein comprising an antibody of the invention and other suitable proteins. The fusion protein can be produced by a method known in the art, for example recombinantly produced by constructing and subsequently expressing the nucleic acid molecule which comprises the nucleotide sequence encoding the antibody in frame with a nucleotide sequence encoding a suitable label.

In another aspect of the invention, a nucleic acid molecule encoding at least one antibody of the invention, a functional variant, or an immunoconjugate thereof is provided. Once obtaining the relevant sequence, the recombination method can be used to obtain the relevant sequence in large quantities. This is usually done by cloning it into a vector, transferring it to a cell, and then isolating the relevant sequence from the proliferating host cells by conventional methods.

The present invention also relates to vectors comprising the appropriate DNA sequences described above as well as appropriate promoters or control sequences. These vectors can be used to transform an appropriate host cell to enable expression of the protein. The host cell may be a prokaryotic cell, such as a bacterial cell; or a lower eukaryotic cell, such as a yeast cell; or a higher eukaryotic cell, such as a mammalian cell.

Chimeric Antigen Receptor and Genetically Modified Immune Cell

In the present invention, a chimeric antigen receptor expressed on the surface of an immune effector cell (immune cell) is provided, wherein the chimeric antigen receptor comprises sequentially linked: extracellular binding region, transmembrane region and intracellular signal region, and the extracellular binding region comprises the antibody of the invention. By expressing the chimeric antigen receptor on the surface of immune effector cells, immune effector cells can have a highly specific cytotoxic effect on tumor cells that express EGFRvIII or overexpress EGFR.

As used herein, "immune cells" and "immune effector cells" are used interchangeably and include: T lymphocytes, NK cells or NKT cells, and the like.

As a preferred embodiment of the present invention, the antibody contained in the chimeric antigen receptor is a single chain antibody, which is connected to CD8 or the transmembrane region of CD28 through the hinge region of CD8, and the transmembrane region is immediately followed by the intracellular signal region.

The invention also includes nucleic acids encoding the chimeric antigen receptors. The present invention also relates to variants of the above described polynucleotides, which encode a polypeptide, or a fragment, analog and derivative of the polypeptide having the same amino acid sequence as the present invention.

The transmembrane region of the chimeric antigen receptor may be selected from the transmembrane region of a protein such as CD8 or CD28. The human CD8 protein is a heterodimer composed of two chains, αβ or γδ. In one embodiment of the invention, the transmembrane region is selected from the transmembrane region of CD8a or CD28. In addition, the CD8a hinge is a flexible region so that CD8 or CD28 and the transmembrane region as well as the hinge region are used to connect the target recognition domain scFv of the chimeric antigen receptor CAR to the intracellular signal region.

The intracellular signal region may be selected from a group consisting of intracellular signal region of CD3ζ, FcεRIγ, CD28, CD137, CD134 protein, and combinations thereof. The CD3 molecule consists of five subunits, in which CD3 subunit (also known as CD3 zeta, abbreviated as Z) contains 3 ITAM motifs that are important signal transduction regions in TCR-CD3 complex. CD3δZ is a truncated CD3ζ sequence without ITAM motif and is generally constructed in the present invention as a negative control. FcεRIγ is mainly distributed on the surface of mast cells and basophils, which contains an ITAM motif, which is similar to CD3ζ in structure, distribution and function. In addition, as mentioned above, CD28, CD137 and CD134 are co-stimulatory signaling molecules. The co-stimulatory effect of their intracellular signaling segments upon binding to the respective ligands results in the continued proliferation of immune effector cells, primarily T lymphocytes, and increase in the level of cytokines such as IL-2 and IFN-γ secreted by immune effector cells, and the survival period and anti-tumor effect of CAR immune effector cells in vivo are increased.

The chimeric antigen receptor of the present invention can be sequentially linked as follows:

The antibody of the invention, CD8 and CD3ζ;

The antibody of the invention, CD8, CD137 and CD3ζ;

The antibody of the invention, the transmembrane region of CD28 molecule, the intracellular signal region of CD28 molecule and CD3ζ; or The antibodies of the invention, the transmembrane region of CD28 molecule, the intracellular signal region of CD28 molecule, CD137 and CD3ζ.

And combinations thereof, wherein CD28a in the relevant chimeric antigen receptor protein represents the transmembrane region of CD28 molecule and CD28b represents the intracellular signal region of CD28 molecule. The various chimeric antigen receptors described above are collectively referred to as scFv (EGFR)-CAR.

The present invention also provides a vector comprising the above-mentioned nucleic acid encoding a chimeric antigen receptor protein expressed on the surface of an immune effector cell. In a specific embodiment, the vector used in the present invention is a lentiviral plasmid vector pWPT-eGFP. This plasmid belongs to the third generation of self-inactivating lentiviral vector system. The system has three plasmids, packaging plasmid psPAX2 encoding protein Gag/Pol, encoding Rev protein; envelope plasmid PMD2.G encoding VSV-G protein; and empty vector pWPT-eGFP, which can be used for recombinant introduction of a nucleic acid sequence of interest, i.e., a nucleic acid encoding CAR. In the empty vector pWPT-eGFP, the expression of enhanced green fluorescent protein (eGFP) is regulated by elongation factor-1α (EF-1α) promoter. While in the recombinant expression vector pWPT-eGFP-F2A-CAR containing the nucleic acid sequence encoding CAR, co-expression of eGFP and CAR is achieved by ribosomal skipping sequence 2A (abbreviated as F2A) from food-and-mouth disease virus (FMDV).

The invention also includes viruses comprising the vectors described above. The viruses of the invention include packaged infectious viruses as well as viruses to be packaged that contain the necessary components for packaging into infectious viruses. Other viruses known in the art that can be used to transduce exogenous genes into immune effector cells and their corresponding plasmid vectors are also useful in the present invention.

The present invention further includes a genetically modified T lymphocyte, which is transduced with a nucleic acid of the present invention or transduced with the above-mentioned recombinant plasmid containing the nucleic acid of the present invention or a viral system containing the plasmid. Conventional nucleic acid transduction methods in the art, including non-viral and viral transduction methods, can be used in the present invention. Non-viral transduction methods include electroporation and transposon methods. Recently, nucleofector nuclear transfection instrument developed by Amaxa can directly introduce foreign genes into nucleus to achieve highly efficient transduction of target genes. In addition, compared with conventional electroporation, the transduction efficiency of transposon system based on Sleeping Beauty system or PiggyBac transposon was significantly improved. The combination of nucleofector transfection instrument and SB Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10.], and high transduction efficiency and site-directed integration of target genes can be achieved by this method. In one embodiment of the invention, the transduction method of a T lymphocyte modified by a chimeric antigen receptor gene is a transduction method based on a virus such as a retrovirus or a lentivirus. The method has the advantages of high transduction efficiency and stable expression of exogenous gene, and the time for in vitro culturing T lymphocytes to clinical level can be shorten. The transduced nucleic acid is expressed on the surface of the transgenic T lymphocytes by transcription, translation. In vitro cytotoxicity assay performed on various cultured tumor cells demonstrated that the immune effector cells of the present invention have highly specific tumor cell killing effects (also known as cytotoxicity). Therefore, the nucleic acid encoding a chimeric antigen receptor protein of the present invention, a plasmid comprising the nucleic acid, a virus comprising the plasmid, and a transgenic immune effector cells transfected with the nucleic acid, plasmid or virus described above can be effectively used in tumor immunotherapy.

The immune cells of the present invention may also carry exogenous encoding sequences for cytokines, including but not limited to IL-12, IL-15 or IL-21. These cytokines have immunomodulatory or antitumor activity, enhance the function of effector T cells and activated NK cells, or directly exert anti-tumor effects. Therefore, those skilled in the art will understand that the use of these cytokines will help the immune cells to function better.

In addition to the chimeric antigen receptor described above, the immune cells of the present invention may also express another chimeric antigen receptor, which does not contain CD3ζ, but contains intracellular signaling domain of CD28 and intracellular signal domain of CD137, or a combination of both.

The immune cells of the present invention may also express chemokine receptors; the chemokine receptors include, but are not limited to, CCR2. A skilled person will understand that the CCR2 chemokine receptor can competitively bind CCR2 in the body and is beneficial for blocking the metastasis of the tumor.

The immune cells of the present invention may also express siRNAs that can reduce PD-1 expression or PD-L1-blocking proteins. A skilled person will understand that competitive blocking of the interaction between PD-L1 and its receptor PD-1 will facilitate the recovery of anti-tumor T-cell responses, thereby inhibiting tumor growth.

The immune cells of the present invention may also express a safety switch; preferably, the safety switch includes iCaspase-9, Truancated EGFR or RQR8.

Pharmaceutical Composition

The antibodies, immunoconjugates comprising the antibodies, and genetically modified immune cells of the present invention can be used in the preparation of a pharmaceutical composition or diagnostic reagent. In addition to an effective amount of the antibody, immunological conjugate, or immune cell, the composition may further comprise a pharmaceutically acceptable carrier. The term "pharmaceutically acceptable" means that when the molecular entities and compositions are properly administered to animals or humans, they do not cause adverse, allergic or other untoward reactions.

Specific examples of some of the substances which may be used as pharmaceutically acceptable carriers or components thereof are sugars, such as lactose, dextrose and sucrose; starches, such as corn starch and potato starch; cellulose and its derivatives, such as carboxymethylcellulose sodium, ethylcellulose and methylcellulose; gum tragacanth; malt; gelatin; talc; solid lubricants such as stearic acid and magnesium stearate; calcium sulfate; vegetable oils, such as peanut oil, cottonseed oil, sesame oil, olive oil, corn oil and cocoa butter; polyhydric alcohols such as propylene glycol, glycerin, sorbitol, mannitol and polyethylene glycol; alginic acid; emulsifiers such as Tween®; wetting agents such as sodium lauryl sulfate; coloring agents; flavoring agents; tablets, stabilizers; antioxidants; preservatives; pyrogen-free water; isotonic saline solutions; and phosphate buffers and the like.

The composition of the present invention can be prepared into various dosage forms as needed, and the dosage to be administered to a patient can be determined by a physician according to factors, such as type, age, body weight, and general disease condition of a patient, mode of administration, and the like. For example, injection or other treatment may be used.

The present invention is further described below with reference to specific embodiments. It should be understood that these examples are only for illustrating the present invention and are not intended to limit the scope of the present invention. Experimental procedures in the following examples where no specific conditions are indicated are generally carried out in accordance with the conditions described in customary conditions such as those compiled by J. Sambrook et al., Molecular Cloning Experiments Guide, Third Edition, Science Press, 2002, or according to the manufacturer Suggested conditions.

Example 1. Construction of Affinity Mature Library of Single Chain Antibody 7B3

The single chain antibody 7B3 is a humanized antibody fragment that specifically recognizes a cryptic epitope ($^{287}$CGADSYEMEEDGVRKC$^{302}$ (SEQ ID NO: 1)) formed from the amino acid sequence of positions 287-302 of EGFR exposed in tumor cells. The nucleotide sequences of VL and VH genes were obtained from the sequences SEQ ID NO: 14 and SEQ ID NO: 13 as shown in patent application 201210094008.x and linked in the order of VL7B3-linker-VH7B3.

Nucleotide sequence (717 base pairs, SEQ ID NO: 2) of single chain antibody 7B3:

```
GATATTCAGATGACCCAGAGCCCGAGCAGCCTGAGCGCGAGCGTGGGCGA
CCGTGTGACCATTACCTGCCATGCGAGCCAGGATATTAACAGCAACATTG
GCTGGCTGCAGCAGAAACCGGGCAAAGCGTTTAAAGGCCTGATTTATCAT
GGCAAAAACCTGGAAGATGGCGTGCCGAGCCGTTTTAGCGGCAGCGGCAG
CGGCACCGATTTTACCCTGACCATTAGCAGCCTGCAGCCGGAAGATTTTG
CGACCTATTATTGCGTTCAGTACGCCCAGTTCCCATATACATTTGGCCAG
GGCACCAAAGTGGAAATTAAACGTGGTGGAGGCGGTTCAGGCGGAGGTGG
CTCTGGCGGTGGCGGATCGGATGTGCAGCTGGTGGAAAGCGGCGGCGGCC
TGGTGCAGCCGGGCGGCAGCCTGCGTCTGAGCTGCGCGGTGAGCGGCTAT
AGCATTACCAGCGATTATGCGTGGAACTGGATTCGTCAGGCGCCGGGCAA
AGGCCTGGAATGGCTGGGCTATATTAGCTATCGTGGCCGCACCAGCTATA
ACCCGAGCCTGAAAAGCCGTATTAGCATTACCCGTGATAACAGCAAAAAC
ACCTTTTTCCTGCAGCTGAACAGCCTGCGTGCGGAAGATACCGCGGTGTA
TTATTGCGCGCGCCTGGGACGCGGCTTCCGCTACTGGGGCCAGGGCACCC
TGGTGACCGTGAGCAGC
```

The amino acid sequence of the single chain antibody 7B3 (239 amino acids, SEQ ID NO: 3; underlined area was 7B3 VL CDR1, CDR2, CDR3, 7B3 VH CDR1, CDR2, CDR3, respectively):

```
DIQMTQSPSSLSASVGDRVTITCHASQDINSNIGWLQQKPGKAFKGLIYH
GKNLEDGVPSRFSGSGSGTDFTLTISSLQPEDFATYYCVQYAQFPYTFGQ
GTKVEIKRGGGGSGGGGSGGGGSDVQLVESGGGLVQPGGSLRLSCAVSGY
```

-continued

SITSDYAWNWIRQAPGKGLEWLGYISYRGRTSYNPSLKSRISITRDNSKN

TFFLQLNSLRAEDTAVYYCARLGRGFRYWGQGTLVTVSS

For enhancing the ability of 7B3 single-chain antibody to bind EGFR, some amino acids in
CDR3 of light chain and CDR3 of heavy chain were randomly mutated and corresponding mature libraries were constructed.

1. Construction of 7B3 Light Chain CDR3 Affinity Mature Library

By sequence alignment and analysis of 7B3 single-chain antibody, part of the amino acids in the third CDR region of 7B3 light chain were selected and randomized mutations were introduced by primers to construct a light-chain affinity mature library.

To prepare a DNA fragment encoding the 7B3 mutant library, two DNA fragments were respectively obtained by PCR using plasmid pCantab 5E-7B3 (inserting 7B3 into sfiI/NotI site of pCantab 5E-7B3) as a template, followed by splicing through bypass PCR method. Specifically, the following procedure was used: for synthesizing genes, PCR reactions were performed in a volume of 50 μl each using plasmid pCantab 5E-7B3 as a template with a final concentration of 0.2 μM for each primer and 5 μl of 10×KOD Plus buffer, 4 μl dNTPs (dATP, dCTP, dGTP and dTTP, 2 mM each), 2 μl 25 mM MgSO$_4$ and 1 U KOD Plus (from Takara) were added and the PCR procedure was started in a thermal cycler after making up the volume with water. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The first fragment was amplified using primers pC7B3fw (SEQ ID NO: 4, ATAACAGGCCCAGCCGGC-CATGGATATTCAGATGACCCAGAG) and LR3re (SEQ ID NO: 5, CACTTTGGTGCCCTGGCCAAATGTMN-NTGGGNNMNNMNNMNNCTGMNNGCAATA ATAGGTCGCAAAATC) and the second fragment was amplified using primer LR3f2fw (SEQ ID NO: 6, ACAT-TTGGCCAGGGCACCAAAG) and pC7B3re (SEQ ID NO: 7, ATAAATGCGGCC GCGCTGCTCACGGTCAC).

Expected PCR products were identified by analytical agarose gel electrophoresis and purified from samples by Wizard SV Gel and PCR Clean-up Kit (available from Promega). The two fragments were added in equimolar ratio to a second round of bridge PCR as a template and the reaction system still used KOD Plus system mentioned above. The reaction was firstly heated to 94° C. for 5 minutes and then incubated for 10 cycles, each cycling reaction conditions were 94° C. for 30 seconds, 60° C. for 30 seconds and 68° C. for 30 seconds, and finally, at 68° C. for 10 minutes. Subsequently, primers pC7B3fw and pC7B3re were directly added to the reaction system at a final concentration of 0.2 μM, and the PCR program was started. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The expected PCR products were separated by preparative agarose gel electrophoresis and purified by Wizard SV Gel and PCR Clean-up kits according to the manufacturer's instructions.

In the library, complete DNA fragments contained sfiI and NotI restriction enzyme recognition sites at each end, and was digested by restriction endonuclease sfiI/NotI (purchased from New England Biolabs) for restriction digestion and inserted into phagemid vector pCANTAB 5E digested by the same two enzymes. Ligation products were isolated and desalted using Wizard SV Gel and PCR Clean-up Kit for electrotransformation. For electrotransformation, a home-made competent E. coli ER2738 (available from New England Biolabs) was used with electroporation cuvette and electroporation instrument Gene Pulser II (from Bio-Rad). A library containing 1.9×10$^9$ mutants was finally confirmed.

2. Construction of 7B3 Heavy Chain CDR3 Affinity Mature Library

By sequence alignment and analysis of 7B3 single-chain antibody, part of the amino acids in the third CDR region of 7B3 heavy chain were selected and randomized mutations were introduced by primers to construct a heavy-chain affinity mature library.

To prepare a DNA fragment encoding the 7B3 mutant library, two DNA fragments were respectively obtained by PCR using plasmid pCantab 5E-7B3 as a template, followed by splicing through bypass PCR method. Specifically, the following procedure was used: for synthesizing genes, PCR reactions were performed in a volume of 50 μl each using plasmid pCantab 5E-7B3 as a template with a final concentration of 0.2 μM for each primer and 5 μl of 10 x KOD Plus buffer, 4 μl dNTPs (dATP, dCTP, dGTP and dTTP, 2 mM each), 2 μl 25 mM MgSO$_4$ and 1 U KOD Plus were added and the PCR procedure was started in a thermal cycler after making up the volume with water. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The first fragment was amplified using primers HR3f1fw (SEQ ID NO: 8, TCGCAATTCCTTTAGTTGTTCC) and HR3f1 re (SEQ ID NO: 9, CAGGGTGCCCTGGCCCCAG-TAANNMNNMNNMNNMNNMNNGCGCGCGCAATA-ATAC AC) and the second fragment was amplified using primer HR3f2fw (SEQ ID NO: 10, TACTGGGGCCAGGGCACCCTG) 和 HR3f2re (SEQ ID NO: 11, GGAATAGGTGTATCACCGTACTCAG).

Expected PCR products were identified by analytical agarose gel electrophoresis and purified from samples by Wizard SV Gel and PCR Clean-up Kit. The two fragments were added in equimolar ratio to a second round of bridge PCR as a template and the reaction system still used KOD Plus system mentioned above. The reaction was firstly heated to 94° C. for 5 minutes and then incubated for 10 cycles, each cycling reaction conditions were 94° C. for 30 seconds, 60° C. for 30 seconds and 68° C. for 30 seconds, and finally, at 68° C. for 10 minutes. Subsequently, primers HR3f1fw and HR3f2re were directly added to the reaction system at a final concentration of 0.2 μM, and the PCR program was started. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The expected PCR products were separated by preparative agarose gel electrophoresis and purified by Wizard SV Gel and PCR Clean-up kits according to the manufacturer's instructions.

In the library, complete DNA fragments contained sfiI and NotI restriction enzyme recognition sites at each end, and was digested by restriction endonuclease sfiI/NotI for restriction digestion and inserted into phagemid vector pCANTAB 5E digested by the same two enzymes. Ligation products were isolated and desalted using Wizard SV Gel and PCR Clean-up Kit for electrotransformation. For electrotransformation, a home-made competent E. coli ER2738 was used with electroporation cuvette and electroporation instrument Gene Pulser II. A library containing 6.0×10⁹ mutants was finally confirmed.

Example 2. Screening Against EGFRvIII by Using 7B3 Affinity Maturation Library

To obtain 7B3 mutants with higher affinity, four rounds of screening were performed using light chain and heavy chain mutant libraries, respectively, as follows: a corresponding phage library was obtained from the above library through infection of helper phage M13KO7. The phage library was incubated with the biotin-labeled antigen EGFRvIII (purchased from Shanghai raygene biotechnology Co., LTD) for 2 hours at room temperature and then incubated with 2% (w/v) BSA (bovine serum albumin, purchased from Shanghai Bioengineering)-blocked streptavidin magnetic beads MyOne C1 (from Invitrogen) at room temperature for 30 minutes. The beads were then washed with PBST (containing 0.1% Tween-20) buffer to remove phage not specifically bound or with weaker binding capacity. Strongly binding phages were eluted from magnetic beads with glycine-HCl (pH 2.2), neutralized with Tris neutralizing solution (pH 9.1), and then used to infect $E.\ coli$ ER2738 in the mid-logarithmic growth phase for the next round of screening.

In the above described four rounds of screening, the amounts of magnetic beads were 50 μl, 10 μl and 10 μl, the concentrations of biotin-labeled antigen EGFRvIII were 10 nM, 1 nM, 0.5 nM and 0.1 nM, respectively, and PBST was used for washing for 10, 10, 15 and 20 times. From the second round of screening, 50-, 500-, and 1000-fold excess of unlabeled antigen EGFRvIII, respectively, was added as a competitor prior to elution to remove mutants with weaker binding capacity.

For the production of phage displaying 7B3 single chain antibody mutants on the surface, the strain in glycerol obtained in Example 1 was inoculated into 400 ml of 2YT/ampicillin medium to bring the cell density to $OD_{600}$=0.1, and at 37° C. and 200 rpm, cultured with shaking until the cell density reached $OD_{600}$=0.5·10¹² pfu of M13KO7 helper phage was used in infection and incubated at 30° C. and 50 rpm for 30 minutes. After adding 50 mg/l kanamycin and shaking at 37° C. and 200 rpm for 30 minutes, the pellet was separated by centrifugation (15 minutes, 1600×g, 4° C.) and resuspended in 400 ml 2YT/ampicillin/Kanamycin medium and cultured for 16 hours at 37° C. with shaking at 200 rpm. Finally, the pellet was separated by centrifugation (5000 rpm, 4° C. for 20 minutes) and discarded. The supernatant was filtered through a 0.45 μm filter and ¼ volume of 20% (w/v) PEG 8000, 2.5 M NaCl solution was added and incubated in an ice bath for 1 hour for precipitating phage pellets. The pellet was then centrifuged (20 min, 8000×g, 4° C.) and the supernatant was discarded. The phage was resuspended in 25 ml of prechilled PBS (137 mM NaCl, 2.7 mM KCl, 8 mM $Na_2HPO_4$, 2 mM $KH_2PO_4$) and centrifuged (5 minutes, 20000×g, 4° C.). ¼ volume of 20% (w/v) PEG 8000, 2.5 M NaCl solution was added to the supernatant and incubated in an ice bath for 30 minutes for precipitating the phage particles again. The pellet was obtained by centrifugation (30 min at 20000×g at 4° C.), resuspended in 2 ml of prechilled PBS again, kept on ice for 30 min and centrifuged (30 min, 17000×g, 4° C.). The supernatant was mixed with 4% (w/v) BSA in PBS at 1:1, placed on a rotary mixer and incubated for 30 minutes at room temperature, and then used directly in screening.

Example 3. Identification of 7B3 Mutants Specifically Binding to EGFRvIII

After four rounds of screening against EGFRvIII antigen, 96 clones were randomly selected from the clones obtained in the fourth round of screening and analyzed for their combination with antigens EGFRvIII and N1N2-806 (purchased from Shanghai raygene biotechnology Co., LTD) using single phage ELISA (enzyme-linked immunosorbent assay), where N1N2-806 is a fusion protein of N1N2 domain of M13 phage PIII protein and amino acids at positions 287-302 of EGFR. For this purpose, each single colony was inoculated into 300 μl of 2YT/ampicillin medium (containing 2% glucose) in a 96-well deep-well plate and cultured with shaking at 37° C. and 250 rpm for 16 hours. 20 μl of culture was innoculated into 500 μl of 2YT/ampicillin medium (containing 0.1% glucose) and shaken at 37° C. and 250 rpm for 1.5 hours. To prepare the helper phage solution, 75 μl of M13KO7 (titer of 3×10¹² pfu/ml) was taken and mixed into 15 ml of 2YT medium and added into a plate at 50 μl/well. Incubation was performed at 37° C. and 150 rpm for 30 minutes, and then 50 μl/well of prepared kanamycin solution (180 μl of 50 mg/ml kanamycin taken and added into 15 ml of 2YT medium) was added and cultured at 37° C. and 250 rpm for 16 hours with shaking. Finally, the cells were precipitated by centrifugation (30 minutes at 5000×g, 4° C.) and the supernatant was transferred to a new 96-well deep-well plate.

To perform single-phage ELISA, 100 ng/well of antigen EGFRvIII, N1N2-806 and negative control proteins BSA and N1N2 (purchased from Shanghai raygene biotechnology Co., LTD) were used on 96-well MediSorp ELISA plate (purchased from Nunc) at 50 μl/well, and coated overnight at 4° C. Each well was blocked with PBST containing 2% BSA (w/v). The wells were then washed with PBST for three times. Then, each phage solution prepared above was added to each well of the plate at 100 μl/well. After incubation for 2 hours at 37° C., it was washed for three times with PBST. To detect bound phage, anti-M13 antibody superoxide dismutase conjugate (purchased from GE Healthcare) was diluted at 1:5000 in PBST and 100 μl was added to each well. After incubating at 37° C. for 1 hour, the wells were rinsed for three times with PBST and then rinsed for three times with PBS. Finally, 50 μl of TMB substrate was added into the wells and developed for 10 minutes at room temperature, followed by addition of 50 μl of 2M $H_2SO_4$ per well to stop the color reaction. Extinction values were measured at 450 nm with an enzyme-linked immunosorbent (Bio-Rad).

Clones with stronger signal of binding antigen instead of BSA in ELISA were selected and used in subsequent evaluation and sequencing analysis. The antibodies obtained from the light chain affinity maturation library were then further combined with the antibodies obtained from Example 2 in the heavy chain affinity maturation library on light chain variable region sequence and heavy chain variable region sequence and the resulting antibodies are also capable of specifically binding antigens EGFRvIII and N1N2-806, instead of the control proteins BSA and N1N2.

From the crystal structure of the antibody and antigenic determinant, the binding of combined antibodies obtained from 7B3 light and heavy chain mutations and $EGFR_{287-302}$ was structurally analyzed, and finally, some amino acid positions were selected for further mutation for higher affinity and stability. All of the altered amino acid positions include S31 in the light chain CDR1 region, V89, A92, Q93, F94 and Y96 in the light chain CDR3 region, 5182 in the heavy chain CDR2 region, L222, R224, G225, F226 and R227 in the heavy chain CDR3 region. Based on the sequences of combined antibodies after mutagenesis of the light and heavy chains, the mutation sites were further introduced to obtain the antibody Y022. Compared with the parental antibody 7B3, Y022 contains 12 amino acid mutation sites (S31V, V89N, A92E, Q93N, F94I, Y96L, S182Q, L222M, R224K, G225N, F226W, and R227D). As shown in FIG. 1, in a single phage ELISA assay, Y022 was able to specifically bind to antigens EGFRvIII and N1N2-806 without binding to control proteins BSA and N1N2.

Nucleotide sequence of single chain antibody Y022 (717 bases; SEQ ID NO: 12):

GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAGCGTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATATCCCACTGACATTTGGCCAG

GGCACCAAAGTGGAAATTAAACGT<u>GGTGGAGGCGGTTCAGGCGGAGGTGG</u>

<u>CTCTGGCGGTGGCGGATCG</u>GATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCCAGTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCATGGGTAAGAATTGGGATTACTGGGGCCAGGGCACCC

TGGTGACCGTGAGCAGC

Amino acid sequence of single chain antibody Y022 (239 amino acids; SEQ ID NO: 13):

DIQMTQSPSSLSASVGDRVTITC<u>HASQDINVN</u>IGWLQQKPGKAFKGLIY<u>H</u>

<u>GKNLED</u>GVPSRFSGSGSGTDFTLTISSLQPEDFATYYC<u>NQYENIPLT</u>FGQ

GTKVEIKR*GGGGSGGGGSGGGGS*DVQLVESGGGLVQPGGSLRLSCAVS<u>GY</u>

<u>SITSDYAWN</u>WIRQAPGKGLEWLG<u>YISYRGRTQYNPSLKS</u>RISITRDNSKN

TFFLQLNSLRAEDTAVYYCAR<u>MGKNWDY</u>WGQGTLVTVSS

Wherein the light chain is in positions 1-108 and the light chain CDR1 sequence: HASQDINVNIG (SEQ ID NO: 41), CDR2 sequence: HGKNLED (SEQ ID NO: 42), CDR3 sequence: NQYENIPLT (SEQ ID NO: 43).

Wherein the heavy chain is in positions 124-239 and the heavy chain CDR1 sequence: GYSITSDYAWN (SEQ ID NO: 44), CDR2 sequence: YISYRGRTQYNPSLKS (SEQ ID NO: 45), CDR3 sequence: MGKNWDY (SEQ ID NO: 46).

Since it was screened in the mutant library constructed previously and subjected to site-directed mutagenesis, the nucleotide sequence of Y022 was contained in pCantab 5E, named as pCantab 5E-Y022 plasmid.

The inventors also obtained 10 additional antibody clones with significantly improved affinity and stability using the same method as for the production of antibody Y022, namely M14, M15, M25, M26, S7, S8, S17, S22, S23 and S29. Compared with the parent antibody 7B3, all single-chain antibodies contained amino acid mutation sites as shown in Table 1.

TABLE 1

| Antibody | amino acid mutation site |
|---|---|
| Y022 | S31V, V89N, A92E, Q93N, F94I, Y96L, S182Q, L222M, R224K, G225N, F226W, R227D |
| M14 | V89N, A92E, Q93N, F94N, Y96I, S182N |
| M15 | S31V, V89N, A92E, Q93N, F94N, Y96I |
| M25 | S31V, V89N, A92E, Q93N, F94I, Y96L, S182R |
| M26 | S31V, V89N, A92E, Q93N, F94I, Y96L, S182Q |
| S7 | S31V, K53T, V89N, A92E, Q93N, F94N, Y96I |
| S8 | S31V, A44S, V89N, A92E, Q93N, F94N, Y96I |
| S17 | S31T, V89N, A92E, Q93N, F94N, Y96L, S182Q |
| S22 | S31V, K53T, V89N, A92E, Q93N, F94N, Y96L, S182R |
| S23 | S31V, A44S, V89N, A92E, Q93N, F94N, Y96L, S182R |
| S29 | S31V, V89N, A92E, Q93N, Y96L, S182R |

Nucleotide sequence of single chain antibody M14 (717 bases; SEQ ID NO: 58):

GATATTCAGATGACCCAGAGCCCGAGCAGCCTGAGCGCGAGCGTGGGCGA

CCGTGTGACCATTACCTGCCATGCGAGCCAGGATATTAACAGCAACATTG

GCTGGCTGCAGCAGAAACCGGGCAAAGCGTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCAATTACATTTGGCCAG

GGCACCAAAGTGGAAATTAAACGT<u>GGTGGAGGCGGTTCAGGCGGAGGTGG</u>

<u>CTCTGGCGGTGGCGGATCG</u>GATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCAACTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC

Amino acid sequence of single chain antibody M14 (239 amino acids; SEQ ID NO: 59):

```
DIQMTQSPSSLSASVGDRVTITCHASQDINSNIGWLQQKPGKAFKGLIYHGKNLEDGVPS

RFSGSGSGTDFTLTISSLQPEDFATYYCNQYENNPITFGQGTKVEIKRGGGGSGGGGSGG

GGSDVQLVESGGGLVQPGGSLRLSCAVSGYSITSDYAWNWIRQAPGKGLEWLGYISYRGR

TNYNPSLKSRISITRDNSKNTFFLQLNSLRAEDTAVYYCARLGRGFRYWGQGTLVTVSS
```

Amino acid sequences of M14 light chain CDR1(HASQDINSNIG), CDR2(HGKNLED), CDR3(NQYENNPIT) and heavy chain CDR1 (GYSITSDYAWN), CDR2 (YISYRGRTNYNPSLKS), CDR3 (LGRGFRY) are SEQ ID NO: 47, 42, 48, 44, 49, 50, respectively.

Nucleotide sequence of single chain antibody M15 (717 bases; SEQ ID NO: 60):

```
GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAGCGTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCAATTACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCAGCTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC
```

Amino acid sequence of single chain antibody M15 (239 amino acids; SEQ ID NO: 61):

```
DIQMTQSPSSLSASVGDRVTITCHASQDINSNIGWLQQKPGKAFKGLIYHGKNLEDGVPS

RFSGSGSGTDFTLTISSLQPEDFATYYCNQYENNPITFGQGTKVEIKRGGGGSGGGGSGG

GGSDVQLVESGGGLVQPGGSLRLSCAVSGYSITSDYAWNWIRQAPGKGLEWLGYISYRGR

TNYNPSLKSRISITRDNSKNTFFLQLNSLRAEDTAVYYCARLGRGFRYWGQGTLVTVSS
```

Amino acid sequences of M15 light chain CDR1 (HASQDINVNIG), CDR2 (HGKNLED), CDR3 (NQYENNPIT) and heavy chain CDR1 (GYSITSDYAWN), CDR2 (YISYRGRTSYNPSLKS), CDR3 (LGRGFRY) are SEQ ID NO: 41, 42, 48, 44, 51, 50, respectively.

Nucleotide sequence of single chain antibody M25 (717 bases; SEQ ID NO: 62):

```
GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAGCGTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATATCCCACTGACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCCGCTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC
```

Amino acid sequence of single chain antibody M25 (239 amino acids; SEQ ID NO: 63):

```
DIQMTQSPSSLSASVGDRVTITCHASQDINVNIGWLQQKPGKAFKGLIYHGKNLEDGVPS

RFSGSGSGTDFTLTISSLQPEDFATYYCNQYENIPLTFGQGTKVEIKRGGGGSGGGGSGG

GGSDVQLVESGGGLVQPGGSLRLSCAVSGYSITSDYAWNWIRQAPGKGLEWLGYISYRGR

TRYNPSLKSRISITRDNSKNTFFLQLNSLRAEDTAVYYCARLGRGFRYWGQGTLVTVSS
```

```
DIQMTQSPSSLSASVGDRVTITCHASQDINVNIGWLQQKPGKAFKGLIYHGKNLEDGVPS

RFSGSGSGTDFTLTISSLQPEDFATYYCNQYENIPLTFGQGTKVEIKRGGGGSGGGGSGG

GGSDVQLVESGGGLVQPGGSLRLSCAVSGYSITSDYAWNWIRQAPGKGLEWLGYISYRGR

TRYNPSLKSRISITRDNSKNTFFLQLNSLRAEDTAVYYCARLGRGFRYWGQGTLVTVSS
```

Amino acid sequences of M25 light chain CDR1 (HASQDINVNIG), CDR2 (HGKNLED), CDR3 (NQYENIPLT) and heavy chain CDR1 (GYSITSDYAWN), CDR2 (YISYRGRTRYNPSLKS), CDR3 (LGRGFRY) are SEQ ID NO: 41, 42, 43, 44, 52, 50, respectively.

Nucleotide sequence of single chain antibody M26 (717 bases; SEQ ID NO: 64):

```
GATATTCAGATGACCCAGAGCCCGAGCAGCCTGAGCGCGAGCGTGGGCGA
CCGTGTGACCATTACCTGCCATGCGAGCCAGGATATTAACGTGAACATTG
GCTGGCTGCAGCAGAAACCGGGCAAAGCGTTTAAAGGCCTGATTTATCAT
GGCAAAAACCTGGAAGATGGCGTGCCGAGCCGTTTTAGCGGCAGCGGCAG
CGGCACCGATTTTACCCTGACCATTAGCAGCCTGCAGCCGGAAGATTTTG
CGACCTATTATTGCAATCAGTATGAAAATATCCCACTGACATTTGGCCAG
GGCACCAAAGTGGAAATTAAACGTGGTGGAGGCGGTTCAGGCGGAGGTGG
CTCTGGCGGTGGCGGATCGGATGTGCAGCTGGTGGAAAGCGGCGGCGGCC
TGGTGCAGCCGGGCGGCAGCCTGCGTCTGAGCTGCGCGGTGAGCGGCTAT
AGCATTACCAGCGATTATGCGTGGAACTGGATTCGTCAGGCGCCGGGCAA
AGGCCTGGAATGGCTGGGCTATATTAGCTATCGTGGCCGCACCCAGTATA
ACCCGAGCCTGAAAAGCCGTATTAGCATTACCCGTGATAACAGCAAAAAC
ACCTTTTTCCTGCAGCTGAACAGCCTGCGTGCGGAAGATACCGCGGTGTA
TTATTGCGCGCGCCTGGGACGCGGCTTCCGCTACTGGGGCCAGGGCACCC
TGGTGACCGTGAGCAGC
```

Amino acid sequence of single chain antibody M26 (239 amino acids; SEQ ID NO: 65):

Amino acid sequences of M26 light chain CDR1 (HASQDINVNIG), CDR2 (HGKNLED), CDR3 (NQYENIPLT) and heavy chain CDR1 (GYSITSDYAWN), CDR2 (YISYRGRTQYNPSLKS), CDR3 (LGRGFRY) are SEQ ID NO: 41, 42, 43, 44, 45, 50, respectively.

Nucleotide sequence of single chain antibody S7 (717 bases; SEQ ID NO: 66):

```
GATATTCAGATGACCCAGAGCCCGAGCAGCCTGAGCGCGAGCGTGGGCGA
CCGTGTGACCATTACCTGCCATGCGAGCCAGGATATTAACGTGAACATTG
GCTGGCTGCAGCAGAAACCGGGCAAAGCGTTTAAAGGCCTGATTTATCAT
GGCACCAACCTGGAAGATGGCGTGCCGAGCCGTTTTAGCGGCAGCGGCAG
CGGCACCGATTTTACCCTGACCATTAGCAGCCTGCAGCCGGAAGATTTTG
CGACCTATTATTGCAATCAGTATGAAAATAACCCAATTACATTTGGCCAG
GGCACCAAAGTGGAAATTAAACGTGGTGGAGGCGGTTCAGGCGGAGGTGG
CTCTGGCGGTGGCGGATCGGATGTGCAGCTGGTGGAAAGCGGCGGCGGCC
TGGTGCAGCCGGGCGGCAGCCTGCGTCTGAGCTGCGCGGTGAGCGGCTAT
AGCATTACCAGCGATTATGCGTGGAACTGGATTCGTCAGGCGCCGGGCAA
AGGCCTGGAATGGCTGGGCTATATTAGCTATCGTGGCCGCACCAGCTATA
ACCCGAGCCTGAAAAGCCGTATTAGCATTACCCGTGATAACAGCAAAAAC
ACCTTTTTCCTGCAGCTGAACAGCCTGCGTGCGGAAGATACCGCGGTGTA
TTATTGCGCGCGCCTGGGACGCGGCTTCCGCTACTGGGGCCAGGGCACCC
TGGTGACCGTGAGCAGC
```

Amino acid sequence of single chain antibody S7 (239 amino acids; SEQ ID NO: 67):

```
DIQMTQSPSSLSASVGDRVTITCHASQDINVNIGWLQQKPGKAFKGLIYHGKNLEDGVPS

RFSGSGSGTDFTLTISSLQPEDFATYYCNQYENIPLTFGQGTKVEIKRGGGGSGGGGSGG

GGSDVQLVESGGGLVQPGGSLRLSCAVSGYSITSDYAWNWIRQAPGKGLEWLGYISYRGR

TQYNPSLKSRISITRDNSKNTFFLQLNSLRAEDTAVYYCARLGRGFRYWGQGTLVTVSS
```

```
DIQMTQSPSSLSASVGDRVTITCHASQDINVNIGWLQQKPGKAFKGLIYHGTNLEDGVPS

RFSGSGSGTDFTLTISSLQPEDFATYYCNQYENNPITFGQGTKVEIKRGGGGSGGGGSGG

GGSDVQLVESGGGLVQPGGSLRLSCAVSGYSITSDYAWNWIRQAPGKGLEWLGYISYRGR

TSYNPSLKSRISITRDNSKNTFFLQLNSLRAEDTAVYYCARLGRGFRYWGQGTLVTVSS
```

Amino acid sequences of S7 light chain CDR1 (HASQDINVNIG), CDR2 (HGTNLED), CDR3 (NQYENNPIT) and heavy chain CDR1 (GYSITSDYAWN), CDR2 (YISYRGRTSYNPSLKS), CDR3 (LGRGFRY) are SEQ ID NO: 41, 53, 54, 44, 51, 50, respectively.

Nucleotide sequence of single chain antibody S8 (717 bases; SEQ ID NO: 68):

```
GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAAGCTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCAATTACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCAGCTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC
```

Amino acid sequence of single chain antibody S8 (239 amino acids; SEQ ID NO: 69):

Amino acid sequences of S8 light chain CDR1 (HASQDINVNIG), CDR2 (HGKNLED), CDR3 (NQYENNPIT) and heavy chain CDR1 (GYSITSDYAWN), CDR2 (YISYRGRTSYNPSLKS), CDR3 (LGRGFRY) are SEQ ID NO: 41, 42, 54, 44, 51, 50, respectively.

Nucleotide sequence of single chain antibody S17 (717 bases; SEQ ID NO: 70):

```
GATATTCAGATGACCCAGAGCCCGAGCAGCCTGAGCGCGAGCGTGGGCGA

CCGTGTGACCATTACCTGCCATGCGAGCCAGGATATTAACACCAACATTG

GCTGGCTGCAGCAGAAACCGGGCAAAGCGTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCACTGACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCCAGTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC
```

Amino acid sequence of single chain antibody S17 (239 amino acids; SEQ ID NO: 71):

```
DIQMTQSPSSLSASVGDRVTITCHASQDINTNIGWLQQKPGKAFKGLIYHGKNLEDGVPS

RFSGSGSGTDFTLTISSLQPEDFATYYCNQYENNPLTFGQGTKVEIKRGGGGSGGGGSGG

GGSDVQLVESGGGLVQPGGSLRLSCAVSGYSITSDYAWNWIRQAPGKGLEWLGYISYRGR

TQYNPSLKSRISITRDNSKNTFFLQLNSLRAEDTAVYYCARLGRGFRYWGQGTLVTVSS
```

DIQMTQSPSSLSASVGDRVTITCHASQDINTNIGWLQQKPGKAFKGLIYHGKNLEDGVPS

RFSGSGSGTDFTLTISSLQPEDFATYYCNQYENNPLTFGQGTKVEIKRGGGGSGGGGSGG

GGSDVQLVESGGGLVQPGGSLRLSCAVSGYSITSDYAWNWIRQAPGKGLEWLGYISYRGR

TQYNPSLKSRISITRDNSKNTFFLQLNSLRAEDTAVYYCARLGRGFRYWGQGTLVTVSS

Amino acid sequences of S17 light chain CDR1 (HASQDINTNIG), CDR2 (HGKNLED), CDR3 (NQYENNPLT) and heavy chain CDR1 (GYSITSDYAWN), CDR2 (YISYRGRTQYNPSLKS), CDR3 (LGRGFRY) are SEQ ID NO: 55, 42, 56, 44, 45, 50, respectively.

Nucleotide sequence of single chain antibody S22 (717 bases; SEQ ID NO: 72):

GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAGCGTTTAAAGGCCTGATTTATCAT

GGCACCAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCACTGACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCCGCTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC

Amino acid sequence of single chain antibody S22 (239 amino acids; SEQ ID NO: 73):

Amino acid sequences of S22 light chain CDR1 (HASQDINVNIG), CDR2 (HGTNLED), CDR3 (NQYENNPLT) and heavy chain CDR1 (GYSITSDYAWN), CDR2 (YISYRGRTRYNPSLKS), CDR3 (LGRGFRY) are SEQ ID NO: 41, 53, 56, 44, 52, 50, respectively.

Nucleotide sequence of single chain antibody S23 (717 bases; SEQ ID NO: 74):

GATATTCAGATGACCCAGAGCCCGAGCAGCCTGAGCGCGAGCGTGGGCGA

CCGTGTGACCATTACCTGCCATGCGAGCCAGGATATTAACGTGAACATTG

GCTGGCTGCAGCAGAAACCGGGCAAAAGCTTTAAAGGCCTGATTTATCAT

GGCAAAAACCTGGAAGATGGCGTGCCGAGCCGTTTTAGCGGCAGCGGCAG

CGGCACCGATTTTACCCTGACCATTAGCAGCCTGCAGCCGGAAGATTTTG

CGACCTATTATTGCAATCAGTATGAAAATAACCCACTGACATTTGGCCAG

GGCACCAAAGTGGAAATTAAACGTGGTGGAGGCGGTTCAGGCGGAGGTGG

CTCTGGCGGTGGCGGATCGGATGTGCAGCTGGTGGAAAGCGGCGGCGGCC

TGGTGCAGCCGGGCGGCAGCCTGCGTCTGAGCTGCGCGGTGAGCGGCTAT

AGCATTACCAGCGATTATGCGTGGAACTGGATTCGTCAGGCGCCGGGCAA

AGGCCTGGAATGGCTGGGCTATATTAGCTATCGTGGCCGCACCCGCTATA

ACCCGAGCCTGAAAAGCCGTATTAGCATTACCCGTGATAACAGCAAAAAC

ACCTTTTTCCTGCAGCTGAACAGCCTGCGTGCGGAAGATACCGCGGTGTA

TTATTGCGCGCGCCTGGGACGCGGCTTCCGCTACTGGGGCCAGGGCACCC

TGGTGACCGTGAGCAGC

Amino acid sequence of single chain antibody S23 (239 amino acids; SEQ ID NO: 75):

DIQMTQSPSSLSASVGDRVTITCHASQDINVNIGWLQQKPGKAFKGLIYHGTNLEDGVPS

RFSGSGSGTDFTLTISSLQPEDFATYYCNQYENNPLTFGQGTKVEIKRGGGGSGGGGSGG

GGSDVQLVESGGGLVQPGGSLRLSCAVSGYSITSDYAWNWIRQAPGKGLEWLGYISYRGR

TRYNPSLKSRISITRDNSKNTFFLQLNSLRAEDTAVYYCARLGRGFRYWGQGTLVTVSS

```
DIQMTQSPSSLSASVGDRVTITCHASQDINVNIGWLQQKPGKSFKGLIYHGKNLEDGVPS

RFSGSGSGTDFTLTISSLQPEDFATYYCNQYENNPLTFGQGTKVEIKRGGGGSGGGGSGG

GGSDVQLVESGGGLVQPGGSLRLSCAVSGYSITSDYAWNWIRQAPGKGLEWLGYISYRGR

TRYNPSLKSRISITRDNSKNTFFLQLNSLRAEDTAVYYCARLGRGFRYWGQGTLVTVSS
```

Amino acid sequences of S23 light chain CDR1 (HASQDINVNIG), CDR2 (HGKNLEDG), CDR3 (NQYENNPLT) and heavy chain CDR1 (GYSITSDYAWN), CDR2 (YISYRGRTRYNPSLKS), CDR3 (LGRGFRY) are SEQ ID NO: 41, 42, 56, 44, 52, 50, respectively.

Nucleotide sequence of single chain antibody S29 (717 bases; SEQ ID NO: 76):

```
GATATTCAGATGACCCAGAGCCCGAGCAGCCTGAGCGCGAGCGTGGGCGA
CCGTGTGACCATTACCTGCCATGCGAGCCAGGATATTAACGTGAACATTG
GCTGGCTGCAGCAGAAACCGGGCAAAGCGTTTAAAGGCCTGATTTATCAT
GGCAAAAACCTGGAAGATGGCGTGCCGAGCCGTTTTAGCGGCAGCGGCAG
CGGCACCGATTTTACCCTGACCATTAGCAGCCTGCAGCCGGAAGATTTTG
CGACCTATTATTGCAATCAGTATGAAAATTTCCCACTGACATTTGGCCAG
GGCACCAAAGTGGAAATTAAACGTGGTGGAGGCGGTTCAGGCGGAGGTGG
CTCTGGCGGTGGCGGATCGGATGTGCAGCTGGTGGAAAGCGGCGGCGGCC
TGGTGCAGCCGGGCGGCAGCCTGCGTCTGAGCTGCGCGGTGAGCGGCTAT
AGCATTACCAGCGATTATGCGTGGAACTGGATTCGTCAGGCGCCGGGCAA
AGGCCTGGAATGGCTGGGCTATATTAGCTATCGTGGCCGCACCCGCTATA
ACCCGAGCCTGAAAAGCCGTATTAGCATTACCCGTGATAACAGCAAAAAC
ACCTTTTTCCTGCAGCTGAACAGCCTGCGTGCGGAAGATACCGCGGTGTA
TTATTGCGCGCGCCTGGGACGCGGCTTCCGCTACTGGGGCCAGGGCACCC
TGGTGACCGTGAGCAGC
```

Amino acid sequence of single chain antibody S29 (239 amino acids; SEQ ID NO: 77):

Example 4. Expression and Purification of Antibody

Genes of each antibody were inserted into NdeI/XhoI site of the expression vector pET22B(+), antibody proteins were recombinantly produced in *E. coli* BL21 (DE3) and purified by nickel columns using polypeptides with carboxy-terminal fused 6×histidine. In particular, to prepare the antibody protein, each single colony was inoculated into 5 ml of 2×YT/ampicillin medium and cultured with shaking at 37° C. and 220 rpm for 16 hours. 1 ml of this preculture was used to inoculate 100 ml of 2×YT/ampicillin medium and cultured with shaking at 37° C. and 220 rpm until the cell density reached $OD_{600}$=0.5. After induction of foreign gene expression by 1 mM α-D-isopropylthiogalactoside (IPTG), the culture was shaken for 6 hours at 30° C. and 220 rpm. The cells were then precipitated by centrifugation (15 minutes at 3500×g, 4° C.) and resuspended in 35 ml breaking buffer (50 mM PB, 300 mM NaCl, 2 M urea, 0.5% Triton X-100, pH 8.0). After sonication, the sample was shaken at room temperature for 30 minutes to completely lyse cell debris. Inclusion body pellets were then collected by centrifugation (15 minutes, 10,000×g, 4° C.) and 20 ml denaturing buffer (50 mM PB, 300 mM NaCl, 8 M urea, 10 mM imidazole, pH 8.0) was added and shaken for one hour at room temperature. The pellets were removed by centrifugation (15 min, 10,000×g, 4° C.), the lysate was collected and the protein was purified with 5 ml HisTrap HP purification column (commercially available from GE Healthcare). The purity of the purified antibody protein was analyzed by SDS polyacrylamide gel electrophoresis and the protein concentration was determined by the BCA method.

Example 5. Binding Activity Assay of Antibody

Binding activity of an antibody to antigen EGFRvIII was determined by concentration gradient ELISA assay. For this purpose, the antigen EGFRvIII was diluted with 0.1 M

```
DIQMTQSPSSLSASVGDRVTITCHASQDINVNIGWLQQKPGKAFKGLIYHGKNLEDGVPS

RFSGSGSGTDFTLTISSLQPEDFATYYCNQYENFPLTFGQGTKVEIKRGGGGSGGGGSGG

GGSDVQLVESGGGLVQPGGSLRLSCAVSGYSITSDYAWNWIRQAPGKGLEWLGYISYRGR

TRYNPSLKSRISITRDNSKNTFFLQLNSLRAEDTAVYYCARLGRFRYWGQGTLVTVSS
```

Amino acid sequences of S23 light chain CDR1 (HASQDINVNIG), CDR2 (HGKNLED), CDR3 (NQYENFPLT) and heavy chain CDR1 (GYSITSDYAWN), CDR2 (YISYRGRTRYNPSLKS), CDR3 (LGRGFRY) are SEQ ID NO: 41, 42, 57, 44, 52, 50, respectively.

NaHCO$_3$ (pH 9.6) coating solution and each well was coated with 200 ng at 50 μl/well overnight at 4° C. and blocked with PBST containing 2% (w/v) BSA for 2 hours at room temperature. The plate was then rinsed for three times with PBST. Subsequently, 100 μl of each antibody protein solution in PBST containing a series of concentrations (initial concentration of 50 ng/well, 18 nM diluted until to 1:81) was added to each well plate and each sample was assayed using parallel three-well analysis. After incubation for 2 hours at 37° C., plate was rinsed for three times with PBST followed by adding 100 μl/well of a 1:2000 dilution of mouse anti-His-tag antibody (available from Santa cruz) for 1 hour at 37° C. To test the bound antibody, HRP-labeled goat anti-mouse antibody (purchased from Santa Cruz) was diluted in PBST at a 1:15,000 dilution and 100 μl per well was added and incubated at 37° C. for 1 hour. For detection, wells were rinsed for three times with PBST followed by rinsing for three times with PBS and finally TMB was added for development for 15 mins. The chromogenic reaction was stopped with 50 μl of 2 M $H_2SO_4$ per well and extinction value was measured at 450 nm using enzyme-linked immunoassay (Bio-Rad). The absorbance values obtained were evaluated using Sigma Plot software and the binding strength of an antibody was calculated. For this purpose, the extinction value measured in each case was plotted against the corresponding antibody concentration and the resulting curve was fitted using the following non-linear regression.

$$y = \frac{a*x}{(b+x)}$$

Wherein the binding/dissociation equilibrium identified between the immobilized antigen and the antibody protein is:

x=concentration of antibody protein;
y=concentration of antigen/antibody complex (indirectly measured by absorbance after color reaction);
a=total concentration of immobilized antigen;
b=dissociation constant ($K_D$).

Figure 2:
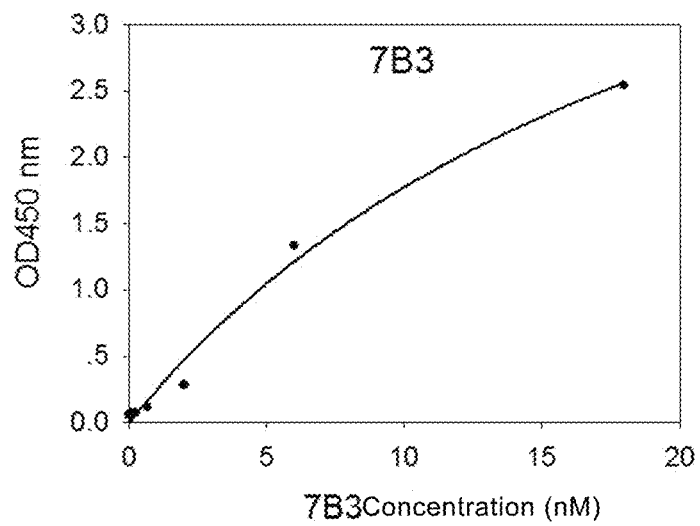
FIG. 2. Binding curve of antibody 7B3 vs antigen EGFRvIII.
Figure 3:
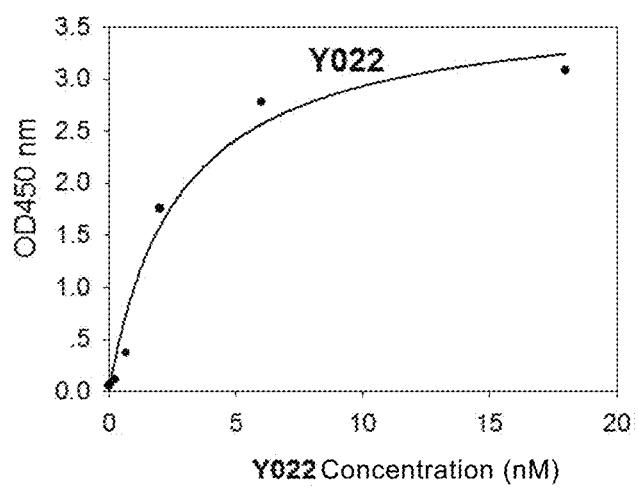
FIG. 3. Binding curve of antibody Y022 vs antigen EGFRvIII.

The binding curve obtained for antibody 7B3 in concentration-gradient ELISA assay is exemplarily shown in FIG. 2 with $K_D$ of about 22.4 nM; the binding curve of antibody Y022 to EGFRvIII is shown in FIG. 3 with apparent $K_D$ of about 2.7 nM.

Example 6. Activity Analysis on Binding of Y022 to Cell Surface EGFR

1. Expression and Purification of scFv-Y022-Fc, scFv-806-Fc and scFv-C225-Fc Fusion Antibody According to a standard scheme, scFv-Y022 fragment was amplified from the resulting clones using the primer pair V5-Y022-F (SEQ ID NO: 14, ACAGTGCTAGCAGATAT-TCAGATGACCCAG) and V5-Y022-R (SEQ ID NO: 15, AAGAATGCGGCCGCGCTGCTCACGGTCACCAG); ScFv-806 was amplified using the primer pair V5-806-F (SEQ ID NO: 16, ACAGTGCTAGCAGACATCCT-GATGACCCAAT) and V5-806-R (SEQ ID NO: 17, AAGAATGCGGCCGCTGCAGAGACAGTGACCAG) and pH-806/CD3 (see 201210094008.X) as the template; scFv-C225 fragment was cloned using the primer pairs V5-C225-F (SEQ ID NO: 18, ACAGTGCTAGCAGA-CATCTTGCTGACTCAG) and V5-C225-R (SEQ ID NO: 19, AAGAATGCGGCCGCTGCAGAGACAGTGACCAG) and C225 (VL-linker-VH) DNA fragment (sequence thereof was determined according to SEQ ID NO: 10 and SEQ ID NO: 12 in US20090099339A1 and obtained through whole-genome synthesis by Shanghai raygene biotechnology Co., LTD) as the template; and the amplified product was digested by NheI/NotI (purchased from NEB), linked with NheI/NotI-digested vector plasmid pCMV-V5-Fc (in the vector, the Fc fragment of human IgG1 was fused downstream to the multiple cloning site, abbreviated as V5-Fc, purchased from Shanghai raygene biotechnology Co., LTD) with T4 DNA ligase (purchased from NEB) and transformed into host strain TOP10. Clones were selected and the positive clones were identified by PCR and confirmed by sequencing, so as to obtain V5-scFv-Y022-Fc, V5-scFv-806-Fc and V5-scFv-C225-Fc eukaryotic expression plasmids, respectively.

The above expression plasmids were respectively transfected into well-growing HEK-293F cells, cultured at 37° C., 5% $CO_2$, 125 rpm shaker for 7 days, and centrifuged at 4000 rpm for 10 min. The precipitate was removed, the supernatant was collected and filtered with 0.45 μm membrane. The sample was affinity-purified with protein A (from GE) affinity column to finally obtain the purified antibody-Fc fusion proteins scFv-Y022-Fc, scFv-806-Fc and scFv-C225-Fc. Results are shown in FIG. 4.

2. Detection of Binding Ability of Single-Chain scFv-Y022-Fc, scFv-806-Fc and scFv-C225-Fc to Cell-Surface EGFR by FACS The binding capacities of each of single-chain antibodies scFv-Y022-Fc, scFv-806-Fc and scFv-C225-Fc to the following cell lines were analyzed by fluorescence activated cell sorter (FACS) (BD, FACS Calibur).

Specific methods are as follows:

1) tumor cells in logarithmic growth phase as listed in Table 2 were inoculated into a 6 cm dish with a inoculation cell density of about 90%, and incubated at 37° C. incubator overnight.

2) Cells were digested with 10 mM EDTA and cells were collected by centrifugation at 200 g for 5 min. Cells were resuspended in 1% phosphate buffered saline (NBS PBS) containing calf serum at a concentration of $1 \times 10^6$ to $1 \times 10^7$/mL, and added in a flow tube in an amount of 100 μl/tube.

3) Cells were centrifuged at 200g×5 min, and the supernatant was discarded.

4) Antibodies to be tested, scFv-Y022-Fc, scFv-806-Fc and scFv-C225-Fc, were added respectively. And PBS was used as a negative control. The final concentration of antibody was 20 μg/ml, 100 μl was added to each tube and placed in an ice bath for 45 minutes.

5) 2 ml of 1% NBS PBS was added to each tube and centrifuged at 200 g×5 min for two times.

6) Supernatant was discarded and FITC fluorescent-labeled goat anti-human antibody (from Shanghai Kangcheng Bio-engineering Company) at a dilution of 1:50 was added, and 100ul was added to each tube and placed in an ice bath for 45 minutes.

7) 2 ml of 1% NBS PBS was added to each tube and centrifuged at 200 g×5 min for two times.

8) Supernatant was discarded, resuspended in 300ul of 1% NBS PBS and detected by flow cytometry.

9) Data was analyzed by using flow cytometry data analysis software WinMDI 2.9.

TABLE 2

| Name of tumor cell | Source | Properties of cell | Expression of EGFR |
|---|---|---|---|
| U87 | ATCC | Glioma cell line | Low-expressed EGFR |
| U87-EGFR | Shanghai Cancer Institute | EGFR-transfected U87 cell line | over-expressed EGFR |

TABLE 2-continued

| Name of tumor cell | Source | Properties of cell | Expression of EGFR |
|---|---|---|---|
| U87-EGFRvIII | Shanghai Cancer Institute | EGFRvIII-transfected U87 cell line | over-expressed EGFRvIII |
| A431 | ATCC | Vaginal epithelial cancer | over-expressed EGFR |
| CAL 27 | ATCC | Tongue cancer cell line | over-expressed EGFR |
| MDA-MB-468 | ATCC | Breast cancer cell line | over-expressed EGFR |
| RWPE-1 | ATCC | Prostate normal epithelial cells | normally-expressed EGFR |
| K2 | Shanghai Cancer Institute | Human primary keratinocytes | normallyr-expressed EGFR |

Results are shown in FIG. 5, single chain antibody Y022 of the present invention can, with different degrees, bind to U87-EGFR exogenously overexpressing EGFR (Construction method can be found in Wang H., et al., Identification of an Exon 4-Deletion Variant of Epidermal Growth Factor Receptor with Increased Metastasis-Promoting Capacity. Neoplasia, 2011, 13, 461-471) and U87-EGFRvIII overexpressing EGFRvIII (construction method can be found in WO/2011/035465), A431, CAL27, MDA-MB-468 endogenously overexpressing EGFR, and especially strongly bind to U87-EGFRvIII and A431 cells, but its binding ability was not as high as that of single-chain antibody 806. Binding ability of the single-chain antibody C225 to these cells is very strong. These single-chain antibodies have little binding to U87 cells.

In addition, both Y022 and 806 single-chain antibodies almost did not bind to glioma cell line U87 cells. Especially, single chain antibody Y022 also does not bind to Normal prostate epithelial cells RWPE-1 and human primary keratinocyte K2, whereas single-chain antibody 806 binds to both of these normal cells with different degrees.

These results indicate that the single chain antibody Y022 specifically binds to tumor cells overexpressing EGFR as well as EGFRvIII, while little binding to normal EGFR-expressing cells.

Example 7. Construction of Expression Vector Containing Nucleotide Sequence Encoding Y022/CD3 Single Chain Bifunctional Antibodies PCR amplification was performed using the pCantab 5E-Y022 plasmid obtained in Example 3 as a template and a primer pair, the forward primer pH7B3f2 fw (SEQ ID NO: 20, GATATTCAGATGACCCAGAGCCCGAGCAG) and the reverse primer pH7B3f2_re (SEQ ID NO: 21, AATAG-GATCCACCACCTCCGCTGCTCACGGTCAC) to obtain DNA fragment of Y022 scFv. Another DNA fragment containing the pH vector signal peptide sequence was obtained by PCR using pH-7B3/CD3 plasmid (see 201210094008.X Example 3 and FIG. 2) as a template and the forward primer pH7B3f1_fw (SEQ ID NO: 22, CCAT-TGACGCAAATGGGCGGTAGG) and reverse primer pH7B3f1_re (SEQ ID NO: 23, CTGCTCGGGCTCTGGGT-CATCTGAATATC). The two fragments were mixed in equimolar ratio for fragment splicing and PCR. The splicing conditions were: denaturation: 94° C. for 4 min; denaturation: 94° C. for 40 s; annealing: 60° C. for 40 s; extension: 68° C. for 140 s for 5 cycles, and then the total extension of 68° C., 10 min. And then DNA polymerase and forward primer pH7B3f1_fw and reverse primer pH7B3f2 re were supplemented, 30 cycles of amplification were performed, and amplification conditions were: 94° C., 4 min; denaturation: 94° C., 40s; annealing: 60° C., 40s; 68° C. for 140 s for 30 cycles and then total extension 68° C. for 10 min.

The amplified sequence was digested with the restriction endonuclease NheI/BamHI and double-digested according to the reaction conditions recommended by the enzyme supplier (New England Biolabs, NEB). The expression vector pH (see 201210094008.X Example 3 and FIG. 2) was also similarly digested with the restriction enzyme NheI/BamHI. The double-digested Y022 scFv fragment and pH vector fragment were then ligated with T4 DNA ligase following the reaction conditions recommended by the enzyme supplier (NEB). The nucleotide sequence encoding for Y022 single chain antibody polypeptide thus obtained was cloned into a vector, and was transcribed together with the nucleotide sequence already contained in the vector encoding CD3 single-chain antibody polypeptide into an mRNA, which finally translated into Y022/CD3 single-chain bifunctional antibody polypeptide. The new plasmid was named as pH-Y022/CD3, and the detailed structure was shown in FIG. 6.

Example 8. Expression and Purification of Single Chain Bifunctional Antibody Y022/CD3, pH-806/CD3 and pH-C225/CD3

The expression vectors pH-Y022/CD3, pH-806/CD3 and pH-C225/CD3 (see 201210094008.X) were transfected into Chinese hamster ovary (CHO) cells according to the procedure of FreeStyle MAX Reagent Transfection Reagent (from Invitrogen). And then the stable clones were screened according to OptiCHO™ protein expression kit (from Invitrogen). Stable clones of CHO cells transfected with each of the above expression vectors were cultured in shake flasks at 37° C. for 7 days at 130 rpm, and the used medium was CD OptiCHO (from Gibco). The culture supernatant was obtained by centrifugation and then stored at −20° C.

Protein purification was performed using a histidine affinity column (His Trap HP column, available from GE Healthcare) according to the manufacturer's method steps. Specifically, the column was equilibrated with buffer A (20 mM sodium phosphate pH 7.4, 0.4 M NaCl) and then the cell culture supernatant (500 mL of the supernatant) was added to the column (1 mL) with a flow rate of 3 ml/min after dialysis against PBS. The column was then washed with 5 volumes of buffer A and 10 volumes of buffer A containing 50 mM imidazole to remove the impurity protein. The bound protein of interest was eluted with the same buffer A supplemented with 250 mM imidazole. All purification steps were performed at 4° C.

Purified single-chain bifunctional antibodies were detected by reducing SDS-PAGE. As shown in FIG. 7, the molecular weights of these antibody molecules were all around 60 kD, which corresponded to the molecular weight of the single-chain bifunctional antibody calculated from the amino acid sequences.

Example 9. Analysis of Antigen Binding Specificity of Single Chain Bifunctional Antibody Such as Y022/CD3

The binding capacities of single chain bifunctional antibody Y022/CD3 to EGFR were analyzed by fluorescence activated cell sorter (FACS) (BD, FACS Calibur).

Specific methods are as follows:

1. Tumor cells in logarithmic growth phase as listed in Table 2 were inoculated into a 6 cm dish with inoculation cell density of about 90%, and incubated at 37° C. incubator overnight.

2. Cells were digested with 10 mM EDTA and cells were collected by centrifugation at 200 g for 5 min. Cells were resuspended in 1% phosphate buffered saline (NBS PBS) containing calf serum at a concentration of $1\times10^6$ to $1\times10^7$/mL, and added in a flow tube in an amount of 100 μl/tube.

3. Cells were centrifuged at 200g×5 min, and the supernatant was discarded.

4. Antibody Y022/CD3 to be tested was added. And irrelevant antibody NGR/CD3 was used as a negative control. The final concentration of antibody was 5 μg/ml, 100 μl was added to each tube and placed in an ice bath for 45 minutes.

5. 2 ml of 1% NBS PBS was added to each tube and centrifuged at 200 g×5 min for two times.

6. Supernatant was discarded and mouse anti-his tag antibody (from Shanghai Genomics Technology Co., Ltd.) at a dilution of 1:50 was added, and 100ul was added to each tube and placed in an ice bath for 45 minutes.

7. 2 ml of 1% NBS PBS was added to each tube and centrifuged at 200 g×5 min for two times.

8. Supernatant was discarded and FITC fluorescent-labeled goat anti-mouse antibody (from Shanghai Kangcheng Bio-engineering Company) at a dilution of 1:50 was added, and 100ul was added to each tube and placed in an ice bath for 45 minutes.

9. 2 ml of 1% NBS PBS was added to each tube and centrifuged at 200 g×5 min for two times.

10. Supernatant was discarded, resuspended in 300ul of 1% NBS PBS and detected by flow cytometry.

11. Data was analyzed by using flow cytom6etry data analysis software WinMDI 2.9.

Figure 8:
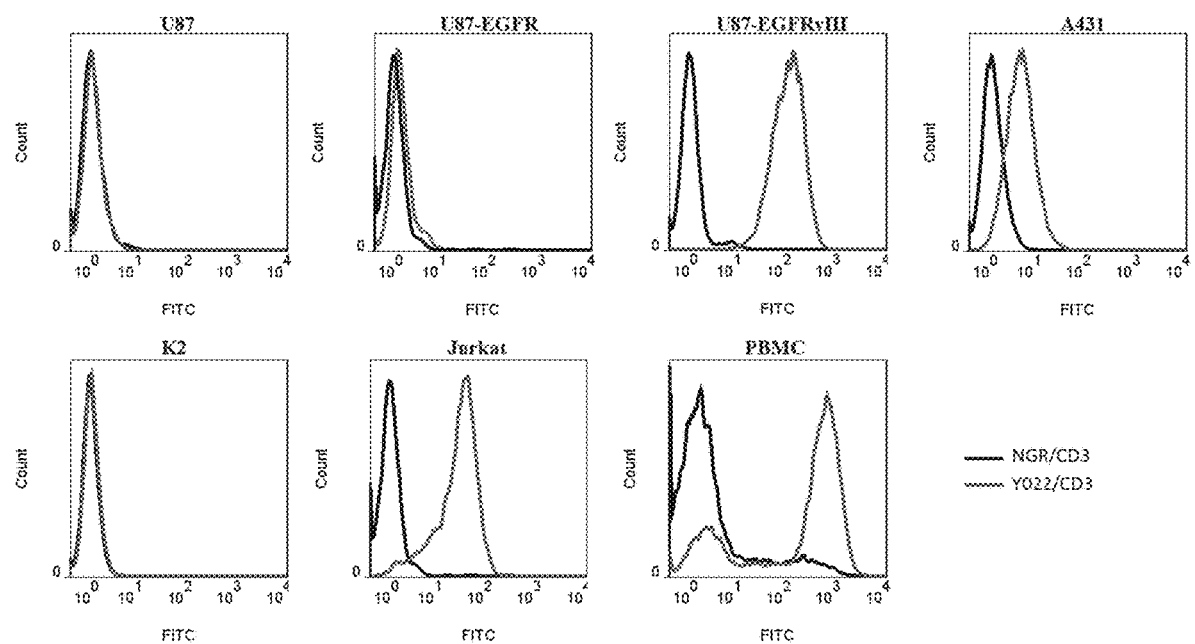
FIG. 8. Detection of Y022/CD3 single chain bifunctional antibody for its antigen binding specificity by FACS.

Results are shown in FIG. 8, the bifunctional antibody Y022/CD3 of the present invention can bind to U87-EGFR, U87-EGFRvIII and A431 cells, however, hardly bind to U87 and human keratinous epithelial cells. These results indicate that Y022/CD3 can specifically bind to tumor cells expressing mutant human EGFR and overexpressing EGFR, but not to tissues that normally express EGFR.

In addition, Y022/CD3 can also bind to human peripheral blood mononuclear cells (PBMCs) or Jurkat cells (human peripheral blood leukemia T cells, CD3 positive) as shown in the figure, suggesting that the bifunctional antibody of the present invention can specifically bind to CD3 antigen of T cell surface.

The expression plasmids were constructed according to the methods mentioned in Examples 7 and 8, respectively (Y022 in Examples 7 and 8 were replaced with other mutated forms of antibodies), and M14/CD3, M15/CD3, M25/CD3, M26/CD3, S7/CD3, S8/CD3, S17/CD3, S22/CD3, S23/CD3, S29/CD3 were expressed and purified. According to the method of this example, the binding abilities of these antibodies to U87-EGFRvIII overexpressing EGFRvIII and to CAL27 cells endogenously overexpressing EGFR were determined respectively. The above antibodies were able to bind both of these cells, and their mean fluorescence intensity (MFI) values are shown in Table 13.

TABLE 13

| Antibody | U87MG-EGFRvIII | CAL 27 |
|---|---|---|
| PBS | 1 | 3.11 |
| M14 | 36.52 | 28.39 |
| M15 | 37.86 | 29.43 |
| M25 | 36.52 | 24.14 |
| M26 | 41.42 | 24.58 |
| S7 | 42.17 | 27.88 |
| S8 | 38.54 | 29.96 |
| S17 | 31.62 | 25.03 |
| S22 | 31.34 | 24.58 |
| S23 | 32.2 | 29.69 |
| S29 | 34.6 | 25.71 |

Example 10. Biological Activity Analysis of Single-Chain Bifunctional Antibody, Such as Y022/CD3—Cytotoxicity to Various Tumor Cells Peripheral blood mononuclear cells (PBMCs) were isolated from healthy human-donated blood following standard procedures using Ficoll (from Biochrom) density gradient centrifugation. After centrifugation, the cells were washed with phosphate buffered saline (PBS) at a concentration of 0.1 M and then resuspended in RPMI 1640 complete medium (Gibco) and the cell concentration was adjusted to $5\times10^5$/mL. PBMCs served as effector cells in cytotoxicity experiments. Different tumor cells act as target cells. The target cell concentration was adjusted to $5\times10^4$/mL with RPMI 1640 complete medium. The same volume of target cells and effector cells were mixed such that the effector cell: target cell (E:T) ratio was 10:1.

The mixed cell suspension was added to a 96-well plate in a volume of 75 μL/well. Then 25 μL of the following reagent serially diluted ten times from 1000 ng/mL to 0.1 ng/mL was added to each well:

(1) Y022/CD3 Single chain bifunctional antibody (BiTe);

(2) RPMI 1640 complete medium (background);

(3) NGR/CD3 Single chain bifunctional antibody (negative control, NGR was a neovascular targeting peptide that has no cross-binding site with EGFR, and prepared according to a conventional method)

After incubation for 40 hours in a 37° C., 5% $CO_2$ incubator, the cytotoxicity of the antibody was tested using CytoTox 96® Non-Radioactive Cytotoxicity Assay kit (from Promega) according to the manufacturer's instructions.

The CytoTox 96® Non-Radioactive Cytotoxicity Assay is a colorimetric based assay that can replace 51Cr release assay. CytoTox 96® Assay measures lactate dehydrogenase (LDH) quantitatively. LDH is a stable cytosolic enzyme that is released upon lysis of cells and is released in the same way as radioactive 51Cr is released. The supernatant with released LDH medium can be detected by a 30-minute coupled enzyme reaction in which LDH converts a tetrazolium salt (INT) to a red formazan. The amount of red product produced is proportional to the number of lysed cells.

Five EGFR-associated tumor cells as listed in Table 3 below were used to analyze T cell tumors killing ability mediated by the bifunctional antibody Y022/CD3 of the present invention and the NGR/CD3 single-chain bifunctional antibody that is not associated with EGFR as a control, respectively.

Tumor cell killing rate (i.e., cytotoxicity %) was calculated based on the following formula provided in the manual of CytoTox 96® non-radioactive cytotoxicity assay G1780:

cytotoxicity %=[(experiment−effector cell spontaneously−target cell spontaneously)/(target cell maxium−target cell spontaneously)]×100 wherein:

"Experiment" refers to LDH release produced in the experimental wells, in which the antibody/effector/target cells were added, "effector cell spontaneously" refers to LDH release produced by effector cells spontaneously, "target cell spontaneously" refers to LDH release produced by cells that are not treated by other factors, "target cell maxium" refers to LDH release resulting from complete lysis of target cells after treatment with 0.8% Triton X-100, "target cell maxium−target cell spontaneously" refers to LDH release resulting from complete lysis of cells after external treatment.

TABLE 3

| Tumor cell line | 1000 ng/ml Cytotoxicity % of Y022/CD3 | 1000 ng/ml Cytotoxicity % of NGR/CD3 |
|---|---|---|
| U87 | 2.0 | 3.4 |
| U87-EGFR | 32.1 | 3.7 |
| U87-EGFRvIII | 66.2 | 6.3 |
| A431 | 48.7 | 5.2 |
| K2 | 5.1 | 4.5 |

The results of Table 3 above show that all of the tumor cells expressing mutant EGFR and/or overexpressing EGFR, such as U87-EGFRvIII, U87-EGFR and A431, will be specifically killed by T-cells directed by the bifunctional antibody Y022/CD3.

Specifically, in the above tumor cell group treated with Y022/CD3, the minimum specific cytotoxicity was 32.1% and the maximum was 66.2%. While the cytotoxicity of Y022/CD3 to cells expressing low levels of EGFR, U87, and human primary keratinocytes was very low at 3.4% and 4.5%, respectively, which were significantly lower than those to the above-mentioned mutant cells expressing EGFR and/or overexpressing EGFR.

More specifically, cytotoxicity % of Y022/CD3 and control antibody NGR/CD3 at various concentrations to each tumor is shown in Tables 4-8 below.

TABLE 4

| | U87 | |
|---|---|---|
| ng/ml | NGR/CD3 | Y022/CD3 |
| 1000 | 3.4 ± 1.2 | 2.0 ± 1.3 |
| 100 | 4.8 ± 1.1 | 1.6 ± 3.2 |
| 10 | 4.3 ± 1.5 | 2.5 ± 2.3 |
| 1 | 5.2 ± 2.1 | 0.5 ± 1.2 |
| 0.1 | 5.4 ± 2.2 | 0.2 ± 1.7 |

TABLE 5

| | U87-EGFR | |
|---|---|---|
| ng/ml | NGR/CD3 | Y022/CD3 |
| 1000 | 3.7 ± 2.6 | 32.1 ± 3.1 |
| 100 | 4.9 ± 1.7 | 21.7 ± 4.4 |
| 10 | 4.3 ± 2.7 | 12.6 ± 3.2 |
| 1 | 3.3 ± 1.9 | 6.3 ± 2.6 |
| 0.1 | 0.7 ± 1.2 | 5.1 ± 2.0 |

TABLE 6

| | U87-EGFRvIII | |
|---|---|---|
| ng/ml | NGR/CD3 | Y022/CD3 |
| 1000 | 6.3 ± 1.3 | 66.2 ± 5.8 |
| 100 | 7.4 ± 2.4 | 52.5 ± 4.5 |
| 10 | 6.5 ± 0.8 | 33.6 ± 3.2 |
| 1 | 4.7 ± 2.1 | 25.3 ± 2.9 |
| 0.1 | 2.6 ± 1.4 | 6.7 ± 2.3 |

TABLE 7

| | A431 | |
|---|---|---|
| ng/ml | NGR/CD3 | Y022/CD3 |
| 1000 | 5.2 ± 2.9 | 48.7 ± 4.3 |
| 100 | 5.6 ± 2.7 | 35.3 ± 5.1 |
| 10 | 3.7 ± 2.4 | 22.7 ± 3.3 |
| 1 | 1.3 ± 0.6 | 10.8 ± 4.4 |
| 0.1 | 1.5 ± 1.1 | 4.3 ± 2.1 |

TABLE 8

| | K2 | |
|---|---|---|
| ng/ml | NGR/CD3 | Y022/CD3 |
| 1000 | 4.5 ± 2.2 | 5.1 ± 1.1 |
| 100 | 4.1 ± 2.8 | 3.2 ± 1.2 |
| 10 | 3.5 ± 2.4 | 1.7 ± 1.0 |
| 1 | 2.1 ± 1.8 | 2.7 ± 1.2 |
| 0.1 | 4.3 ± 2.9 | 2.1 ± 1.3 |

In addition, in vitro toxicity analysis was performed by the same method on the following expressed and purified BiTe: M14/CD3, M15/CD3, M25/CD3, M26/CD3, S7/CD3, S8/CD3, S17/CD3, S22/S29/CD3, and the results are shown in FIG. 9.

Figure 9:
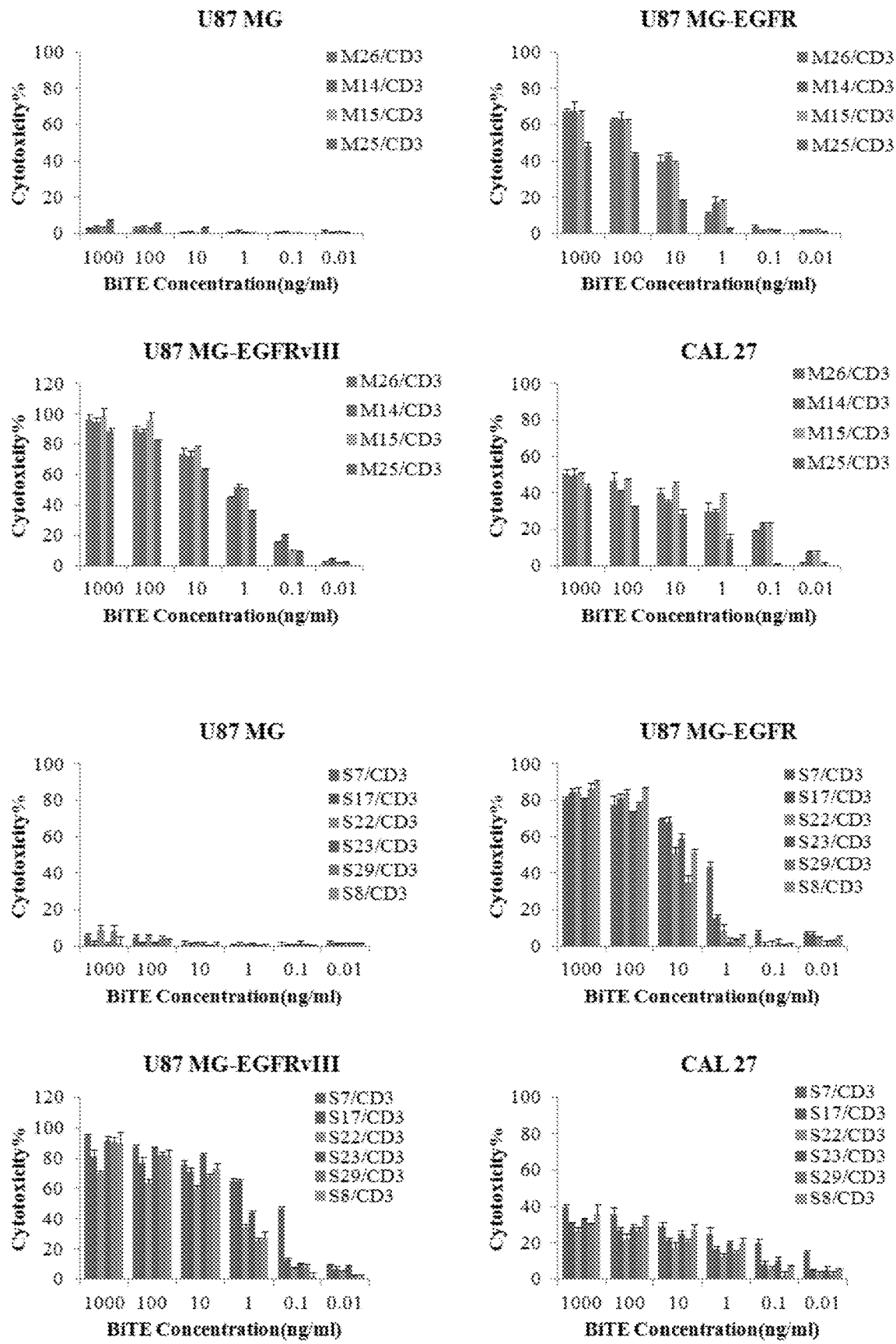
FIG. 9. Cytotoxicity plots of single-chain bifunctional antibodies.

As can be seen in FIG. 9, tumor cells expressing mutated EGFR and/or overexpressing EGFR, such as U87-EGFRvIII, U87-EGFR, and CAL27, can be killed by T cells directed by the bifunctional specific antibodies M14/CD3, M15/CD3, M25/M26/CD3, S7/CD3, S8/CD3, S17/CD3, S22/CD3, S23/CD3, S29/CD3 to different degrees. While for U87, a cell that expresses low levels of EGFR, there is little killing effect.

Figure 10:
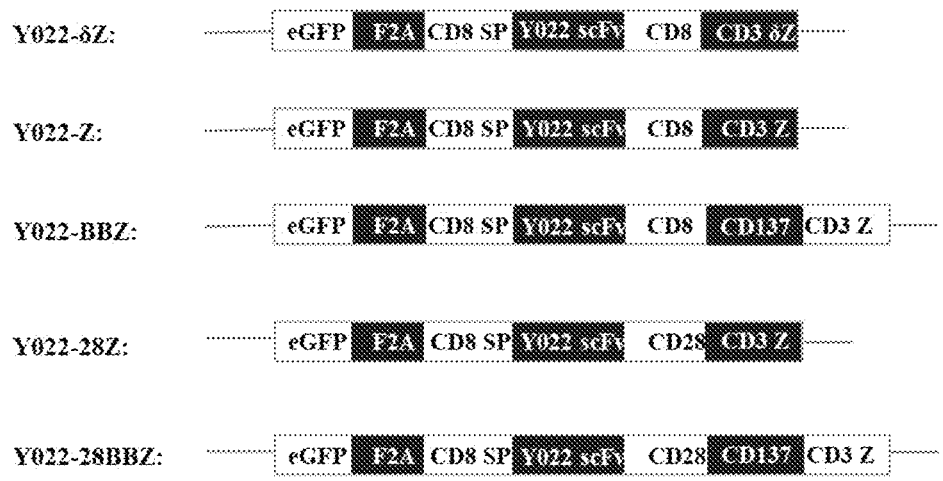
FIG. 10. Schematic illustration of the ligation order of various parts of the chimeric antigen receptor.

Example 11. Construction of Lentiviral Plasmid Expressing the Chimeric Antigen Receptor Protein Encoded by the Nucleic Acid of the Present Invention and Virus Packaging Construction of the chimeric antigen receptor, and the connection order of chimeric antigen receptor exemplified in the present invention, is shown in Table 9 and FIG. 10.

TABLE 9

| chimeric antigen receptor | Extracellular binding region - transmembrane region - intracellular signal region 1 - intracellular signal region 2 and the like | Description |
|---|---|---|
| Y022-δZ | scFv(EGFR)-CD8-CD3δzeta | Negative control |
| Y022-Z | scFv(EGFR)-CD8-CD3 zeta | 1st generation |
| Y022-BBZ | scFv(EGFR)-CD8-CD137-CD3 zeta | 2nd generation |
| Y022-28Z | scFv(EGFR)-CD28a-CD28b-CD3 zeta | 2nd generation |
| Y022-28BBZ | scFv(EGFR)-CD28a-CD28b-CD137-CD3 zeta | 3rd generation |

Note:
CD28a represents the transmembrane region of CD28 molecule and CD28b represents the intracellular signaling region of CD28 molecule.

1. Amplification of Nucleic Acid Fragments (1) Amplification of scFv Sequences

Y022 scFv was obtained by PCR using pCantab 5E-Y022 plasmid as a template with a forward primer (SEQ ID NO: 24, comprising part of the sequence of CD8 signal peptide) and a reverse primer (SEQ ID NO: 25, comprising part of the sequence of CD8 hinge).

SEQ ID NO: 24
(TGCTCCACGCCGCCAGGCCGGATATTCAGATGACCCAG)

SEQ ID NO: 25
(CGCGGCGCTGGCGTCGTGGTGCTGCTCACGGTCAC)

(2) Nucleic Acid Sequences of Other Parts of the Chimeric Antigen Receptor

The nucleic acid sequences of other parts of the anti-EGFRvIII chimeric antigen receptor protein except for Y022 scFv were respectively obtained by PCR using the sequences SEQ ID NO: 26, 27, 28, 29 and 30 disclosed in Patent Application No. 201310164725.X as templates. Specifically, the eGFP-F2A-CD8sp sequence was obtained by PCR amplification using SEQ ID NO: 27 plasmid contained in Patent Application No. 201310164725.X as a template and primer pairs (SEQ ID NOs: 26 and 27). CD8-CD3δ zeta (δZ) was obtained by PCR amplification using SEQ ID NO: 26 plasmid in the patent application CN201310164725.X as a template and primer pairs (SEQ ID NOs: 28 and 29). The CD8-CD3 zeta (Z), CD8-CD137-CD3 zeta (BBZ), CD28a-CD28b-CD3 zeta (28Z) and CD28a-CD28b-CD137-CD3 zeta (28BBZ) were obtained by PCR amplification respectively using SEQ ID NO: 27, SEQ ID NO: 28, SEQ ID NO: 29 and SEQ ID NO: 30 in the patent application CN201310164725.X as templates and primer pairs (SEQ ID NO: 28, 30).

SEQ ID NO: 26
(TGCAGTAGTCGCCGTGAAC)

SEQ ID NO: 27
(CGGCCTGGCGGCGTGGAGCA)

SEQ ID NO: 28
(ACCACGACGCCAGCGCCGCGACCAC)

SEQ ID NO: 29
(GAGGTCGACCTACGCGGGGGCGTCTGCGCTCCTGCTGAACTTCACTCT)

SEQ ID NO: 30
(GAGGTCGACCTAGCGAGGGGGCAGGGCCTGCATGTGAAG)

2. Splicing of Nucleic Acid Fragments eGFP-F2A-CD8sp nucleic acid fragment obtained as described above and equimolar Y022 scFv nucleic acid fragment and equimolar CD8-CD3δ zeta (δZ) or CD8-CD3 zeta (Z) or CD8-CD137-CD3 zeta (BBZ) or CD28a-CD28b-CD3 zeta (28Z) or CD28a-CD28b-CD137-CD3 zeta (28BBZ) nucleic acid fragments were subjected to three-segment splicing and PCR as shown in FIG. 9 under the following conditions: Pre-denaturation: 94° C. for 4 min; denaturation: 94° C. for 40 s; annealing: 60° C. for 40 s; extension: 68° C. for 140 s for 5 cycles and then total extension 68° C. for 10 min. DNA polymerase and forward primer (SEQ ID NO: 24) and reverse primer (reverse primer corresponding to CD8-CD3δ zeta was SEQ ID NO: 29, and other is SEQ ID NO: 30) were supplemented, and then PCR was performed for 30 cycles with the amplification conditions: Pre-denaturation: 94° C. for 4 min; denaturation: 94° C. for 40 s; annealing: 60° C. for 40 s; extension: 68° C. for 140 s for 30 cycles and then total extension 68° C. for 10 min. The amplified fragments were referred to as (Table 2):

eGFP-F2A-Y022 scFv-δZ (SEQ ID NO: 31),
eGFP-F2A-Y022 scFv-Z (SEQ ID NO: 32),
eGFP-F2A-Y022 scFv-BBZ (SEQ ID NO: 33),
eGFP-F2A-Y022 scFv-28Z (SEQ ID NO: 34),
eGFP-F2A-Y022 scFv-28BBZ (SEQ ID NO: 35).

3. Construction of Lentiviral Plasmid Vector

By way of example, the vector system used for the lentiviral plasmid vectors constructed below belongs to self-inactivating lentiviral vector system of the third generation, which has three plasmids, namely, packaging plasmid psPAX2 encoding protein Gag/Pol, encoding Rev protein (from addgene); envelope plasmid PMD2.G encoding VSV-G protein (from addgene); and the recombinant expression vector encoding the gene of interest CAR based on empty vector pWPT-eGFP (from addgene).

In the empty vector pWPT-eGFP, the expression of enhanced green fluorescent protein (eGFP) is regulated by elongation factor-1α (EF-1α) promoter. After inserting the constructs constructed as described in this example into an empty vector, a recombinant expression vector encoding CAR of the target gene was formed, wherein co-expression of eGFP and target gene CAR is achieved ribosomal skipping sequence from food and mouth disease virus (FMDV, F2A). F2A is a core sequence of 2A (or "self-cleaving polypeptide 2A") from foot-and-mouth disease virus possessing the "self-shearing" function of 2A that enables upstream and downstream gene co-expression. 2A provides an effective and viable strategy for constructing polycistronic vectors for gene therapy due to its high shearing efficiency, high upstream and downstream gene expression balance and short sequence itself. Especially in immunotherapy based on chimeric antigen receptor gene modified T lymphocytes, this sequence is frequently used to achieve the co-expression of the target gene with GFP or eGFP. The expression of CAR can be indirectly detected by detecting GFP or eGFP.

In this example, a lentiviral expression vector co-expressing eGFP and specific CAR linked by F2A was constructed, collectively referred to as pWPT-eGFP-F2A-CAR. The target gene eGFP-F2A-CAR (see 2 in Example 7, the component after F2A is abbreviated as CAR) obtained in the above step 2 was double-digested by MluI and SalI restriction enzymes and ligated into the same double digested pWPT vector to construct a lentiviral vector expressing each chimeric antigen receptor. The constructed vector was identified by MluI and SalI digestion and sequenced correctly, which was ready for lentivirus packaging. As mentioned above, eGFP-F2A-CAR was transcribed into one mRNA but eventually translated into two peptide chains of eGFP and anti-EGFRvIII chimeric antigen receptors, where the anti-EGFRvIII chimeric antigen receptor will be localized under the guidance of CD8α signal peptide on the cell membrane.

The vectors containing the desired CARs are as follows (the components following F2A may be abbreviated as CAR):
pWPT-eGFP-F2A-Y022 scFv-δZ;
pWPT-eGFP-F2A-Y022 scFv-Z;
pWPT-eGFP-F2A-Y022 scFv-BBZ;
pWPT-eGFP-F2A-Y022 scFv-28Z;
pWPT-eGFP-F2A-Y022 scFv-28BBZ.

5 eGFP-F2A-CAR polypeptide sequences were respectively obtained through the above construction, which are named as:
eGFP-F2A-Y022 scFv-δZ (SEQ ID NO: 36);
eGFP-F2A-Y022 scFv-Z (SEQ ID NO: 37);
eGFP-F2A-Y022 scFv-BBZ (SEQ ID NO: 38);
eGFP-F2A-Y022 scFv-28Z (SEQ ID NO: 39);
eGFP-F2A-Y022 scFv-28BBZ (SEQ ID NO: 40).

4. Plasmid-Transfected 293T Packaging Lentivirus

HEK-293T cells (ATCC: CRL-11268) cultured at passage 6 to passage 10 were seeded at a density of $6\times10^6$ in 10 cm dishes and cultured overnight at 37° C. in 5% $CO_2$ for transfection. The medium was DMEM (available from PAA) containing 10% fetal bovine serum (purchased from PAA).

Transfection steps are as follows:

4.1 Preparation of liquid A: dissolving 10 μg of mock control or 10 μg of each of the desired gene plasmids pWPT-eGFP-F2A-CAR with 7.5 μg of packaging plasmid PAX2: and 3 μg of envelope plasmid pMD2.G into 800 μL of serum-free DMEM medium and mixing well.

4.2 Preparation of liquid B: dissolving 60 μg PEI (polyethylenimine, purchased from Polysciences) in 800 μL serum-free DMEM medium, mixing gently and incubating at room temperature for 5 min.

4.3 Formation of transfection complex: adding liquid A into liquid B and gently mixing, vortexing or gently mixing immediately after addition, incubating at room temperature for 20 min.

4.4 Adding 1.6 ml of the transfection complex into HEK-293T cells dropwise, and after 4-5 h, changing to DMEM with 2% FBS for transfected 293T cells.

In the next day after transfection, the transfection efficiency (that is, the proportion of green fluorescent cells) was observed: ~80% of the positive transfection efficiency represents the successful transfection experiments. After 72 h of transfection, the virus was collected by filtration using a 0.45 μm filter (available from Millipore Corporation) and centrifuged at 28,000 rpm using a Beckman Optima L-100XP ultracentrifuge for 2 hours at 4° C. The supernatant was discarded and the resulting pellet was centrifuged at ⅟10 ~⅟50 stock solution of AIM-V (purchased from Invitrogen) and resuspend at 100 μL/tube in −80° C. for virus titration or infection of T lymphocytes.

5. Determination of Lentiviral Titers Packaged with Mock or eGFP-F2A-CAR

On the first day, 293T cells were inoculated at $1\times10^5$/mL in 96-well culture plates, 100 μL/well, and cultured at 37° C., 5% $CO_2$, and the culture medium was DMEM containing 10% fetal bovine serum. On the next day, 50 μL/well of culture supernatant was discarded, 50 μL/well of fresh medium was supplemented, and polybrene at final concentration of 6 μg/mL was contained. The culture was incubated for 30 min at 37° C. with 5% CO2. 10 μL/well of virus stock or 1 μL/well of virus concentrate was added (3-fold diluted, 6 gradients, two replicate wells) and incubated at 37° C. in 5% $CO_2$. 48h after infection, eGFP was detected by flow cytometry, cells with 5 to 20% of the positive rate are appropriate to calculate the titer (U/mL)=positive rate× dilution times×100×$10^4$. The titers of virus comprising the above-mentioned mock empty vector control and each eGFP-F2A-CAR packaged in the PEI transfection method were both about 0.5 to $1\times10^7$U/mL, and the detected virus titer after concentration was about 0.5~$1\times10^8$U/mL.

Example 12. T Cells Infected by Recombinant Lentivirus

Human peripheral blood mononuclear cells were obtained from healthy human peripheral blood by density gradient centrifugation (supplied by Shanghai Blood Center) and added in AIM-V lymphocyte medium (purchased from Invitrogen) at a density of about $2\times10^6$/mL and added. The magnetic beads coated with anti-CD3 and CD28 antibodies (Invitrogen) were added in a 1:1 ratio of cells to magnetic beads, and recombinant human IL-2 (purchased from Shanghai Huaxin Biotechnology Co., Ltd.) at a final concentration of 300U/mL was added for stimulation and culture for 48 h. And then T cells were infected with the above recombinant lentivirus (MOI≈15). Infected T cells were detected by flow cytometry on day 8 of culture for the expression of different chimeric antigen receptors. Since eGFP was co-expressed with CAR, the detected eGFP-positive cells were positive cells expressing chimeric antigen receptors. Using uninfected T lymphocytes as a negative control, the positive rates of virus-infected T cells expressing different chimeric antigen receptors are shown in Table 10. The positive rate results show that a certain positive rate of CAR T cells can be obtained by lentivirus infection.

TABLE 10

| T cells transfected by following CARs | eGFP positive rate of CAR T cells |
|---|---|
| Y022-δZ (Mock) | 66% |
| Y022-Z | 58% |
| Y022-BBZ | 53% |
| Y022-28Z | 54% |
| Y022-28BBZ | 52% |

T cells were infected with viruses that had different chimeric antigen receptors packaged, respectively, and then subcultured at a cell density of $5\times10^5$/ml quaque die alterna, counted, and supplemented with IL-2 (final concentration of 300 U/ml). On the 11th day of culture, about 100~1000 times of amplification was obtained, indicating that the T cells expressing different chimeric antigen receptors can be expanded in a certain amount in vitro, which ensures subsequent in vitro toxicity tests and in vivo experiments.

Example 13. In Vitro Antitumor Activity of CAR-Y022

In vitro toxicity experiments used the following materials:
The target cells were U87, U87-EGFR, U87-EGFRvIII, A431, CAL 27, MDA-MB-468, RWPE-1 cells and human primary keratinocyte K2 as shown in Table 5, respectively. Effector cells were T lymphocytes (CAR T cells) cultured for 12 days in vitro, which were detected chimeric antigen receptor positive by FACS.

Effective target ratios were 3:1, 1:1 and 1:3, respectively. The number of target cells was 10000/well, and each group had 5 replicate wells. Detection time was 18 h.

Each experimental group and each control group are listed as follows:

Each experimental group: each target cell+CAR T lymphocytes expressing different chimeric antigen receptors;

Control group 1: target cells with maxium LDH release;

Control group 2: target cells with spontaneous LDH release;

Control group 3: effector cells with spontaneous LDH release.

Detection method: CytoTox 96® Non-Radioactive Cytotoxicity Assay (Promega) is used, which is a colorimetric based assay that can replace 51Cr release assay. CytoTox 96® Assay measures lactate dehydrogenase (LDH) quantitatively. LDH is a stable cytosolic enzyme that is released upon lysis of cells and is released in the same way as radioactive 51Cr is released. The supernatant with released LDH medium can be detected by a 30-minute coupled enzyme reaction in which LDH converts a tetrazolium salt (INT) to a red formazan. The amount of red product produced is proportional to the number of lysed cells. Details can be found in instructions of CytoTox 96 non-radioactive cytotoxicity detection kit.

Cytotoxicity is calculated as:

Cytotoxicity %=[(experiment group−control group2−control group3)/(control group1−control group2)]×100

Specifically, as shown in Table 11 and Table 12, compared with 806-CAR T, Y022-28Z CAR T and Y022-28BBZ CAR T expressing chimeric antigen receptors of the present invention at different effector target ratios showed a significantly killing effects on cells highly expressing EGFR and EGFRvIII and a effector target ratio gradient dependency, that is, the higher the effector target ratio, the stronger the cytotoxic effects. Effector-target-ratio-dependency data further demonstrate the specific cytotoxic effects of CAR T cells expressing chimeric antigen receptors of the invention on cells that highly express EGFR and its variants.

It is noteworthy that Y022-CAR T has almost no killing effect on RWPE-1 cells that normally express EGFR and human primary keratinocytes K2. At the effector target ratio of 3:1, Cytotoxicity of the chimeric antigen receptor Y022-28BBZ CAR T-lymphocyte to RWPE-1 cells and human primary keratinocytes K2 was 12% and 2%, respectively. Cytotoxicity of Y022-28Z CAR T lymphocytes to RWPE-1 cells and human primary keratinocytes K2 was 8% and 3%. In contrast, 806-CAR T had different degrees of cytotoxicity on both of these cells. The cytotoxicity of 806-28BBZ CAR T lymphocytes to RWPE-1 cells and human primary keratinocytes K2 were 25% and 22%, respectively, and the cytotoxicity of 806-28Z CAR T lymphocytes to RWPE-1 cells and human primary keratinocytes K2 was 15% and 13%, respectively.

In addition, CAR T, as a negative control, transfected with a virus containing the mock plasmid (carrying scFv-Y022-δZ) showed very low cytotoxic effects on the above cell lines.

The above results indicate that the chimeric antigen receptor Y022-CAR T, which is constructed from a single chain antibody against EGFR and its variants, can selectively kill tumor cells that highly express EGFR and its variant (EGFRvIII), while hardly kill cells normally expressing EGFR. In addition, from the cytotoxicity data, CAR T of the third generation (Y022-28BBZ) was more cytotoxic to target cells than the second generation (Y022-28Z) CART.

TABLE 11

| | Y022-28BBZ Different effector target ratio | | | Y022-28Z Different effector target ratio | | | mock Different effector target ratio | | |
|---|---|---|---|---|---|---|---|---|---|
| Cytotoxicity % | 3:1 | 1:1 | 1:3 | 3:1 | 1:1 | 1:3 | 3:1 | 1:1 | 1:3 |
| U87 | 2 | 4 | 5 | 4 | 3 | 1 | −4 | −3 | 2 |
| U87-EGFR | 35 | 17 | 6 | 25 | 16 | 7 | −1 | 5 | 1 |
| U87-EGFRvIII | 73 | 42 | 19 | 65 | 31 | 9 | 3 | 0.3 | 1 |
| A431 | 67 | 37 | 12 | 45 | 24 | 5 | 9 | 7 | 4 |
| CAL27 | 70 | 49 | 15 | 50 | 23 | 8 | 7 | 5 | 5 |
| MDA-MB-468 | 57 | 45 | 14 | 41 | 23 | 1 | 6 | 8 | 7 |
| RWPE-1 | 12 | 7 | 3 | 8 | 6 | 4 | 3 | 2 | 0.2 |
| K2 | 11 | 2 | 0.3 | 3 | 0.6 | 2 | −3 | −1 | 2 |

TABLE 12

| | 806-28BBZ Different effector target ratio | | | 806-28Z Different effector target ratio | | | mock Different effector target ratio | | |
|---|---|---|---|---|---|---|---|---|---|
| Cytotoxicity % | 3:1 | 1:1 | 1:3 | 3:1 | 1:1 | 1:3 | 3:1 | 1:1 | 1:3 |
| U87 | 3 | 4 | 2 | 5 | 0.6 | 2 | 1 | 3 | −3 |
| U87-EGFR | 68 | 49 | 18 | 55 | 36 | 12 | 3 | 7 | 4 |
| U87-EGFRvIII | 83 | 51 | 23 | 75 | 42 | 15 | 6 | 5 | 2 |
| A431 | 75 | 48 | 16 | 56 | 35 | 12 | 7 | 7 | 5 |
| CAL27 | 81 | 57 | 25 | 65 | 33 | 18 | 3 | 6 | 2 |
| MDA-MB-468 | 62 | 49 | 32 | 51 | 32 | 16 | 6 | 9 | 7 |
| RWPE-1 | 29 | 17 | 10 | 15 | 10 | 7 | −2 | −3 | 2 |
| K2 | 27 | 15 | 2 | 13 | 9 | 4 | 0.2 | 1 | 3 |

All references mentioned in the present application are incorporated herein by reference, as if each reference was individually incorporated by reference. In addition, it should be understood that after reading the above teachings of the present invention, those skilled in the art can make various modifications or changes to the present invention, and such equivalent forms also fall within the scope of the appended claims of the present application.

The invention claimed is:

1. A monoclonal antibody specifically recognizing EGFRvIII expressed or EGFR overexpressed by tumor cells, wherein the antibody comprises:

antibody (a), wherein the light chain variable region thereof has CDR1 of SEQ ID NO: 41, CDR2 of SEQ ID NO: 42, and CDR3 of SEQ ID NO: 43, and the heavy chain variable region thereof has CDR1 of SEQ ID NO: 44, CDR2 of SEQ ID NO: 45, and CDR3 of SEQ ID NO: 46;

antibody (b), wherein the light chain variable region thereof has CDR1 of SEQ ID NO: 47, CDR2 of SEQ ID NO: 42, and CDR3 of SEQ ID NO: 48, and the heavy chain variable region thereof has CDR1 of SEQ ID NO: 44, CDR2 of SEQ ID NO: 49, and CDR3 of SEQ ID NO: 50;

antibody (c), wherein the light chain variable region thereof has CDR1 of SEQ ID NO: 41, CDR2 of SEQ ID NO: 42, and CDR3 of SEQ ID NO: 48, and the heavy chain variable region thereof has CDR1 of SEQ ID NO: 44, CDR2 of SEQ ID NO: 51, and CDR3 of SEQ ID NO: 50;

antibody (d), wherein the light chain variable region thereof has CDR1 of SEQ ID NO: 41, CDR2 of SEQ ID NO: 42, and CDR3 of SEQ ID NO: 43, and the heavy chain variable region thereof has CDR1 of SEQ ID NO: 44, CDR2 of SEQ ID NO: 52, and CDR3 of SEQ ID NO: 50;

antibody (e), wherein the light chain variable region thereof has CDR1 of SEQ ID NO: 41, CDR2 of SEQ ID NO: 42, and CDR3 of SEQ ID NO: 43, and the heavy chain variable region thereof has CDR1 of SEQ ID NO: 44, CDR2 of SEQ ID NO: 45, and CDR3 of SEQ ID NO: 50;

antibody (f), wherein light chain variable region thereof has CDR1 of SEQ ID NO: 41, CDR2 of SEQ ID NO: 53, and CDR3 of SEQ ID NO: 54, and the heavy chain variable region thereof has CDR1 of SEQ ID NO: 44, CDR2 of SEQ ID NO: 51, and CDR3 of SEQ ID NO: 50;

antibody (g), wherein the light chain variable region has CDR1 of SEQ ID NO: 41, CDR2 of SEQ ID NO: 42, and CDR3 of SEQ ID NO: 54, and the heavy chain variable region thereof has CDR1 of SEQ ID NO: 44, CDR2 of SEQ ID NO: 51, and CDR3 of SEQ ID NO: 50;

antibody (h), wherein the light chain variable region thereof has CDR1 of SEQ ID NO: 55, CDR2 of SEQ ID NO: 42, and CDR3 of SEQ ID NO: 56, and the heavy chain variable region thereof has CDR1 of SEQ ID NO: 44, CDR2 of SEQ ID NO: 45, and CDR3 of SEQ ID NO: 50;

antibody (i), wherein the light chain variable region thereof has CDR1 of SEQ ID NO: 41, CDR2 of SEQ ID NO: 53, and CDR3 of SEQ ID NO: 56, and the heavy chain variable region thereof has CDR1 of SEQ ID NO: 44, CDR2 of SEQ ID NO: 52, and CDR3 of SEQ ID NO: 50;

antibody (j), wherein the light chain variable region thereof has CDR1 of SEQ ID NO: 41, CDR2 of SEQ ID NO: 42, and CDR3 of SEQ ID NO: 56, and the heavy chain variable region thereof has CDR1 of SEQ ID NO: 44, CDR2 of SEQ ID NO: 52, and CDR3 of SEQ ID NO: 50; or antibody (k), wherein the light chain variable region thereof has CDR1 of SEQ ID NO: 41, CDR2 of SEQ ID NO: 42, and CDR3 of SEQ ID NO: 57, and the heavy chain variable region thereof has CDR1 of SEQ ID NO: 44, CDR2 of SEQ ID NO: 52, and CDR3 of SEQ ID NO: 50.

2. The antibody of claim 1, wherein the amino acid sequence of the heavy chain variable region of the antibody is shown in positions 124 to 239 of SEQ ID NO: 13, and the amino acid sequence of the light chain variable region of the antibody is shown in positions 1-108 of SEQ ID NO: 13;

the amino acid sequence of the heavy chain variable region of the antibody is shown in positions 124 to 239 of SEQ ID NO: 59, and the amino acid sequence of the light chain variable region of the antibody is shown in positions 1-108 of SEQ ID NO: 59;

the amino acid sequence of the heavy chain variable region of the antibody is shown in positions 124 to 239 of SEQ ID NO: 61, and the amino acid sequence of the light chain variable region of the antibody is shown in positions 1-108 of SEQ ID NO: 61;

the amino acid sequence of the heavy chain variable region of the antibody is shown in positions 124 to 239 of SEQ ID NO: 63, and the amino acid sequence of the light chain variable region of the antibody is shown in positions 1-108 of SEQ ID NO: 63;

the amino acid sequence of the heavy chain variable region of the antibody is shown in positions 124 to 239 of SEQ ID NO: 65, and the amino acid sequence of the light chain variable region of the antibody is shown in positions 1-108 of SEQ ID NO: 65;

the amino acid sequence of the heavy chain variable region of the antibody is shown in positions 124 to 239 of SEQ ID NO: 67, and the amino acid sequence of the light chain variable region of the antibody is shown in positions 1-108 of SEQ ID NO: 67;

the amino acid sequence of the heavy chain variable region of the antibody is shown in positions 124 to 239 of SEQ ID NO: 69, and the amino acid sequence of the light chain variable region of the antibody is shown in positions 1-108 of SEQ ID NO: 69;

the amino acid sequence of the heavy chain variable region of the antibody is shown in positions 124 to 239 of SEQ ID NO: 71, and the amino acid sequence of the light chain variable region of the antibody is shown in positions 1-108 of SEQ ID NO: 71;

the amino acid sequence of the heavy chain variable region of the antibody is shown in positions 124 to 239 of SEQ ID NO: 73, and the amino acid sequence of the light chain variable region of the antibody is shown in positions 1-108 of SEQ ID NO: 73;

the amino acid sequence of the heavy chain variable region of the antibody is shown in positions 124 to 239 of SEQ ID NO: 75, and the amino acid sequence of the light chain variable region of the antibody is shown in positions 1-108 of SEQ ID NO: 75; or the amino acid sequence of the heavy chain variable region of the antibody is shown in positions 124 to 239 of SEQ ID NO: 77, and the amino acid sequence of the light chain variable region of the antibody is shown in positions 1-108 of SEQ ID NO: 77.

3. The antibody of claim 1, wherein the antibody is the antibody (a).

4. The antibody of claim 3, wherein the heavy chain variable region of the antibody comprises the amino acid sequence shown in positions 124 to 239 of SEQ ID NO: 13, and light chain variable region of the antibody comprises the amino acid sequence shown in positions 1-108 of SEQ ID NO: 13.

5. A pharmaceutical composition comprising the antibody of claim 1 and a pharmaceutical acceptable excipient.

* * * * *